(12) United States Patent
Strop et al.

(10) Patent No.: US 11,602,525 B2
(45) Date of Patent: Mar. 14, 2023

(54) ANTIBODY-DRUG CONJUGATES WITH HIGH DRUG LOADING

(71) Applicants: RINAT NEUROSCIENCE CORP., South San Francisco, CA (US); PFIZER INC., New York, NY (US)

(72) Inventors: Pavel Strop, San Mateo, CA (US); Katherine Anne Delaria, Walnut Creek, CA (US); Magdalena Dorywalska, Redwood City, CA (US); Davide Luciano Foletti, Menlo Park, CA (US); Russell George Dushin, Old Lyme, CT (US); David Louis Shelton, Oakland, CA (US); Arvind Rajpal, San Francisco, CA (US)

(73) Assignees: RINAT NEUROSCIENCE CORP., South San Francisco, CA (US); PFIZER INC., New York, NY (US)

(*) Notice: Subject to any disclaimer, the term of this patent is extended or adjusted under 35 U.S.C. 154(b) by 336 days.

(21) Appl. No.: 15/306,481

(22) PCT Filed: Apr. 21, 2015

(86) PCT No.: PCT/IB2015/052918
§ 371 (c)(1),
(2) Date: Oct. 24, 2016

(87) PCT Pub. No.: WO2015/162563
PCT Pub. Date: Oct. 29, 2015

(65) Prior Publication Data
US 2017/0043033 A1    Feb. 16, 2017

Related U.S. Application Data

(60) Provisional application No. 62/147,293, filed on Apr. 14, 2015, provisional application No. 62/103,999, (Continued)

(51) Int. Cl.
*A61K 31/427* (2006.01)
*A61K 47/68* (2017.01)
(Continued)

(52) U.S. Cl.
CPC ............ *A61K 31/427* (2013.01); *A61K 47/65* (2017.08); *A61K 47/6803* (2017.08);
(Continued)

(58) Field of Classification Search
None
See application file for complete search history.

(56) References Cited

U.S. PATENT DOCUMENTS 6,919,076 B1    7/2005  Green et al.
7,208,171 B2    4/2007  Messersmith et al.
(Continued)

FOREIGN PATENT DOCUMENTS

EP    0725145 A1    8/1996
WO    0043492 A2    7/2000
(Continued)

OTHER PUBLICATIONS

Grunberg et al., PLOS One, Apr. 2013, vol. 8, Issue 4, 60350 (Year: 2013).*
(Continued)

*Primary Examiner* — Karl J Puttlitz
(74) *Attorney, Agent, or Firm* — Susan Wang

(57) ABSTRACT

The present invention provides transglutaminase-mediated antibody-drug conjugates with high anti-body-drug ratio (DAR) comprising 1) glutamine-containing tags, endogenous glutamines, and/or endogenous glutamines made reactive by antibody engineering or an engineered transglutaminase (e.g., with altered substrate specifity); and 2) amine donor agents comprising amine donor units, linkers, and agent moieties, wherein the DAR is at least about 5. The
(Continued)

invention also provides methods of making and methods of using such higher drug loaded antibody-drug conjugates.

17 Claims, 24 Drawing Sheets

Specification includes a Sequence Listing.

Related U.S. Application Data filed on Jan. 15, 2015, provisional application No. 62/028,731, filed on Jul. 24, 2014, provisional application No. 61/984,645, filed on Apr. 25, 2014.

(51) Int. Cl.
| | |
|---|---|
| *A61K 47/65* | (2017.01) |
| *C07K 16/30* | (2006.01) |
| *G01N 33/574* | (2006.01) |
| *A61K 39/00* | (2006.01) |

(52) U.S. Cl.
CPC ...... *A61K 47/6849* (2017.08); *A61K 47/6851* (2017.08); *A61K 47/6889* (2017.08); *C07K 16/3076* (2013.01); *G01N 33/57492* (2013.01); *A61K 2039/505* (2013.01); *G01N 2333/705* (2013.01)

(56) References Cited

U.S. PATENT DOCUMENTS

| | | | |
|---|---|---|---|
| 7,375,078 | B2 | 5/2008 | Feng |
| 7,521,541 | B2 | 4/2009 | Eigenbrot et al. |
| 8,871,908 | B2 * | 10/2014 | Liu ................... C07K 16/303 530/387.1 |
| 2004/0266690 | A1 | 12/2004 | Pool |
| 2006/0019258 | A1 | 1/2006 | Yeakley |
| 2007/0184537 | A1 | 8/2007 | Schibli et al. |
| 2008/0279868 | A1 | 11/2008 | Boyd et al. |
| 2010/0278750 | A1 | 11/2010 | Krippner et al. |
| 2011/0184147 | A1 | 7/2011 | Kamiya et al. |
| 2013/0230543 | A1 | 9/2013 | Pons et al. |
| 2014/0357844 | A1 * | 12/2014 | Liu ................... C07K 16/3076 530/391.9 |
| 2016/0193356 | A1 | 7/2016 | Farias et al. |

FOREIGN PATENT DOCUMENTS

| | | |
|---|---|---|
| WO | 2009059278 A1 | 5/2009 |
| WO | 2010002042 A1 | 1/2010 |
| WO | 2010011096 A2 | 1/2010 |
| WO | 2010045270 A2 | 4/2010 |
| WO | 2010080124 A2 | 7/2010 |
| WO | 2011069164 A2 | 6/2011 |
| WO | 2011090305 A2 | 7/2011 |
| WO | 2011090306 A2 | 7/2011 |
| WO | 2011122922 A2 | 10/2011 |
| WO | 2012059882 A2 | 5/2012 |
| WO | 2013068946 A2 | 5/2013 |
| WO | 2013092998 A1 | 6/2013 |

OTHER PUBLICATIONS

Strop et al., Nat Biotechnol. Jul. 2015;33(7):694-6 (Year: 2015).*
Strop et al., Nat Biotechnol. Jul. 2015;33(7):694-6, supplemental (Year: 2015).*
Carter, P., "Bispecific human IgG by design," Journal of Immunological Methods, 2001, 7-15, vol. 248.
The International Search Report for Appln. No. PCT/IB2015/052918 completed Aug. 14, 2015.
The Written Opinion of the International Searching Authority for Appln No. PCT/IB2015/052918 completed on Aug. 14, 2015.
Doronina, S., et al., "Novel Peptide Linkers for Highly Potent Antibody—Auristatin Conjugate," Bioconjugate Chemistry, 2008, 1960-1963, vol. 19, No. 10.
Farias, S., et al., "Mass Spectrometric Characterization of Transglutaminase Based Site-Specific Antibody-Drug Conjugates," Bioconjugate Chemistry, 2014, 240-250, vol. 25, No. 2.
Fontana, A., et al., "Site-specific modification and PEGylation of pharmaceutical proteins mediated by transglutaminase," Advanced Drug Delivery Reviews, 2008, 13-28, vol. 60.
Gentle, I., et al., "Direct Production of Proteins with N-Terminal Cysteine for Site-Specific Conjugation," Bioconjugate Chemistry, 2004, 658-663, vol. 15, No. 3.
Gomez, N., et al., "Triple Light Chain Antibodies: Factors That Influence Its Formation in Cell Culture," Biotechnology and Bioengineering, 2010, 748-760, vol. 105, No. 4.
Jeger, S., "Site-Specific Conjugation of Tumour-Targeting Antibodies Using Transglutaminase," A Dissertation Submitted to ETH Zurich for the Degree of Doctor of Sciences, Diss. ETH 18696, 2009, 51-85.
Jeger, S., et al., "Site-Specific and Stoichiometric Modification of Antibodies by Bacterial Transglutaminase," Angewandte Chemie International Edition, 2010, 9995-9997, vol. 49, No. 51.
Josten, A., et al., "Use of microbial transglutaminase for the enzymatic biotinylation of antibodies," Journal of Immunological Methods, 2000, 47-54, vol. 240.
Junutula, J., et al., "Site-specific conjugation of a cytotoxic drug to an antibody improves the therapeutic index," Nature Biotechnology, 2008, 925-932, vol. 26, No. 8.
Kamiya, N., et al., "Site-specific cross-linking of functional proteins by transglutamination," Enzyme and Microbial Technology, 2003, 492-496, vol. 33.
Lin, C., et al., "Transglutaminase-Catalyzed Site-Specific Conjugation of Small-Molecule Probes to Proteins in Vitro and on the Surface of Living Cells," Journal of the American Chemical Society, 2006, 4542-4543, vol. 128.
Mero, A., et al., "Transglutaminase-Mediated PEGylation of Proteins: Direct Identification of the Sites of Protein Modification by Mass Spectrometry using a Novel Monodisperse PEG," Bioconjugate Chemistry, 2009, 384-389, vol. 20, No. 2.
Meusel, M. (2004). "Synthesis of Hapten-Protein Conjugates Using Microbial Transglutaminase." In C. M. Niemeyer (Ed.), "Methods in Molecular Biology, vol. 283: Bioconjugation Protocols: Strategies and Methods" (pp. 109-123). Totowa, NJ: Humana Press Inc.
Mindt, T., et al., "Modification of Different IgG1 Antibodies via Glutamine and Lysine using Bacterial and Human Tissue Transglutaminase," Bioconjugate Chemistry, 2008, 271-278, vol. 19, No. 1.
Ohtsuka, T., et al., "Comparison of Substrate Specificities of Transglutaminases Using Synthetic Peptides as Acyl donors," Bioscience, Biotechnology, and Biochemistry, 2000, 2608-2613, vol. 64, No. 12.
Russell, D., et al., "Transglutaminase May Mediate Certain Physiological Effects of Endogenous Amines and of Amine-Containing Therapeutic Agents," Life Sciences, 1982, 1499-1508, vol. 30, No. 18.
Sato, H., "Enzymatic procedure for site-specific pegylation of proteins," Advanced Drug Delivery Reviews, 2002, 487-504, vol. 54.
Strop, P., et al., "Location Matters: Site of Conjugation Modulates Stability and Pharmacokinetics of Antibody Drug Conjugates," Chemistry & Biology, 2013, 161-167, vol. 20, No. 2.
Takazawa, T., et al., "Enzymatic Labeling of a Single Chain Variable Fragment of an Antibody With Alkaline Phosphatase by Microbial Transglutaminase," Biotechnology and Bioengineering, 2004, 399-404, vol. 86, No. 4.
Tanaka, T., et al., "N-terminal glycine-specific protein conjugation catalyzed by microbial transglutaminase," FEBS Letters, 2005, 2092-2096, vol. 579, No. 10.
Tanaka, T., et al., "Peptidyl Linkers for Protein Heterodimerization Catalyzed by Microbial Transglutaminase," Bioconjugate Chemistry, 2004, 491-497, vol. 15, No. 3.
Veronese, F., et al., "PEGylation, successful approach to drug delivery," Drug Discovery Today, 2005, 1451-1458, vol. 10, No. 21.

(56) References Cited

OTHER PUBLICATIONS

Grünberg, J., et al., "DOTA-Functionalized Polylysine: A High Number of DOTA Chelates Positively Influences the Biodistribution of Enzymatic Conjugated Anti-Tumor Antibody chCE7agl," PLOS One, 2013, e60350, vol. 8, No. 4.

Dosio, F., et al., "Immunotoxins and Anticancer Drug Conjugate Assemblies: The Role of the Linkage between Components," 2011, Toxins, 848-883, vol. 3.

Plagmann, I., et al., "Transglutaminase-catalyzed covalent multimerization of camelidae anti-human TNF single domain antibodies improves neutralizing activity," 2009, Journal of Biotechnology, 170-178, vol. 142.

Yu, L., et al., "Interaction between Bevacizumab and Murine VEGF-A: A Reassessment," 2008, Investigative Ophthalmology & Visual Science, 522-527, vol. 49, No. 2.

* cited by examiner

FIG. 1

Cytotoxicity of increasingly higher loaded, site-specifically conjugated anti-Trop-2-ADCs in BxPC3 cells with high target expression (Trop2 +++)

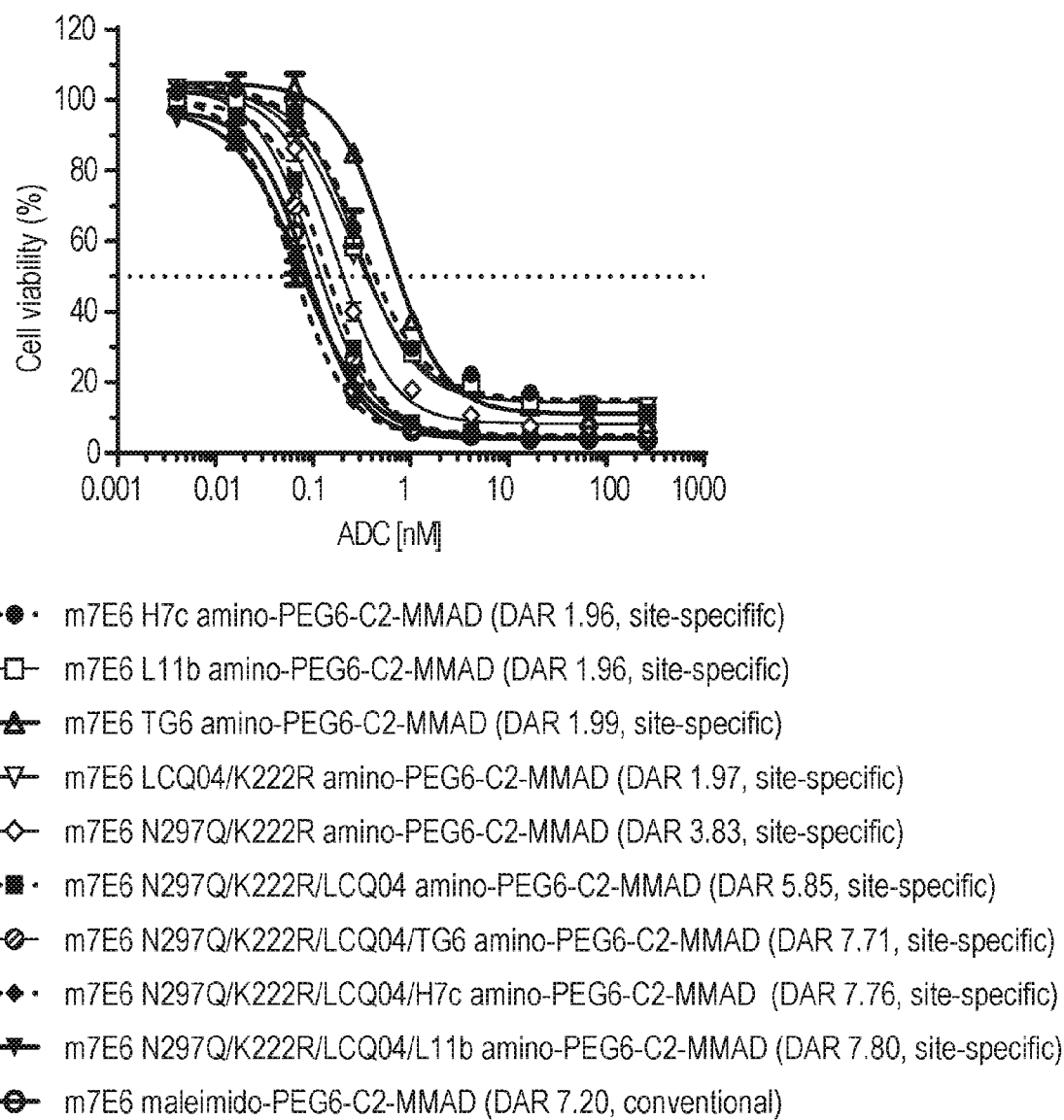

- m7E6 H7c amino-PEG6-C2-MMAD (DAR 1.96, site-specififc)
- m7E6 L11b amino-PEG6-C2-MMAD (DAR 1.96, site-specific)
- m7E6 TG6 amino-PEG6-C2-MMAD (DAR 1.99, site-specific)
- m7E6 LCQ04/K222R amino-PEG6-C2-MMAD (DAR 1.97, site-specific)
- m7E6 N297Q/K222R amino-PEG6-C2-MMAD (DAR 3.83, site-specific)
- m7E6 N297Q/K222R/LCQ04 amino-PEG6-C2-MMAD (DAR 5.85, site-specific)
- m7E6 N297Q/K222R/LCQ04/TG6 amino-PEG6-C2-MMAD (DAR 7.71, site-specific)
- m7E6 N297Q/K222R/LCQ04/H7c amino-PEG6-C2-MMAD (DAR 7.76, site-specific)
- m7E6 N297Q/K222R/LCQ04/L11b amino-PEG6-C2-MMAD (DAR 7.80, site-specific)
- m7E6 maleimido-PEG6-C2-MMAD (DAR 7.20, conventional)

FIG. 2

Cytotoxicity of increasingly higher loaded, site-specifically conjugated anti-Trop-2-ADCs in Colo205 cells with moderate target expression (Trop2 +)

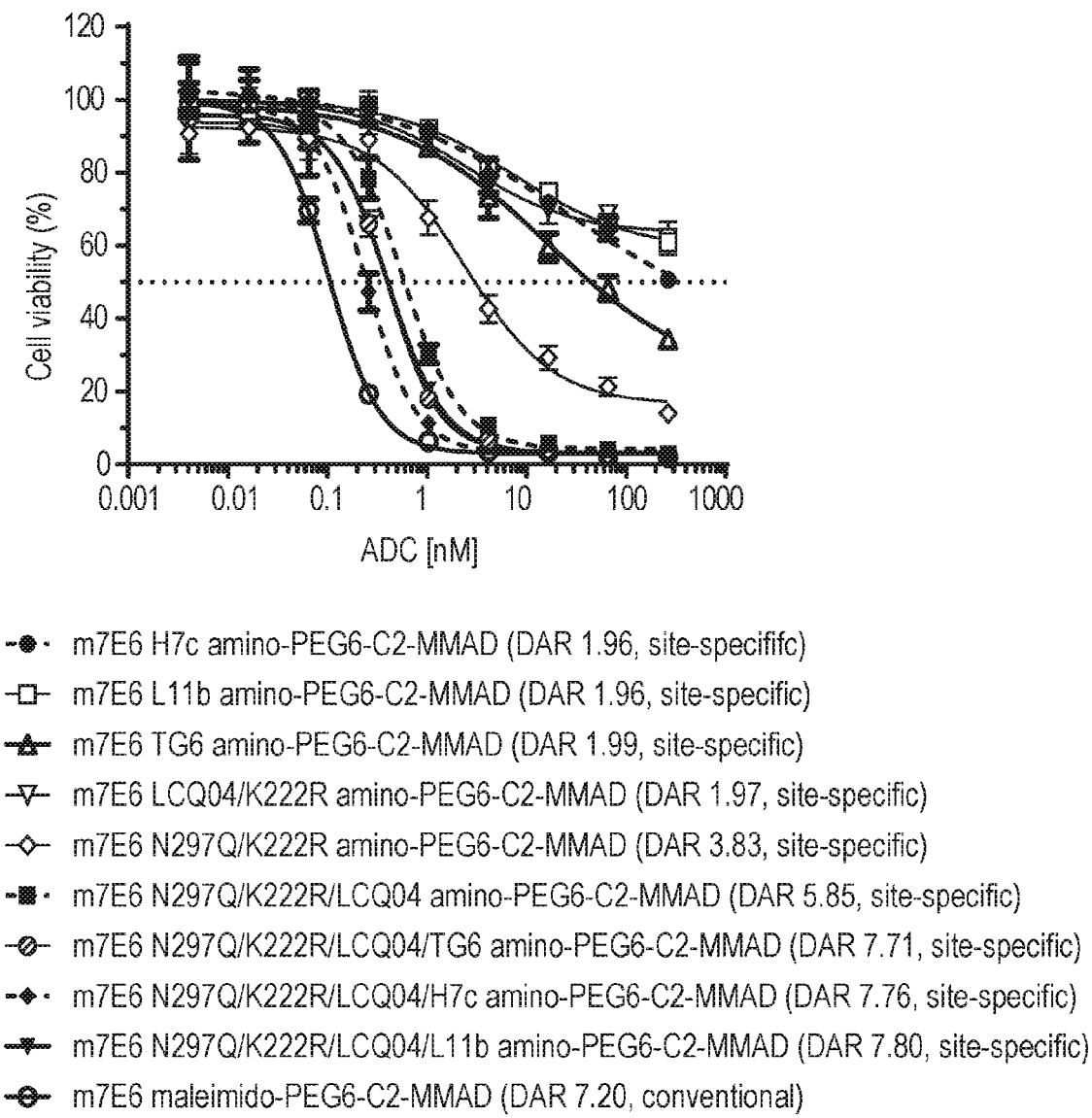

- ● - m7E6 H7c amino-PEG6-C2-MMAD (DAR 1.96, site-spicififc)
- □ - m7E6 L11b amino-PEG6-C2-MMAD (DAR 1.96, site-specific)
- ▲ - m7E6 TG6 amino-PEG6-C2-MMAD (DAR 1.99, site-specific)
- ▽ - m7E6 LCQ04/K222R amino-PEG6-C2-MMAD (DAR 1.97, site-specific)
- ◇ - m7E6 N297Q/K222R amino-PEG6-C2-MMAD (DAR 3.83, site-specific)
- ■ - m7E6 N297Q/K222R/LCQ04 amino-PEG6-C2-MMAD (DAR 5.85, site-specific)
- ⊘ - m7E6 N297Q/K222R/LCQ04/TG6 amino-PEG6-C2-MMAD (DAR 7.71, site-specific)
- ◆ - m7E6 N297Q/K222R/LCQ04/H7c amino-PEG6-C2-MMAD (DAR 7.76, site-specific)
- ✳ - m7E6 N297Q/K222R/LCQ04/L11b amino-PEG6-C2-MMAD (DAR 7.80, site-specific)
- ○ - m7E6 maleimido-PEG6-C2-MMAD (DAR 7.20, conventional)

FIG. 3

Cytotoxicity of increasingly higher loaded, site-specifically conjugated anti-Trop-2-ADCs in CF-PAC1 cells with low target expression (Trop2 (+))

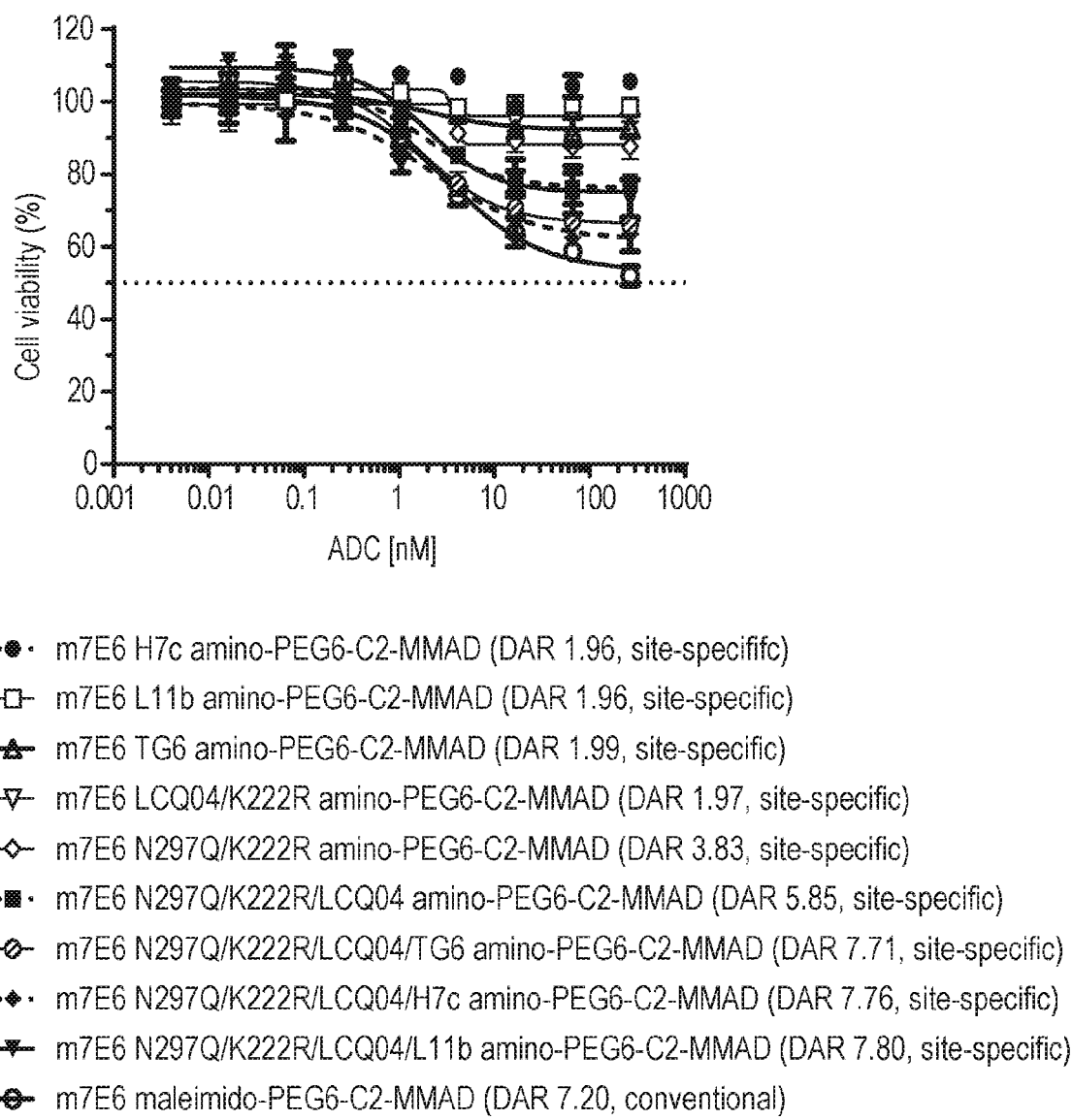

- m7E6 H7c amino-PEG6-C2-MMAD (DAR 1.96, site-specififc)
- m7E6 L11b amino-PEG6-C2-MMAD (DAR 1.96, site-specific)
- m7E6 TG6 amino-PEG6-C2-MMAD (DAR 1.99, site-specific)
- m7E6 LCQ04/K222R amino-PEG6-C2-MMAD (DAR 1.97, site-specific)
- m7E6 N297Q/K222R amino-PEG6-C2-MMAD (DAR 3.83, site-specific)
- m7E6 N297Q/K222R/LCQ04 amino-PEG6-C2-MMAD (DAR 5.85, site-specific)
- m7E6 N297Q/K222R/LCQ04/TG6 amino-PEG6-C2-MMAD (DAR 7.71, site-specific)
- m7E6 N297Q/K222R/LCQ04/H7c amino-PEG6-C2-MMAD (DAR 7.76, site-specific)
- m7E6 N297Q/K222R/LCQ04/L11b amino-PEG6-C2-MMAD (DAR 7.80, site-specific)
- m7E6 maleimido-PEG6-C2-MMAD (DAR 7.20, conventional)

FIG. 4

Cytotoxicity of increasingly higher loaded, site-specifically conjugated anti-Trop-2-ADCs in SW620 cells with no target expression (Trop2 -)

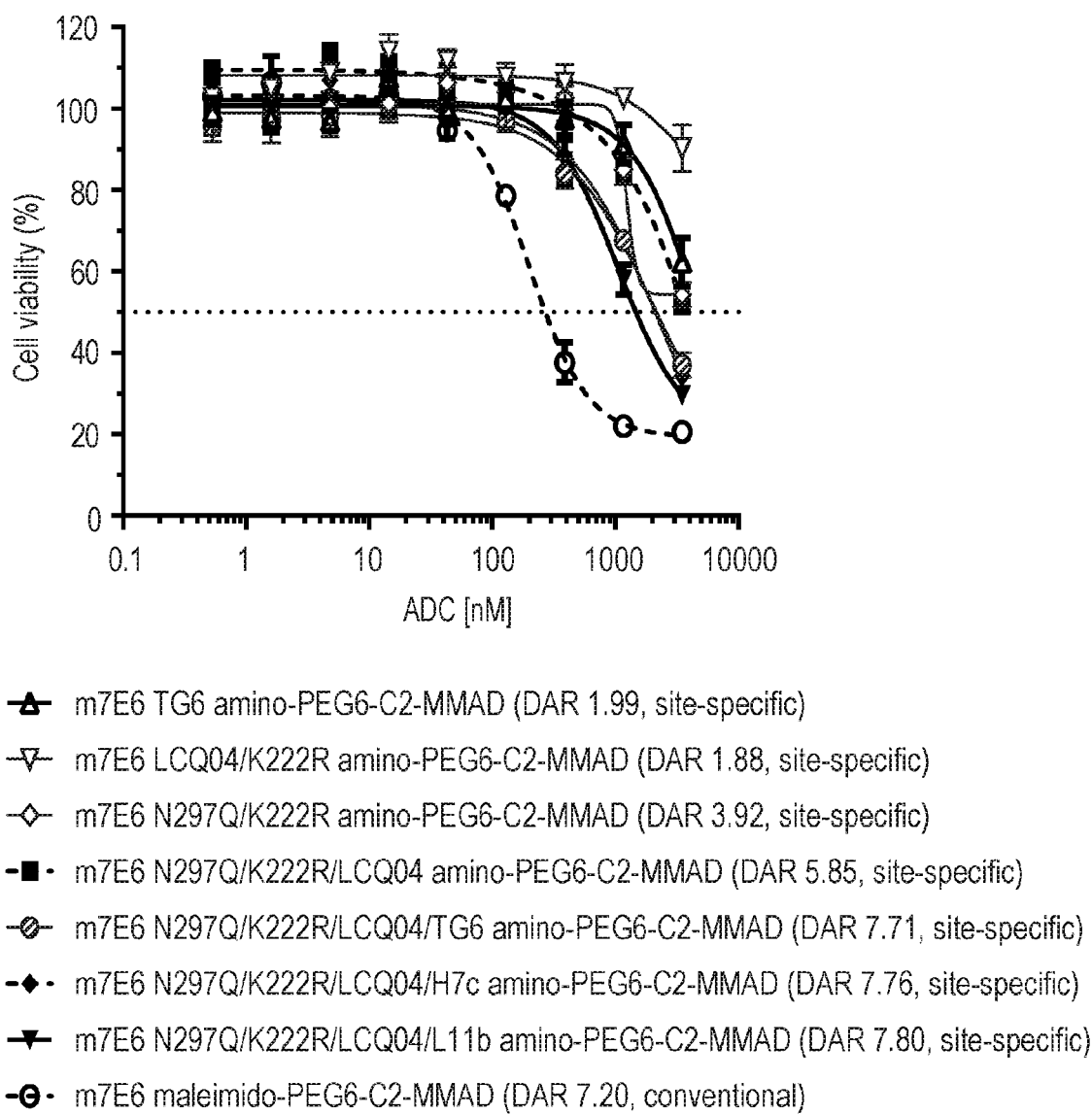

- △ m7E6 TG6 amino-PEG6-C2-MMAD (DAR 1.99, site-specific)
- ▽ m7E6 LCQ04/K222R amino-PEG6-C2-MMAD (DAR 1.88, site-specific)
- ◇ m7E6 N297Q/K222R amino-PEG6-C2-MMAD (DAR 3.92, site-specific)
- ■ m7E6 N297Q/K222R/LCQ04 amino-PEG6-C2-MMAD (DAR 5.85, site-specific)
- ⊘ m7E6 N297Q/K222R/LCQ04/TG6 amino-PEG6-C2-MMAD (DAR 7.71, site-specific)
- ◆ m7E6 N297Q/K222R/LCQ04/H7c amino-PEG6-C2-MMAD (DAR 7.76, site-specific)
- ▼ m7E6 N297Q/K222R/LCQ04/L11b amino-PEG6-C2-MMAD (DAR 7.80, site-specific)
- ○ m7E6 maleimido-PEG6-C2-MMAD (DAR 7.20, conventional)

FIG. 5

Side-by-side comparison of cytotoxicity of increasingly higher loaded, site-specifically and conventionally conjugated anti-Trop-2-ADCs in Colo205 cells with moderate target expression (Trop2 +)

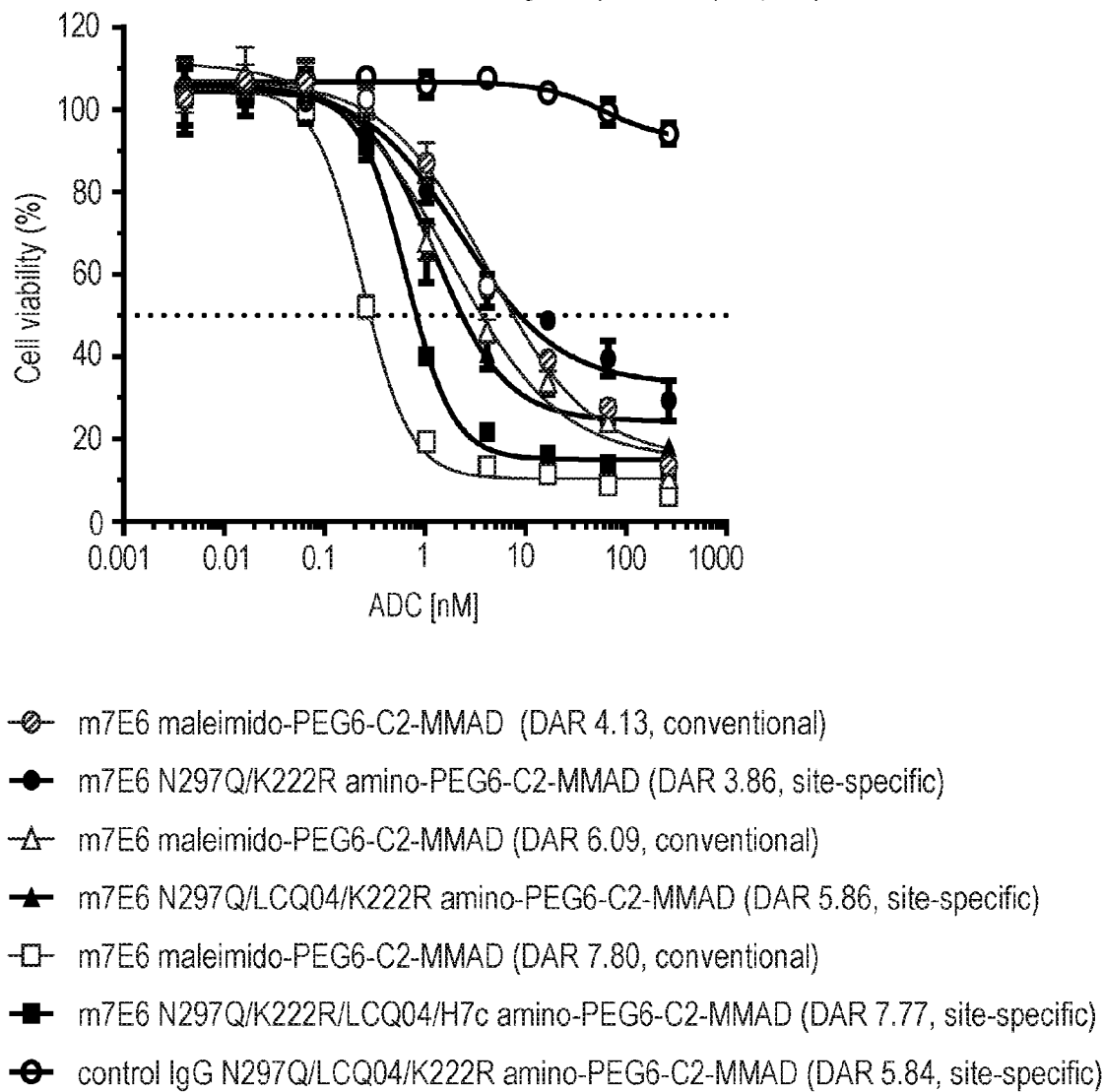

- ⊘ m7E6 maleimido-PEG6-C2-MMAD (DAR 4.13, conventional)
- ● m7E6 N297Q/K222R amino-PEG6-C2-MMAD (DAR 3.86, site-specific)
- △ m7E6 maleimido-PEG6-C2-MMAD (DAR 6.09, conventional)
- ▲ m7E6 N297Q/LCQ04/K222R amino-PEG6-C2-MMAD (DAR 5.86, site-specific)
- □ m7E6 maleimido-PEG6-C2-MMAD (DAR 7.80, conventional)
- ■ m7E6 N297Q/K222R/LCQ04/H7c amino-PEG6-C2-MMAD (DAR 7.77, site-specific)
- ⊖ control IgG N297Q/LCQ04/K222R amino-PEG6-C2-MMAD (DAR 5.84, site-specific)

anti-Trop-2 site-specific ADC m7E6 N297Q/K222R/LCQ04/H7c amino-PEG6-C2-MMAD (DAR 7.76) induces long term tumor stasis in Colo205 Xenograft Model

- ◇ m7E6 N297Q/K222R amino-PEG6-C2-MMAD (DAR 3.92, site-specific)
- ● m7E6 maleimido-PEG6-C2-MMAD (DAR 7.20, conventional)
- ■ m7E6 N297Q/K222R/LCQ04/H7c amino-PEG6-C2-MMAD (DAR 7.76, site-specific)
- ○ control IgG N297Q/K222R amino-PEG6-C2-MMAD (DAR 3.68, site-specific)

FIG. 7

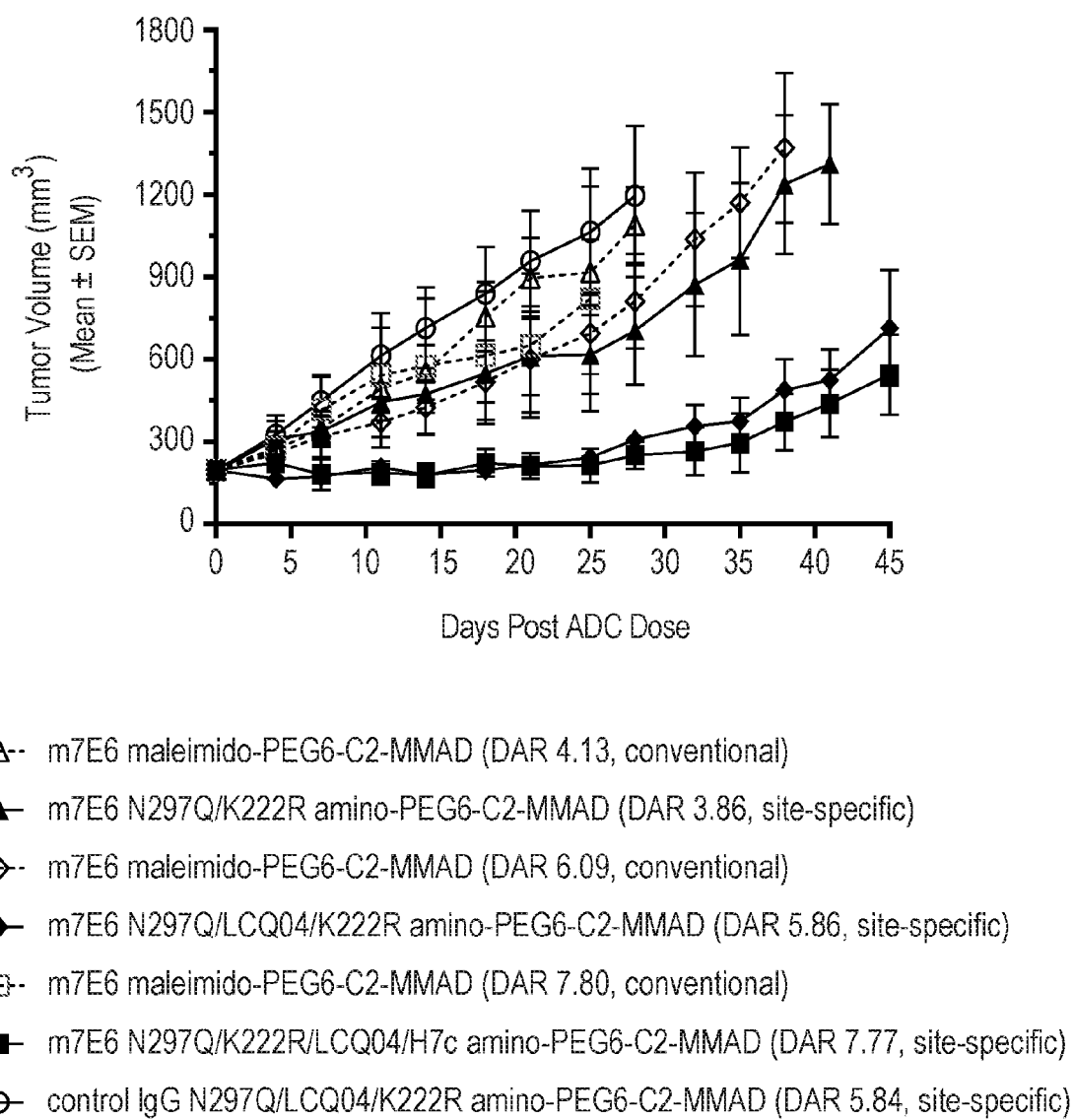

anti-Trop-2 site-specific ADCs m7E6 N297Q/LCQ04/K222R amino-PEG6-C2-MMAD (DAR 5.86) and m7E6 N297Q/K222R/LCQ04/H7c amino-PEG6-C2-MMAD (DAS7.77) induce long term tumor stasis in Colo205 Xenograft Model

- △ m7E6 maleimido-PEG6-C2-MMAD (DAR 4.13, conventional)
- ▲ m7E6 N297Q/K222R amino-PEG6-C2-MMAD (DAR 3.86, site-specific)
- ◇ m7E6 maleimido-PEG6-C2-MMAD (DAR 6.09, conventional)
- ◆ m7E6 N297Q/LCQ04/K222R amino-PEG6-C2-MMAD (DAR 5.86, site-specific)
- ▫ m7E6 maleimido-PEG6-C2-MMAD (DAR 7.80, conventional)
- ■ m7E6 N297Q/K222R/LCQ04/H7c amino-PEG6-C2-MMAD (DAR 7.77, site-specific)
- ○ control IgG N297Q/LCQ04/K222R amino-PEG6-C2-MMAD (DAR 5.84, site-specific)

Mouse PK, 6 mg/kg

- Total mAb: WT
- ADC m7E6 N297Q/K222R/LCQ04 Amino-PEG6-C2-MMAD (DAR 5.85 site-specific)
- ADC m7E6 N297Q/K222R/LCQ04/H7c Amino-PEG6-C2-MMAD (DAR 7.76 site-specific)
- ADC m7E6 maleimido-PEG6-C2-MMAD (DAR 7.8, conventional)

Mouse PK, 6 mg/kg

- Total mAb: WT
- mAb m7E6 maleimido-PEG6-C2-MMAD (DAR 7.80, conventional)
- ADC m7E6 maleimido-PEG6-C2-MMAD (DAR 7.8, conventional)

ADC Rat PK

- ■ mAb: m7E6 WT
- ■ ADC m7E6 N297Q/K222R/LCQ04 Amino-PEG6-C2-MMAD (DAR 5.85, site-specific)
- ◆ ADC m7E6 N297Q/K222R/LCQ04/H7c Amino-PEG6-C2-MMAD (DAR 7.76, site-specific)
- ▼ ADC m7E6 maleimido-PEG6-C2-MMAD (DAR 7.8 conventional)

mAb vs. ADC Rat PK

- ◆ mAb: m7E6 WT
- ○ ADC m7E6 maleimido-PEG6-C2-MMAD (DAR 7.8 conventional)
- ● mAb m7E6 maleimido-PEG6-C2-MMAD (DAR 7.8 conventional)

- mAb: m7E6 WT
- mAb: m7E6 H7c Amino-PEG6-C2-MMAD (DAR 1.99 site-specific)
- mAb: m7E6 N297Q/K222R/LCQ04 Amino-PEG6-C2-MMAD (DAR 5.85 site-specific)
- mAb: m7E6 N297Q/K222R/LCQ04/H7c Amino-PEG6-C2-MMAD (DAR 7.76 site-specific)

- mAb: m7E6 WT
- mAb: m7E6 TG6 Amino-PEG6-C2-MMAD (DAR 1.96 site-specific)
- mAb: m7E6 N297Q/K222R/LCQ04 Amino-PEG6-C2-MMAD (DAR 5.85 site-specific)
- mAb: m7E6 N297Q/K222R/LCQ04/TG6 Amino-PEG6-C2-MMAD (DAR 7.7 site-specific)

Mouse TK, 200 mg/kg dose

● ADC m7E6 maleimido-PEG6-C2-MMAD (DAR 7.8 conventional)

▲ ADC m7E6 N297Q/K222R/LCQ04/H7c Amino-PEG6-C2-MMAD (DAR 7.76 site-specific)

Body Weight 200mg/kg dose

● Control

■ m7E6 maleimido-PEG6-C2-MMAD (DAR 7.8, conventional)

◇ m7E6 N297Q/K222R/LCQ04 Amino-PEG6-C2-MMAD (DAR 5.85, site-specific)

△ m7E6 N297Q/K222R/LCQ04/TG6 Amino-PEG6-C2-MMAD (DAR 7.71, site-specific)

FIG. 15

Cytotoxicity of increasingly higher loaded, site-specifically conjugated anti-Trop-ADCs up to DAR 9.4 in Colo205 cells with moderate target expression (Trop2 +)

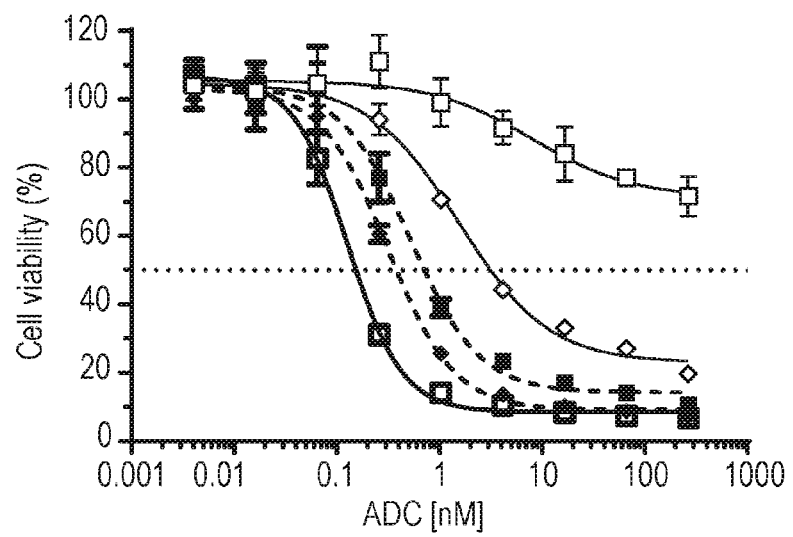

- □- m7E6 L11b amino-PEG6-C2-MMAD (DAR 1.96, site-specific)
- ◇- m7E6 N297Q/K222R amino-PEG6-C2-MMAD (DAR 3.9, site-specific)
- ■· m7E6 N297Q/K222R/LCQ04 amino-PEG6-C2-MMAD (DAR 5.95, site-specific)
- ◆· m7E6 N297Q/K222R/LCQ04/H7c amino-PEG6-C2-MMAD (DAR 7.6, site-specific)
- ⊟- m7E6 N297Q/K222R/LCQ04/L11b/H7c amino-PEG6-C2-MMAD (DAR 9.4, site-specific)

FIG. 16

Cytotoxicity of increasingly higher loaded, site-specifically conjugated anti-Trop-ADCsup to DAR 9.4 in CF-PAC1 cells with low target expression (Trop2 (+))

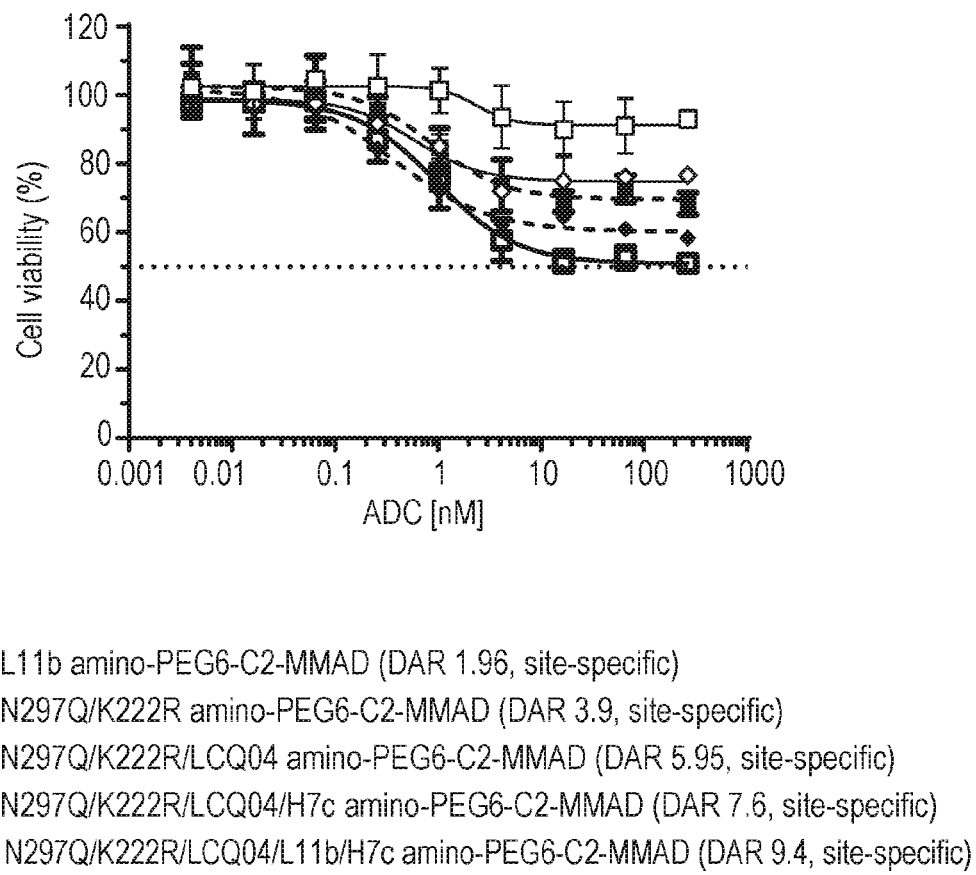

- —□— m7E6 L11b amino-PEG6-C2-MMAD (DAR 1.96, site-specific)
- —◇— m7E6 N297Q/K222R amino-PEG6-C2-MMAD (DAR 3.9, site-specific)
- —■— m7E6 N297Q/K222R/LCQ04 amino-PEG6-C2-MMAD (DAR 5.95, site-specific)
- —◆— m7E6 N297Q/K222R/LCQ04/H7c amino-PEG6-C2-MMAD (DAR 7.6, site-specific)
- —⊟— m 7E6 N297Q/K222R/LCQ04/L11b/H7c amino-PEG6-C2-MMAD (DAR 9.4, site-specific)

Cytotoxicity of increasingly higher loaded, site-specifically conjugated anti-BCMA-ADCs in L363 cells ● Ab1 LCQ05/K222R splicostatin (DAR 1.9, site-specific)

□ Ab1 N297Q/K222R splicostatin (DAR 3.7, site-specific)

△ Ab1 N297Q/K222R/LCQ05 splicostatin (DAR 5.9, site-specific)

Cytotoxicity of increasingly higher loaded, site-specifically conjugated anti-BCMA-ADCs in MM1S cells

- ● Ab1 LCQ04/K222R splicostatin (DAR 1.9, site-specific)
- □ Ab1 N297Q/K222R splicostatin (DAR 3.7, site-specific)
- △ Ab1 N297Q/K222R/LCQ05 splicostatin (DAR 5.9, site-specific)

ANTIBODY-DRUG CONJUGATES WITH HIGH DRUG LOADING

CROSS-REFERENCE TO RELATED APPLICATIONS

This application is a § 371 filing of PCT/IB2015/052918 filed Apr. 21, 2015, which claims the benefits of U.S. provisional application no. 61/984,645 filed Apr. 25, 2014, 62/028,731 filed Jul. 24, 2014, 62/103,999 filed Jan. 15, 2015, and 62/147,293 filed Apr. 14, 2015, all of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72078A_SEQListing_ST25.txt" created on Oct. 24, 2016 and having a size of 9 KB. The sequence listing contained in this .txt file is part of the specification and is herein incorporated by reference in its entirety.

FIELD

The present invention relates generally to transglutaminase-mediated antibody-drug conjugates with high drug-antibody ratio (DAR) comprising 1) glutamine-containing tags, endogenous glutamines, and/or endogenous glutamines made reactive by antibody engineering or an engineered transglutaminase (e.g., with altered substrate specifity); and 2) amine donor agents comprising amine donor units, linkers, and agent moieties. The invention also relates to methods of making and methods of using such antibody-drug conjugates.

BACKGROUND

Antibody therapy provides targeted therapeutic treatment in patients with various disorders, such as cancers and immunological diseases, and therefore has played an important role in biological research. Different approaches of targeted antibody therapy, including antibody-drug conjugates (ADC), have been explored. See, e.g., Doronina et al., *Bioconj. Chem.* 19:1960-1963 (2008); and Junutula et al., *Nat. Biotechnol.* 26: 925-932 (2008).

In the case of antibody-drug conjugates (i.e., immunoconjugates), cytotoxic small molecules (drugs) are generally linked or conjugated to antibodies for targeted local delivery of the drug moieties to tumors. Conventional conjugating methods for an ADC include chemical modification through either the lysine side chain amines or through the cysteine sulfhydryl groups activated by reducing the interchain disulfide bonds. ADCETRIS® (brentuximab vedotin) and KADCYLA® (ado-trastuzumab emtansine) are two examples of ADCs using these conventional methods. See, e.g., Tanaka et al, *FEBS Letters* 579:2092-2096 (2005); and Strop, *Bioconj. Chem.*, (in press) (2014). Conventional ADC conjugation methods tend to yield heterogeneous mixtures of varying number of drugs attached at non-specific positions with variable safety profiles, efficacy, and clearance rate. See, e.g., Wang et al., *Protein Sci.* 14: 2436-2446 (2005); and Firer and Gellerman, *J. of Hematology & Oncology*, 5:70 (2012). ADCs with two to four drugs per antibody have been reported to be generally superior to more heavily loaded conjugates (e.g., greater than four drugs per antibody) in terms of in vivo efficacy; tolerability; and pharmacokinetics resulting in higher therapeutic index. See, e.g., Hamblett et al., *Clinical Cancer Research*, 10: 7063-7070 (2004).

Enzymatic approaches using a transglutaminase for making an antibody-drug conjugate have also been explored recently. Transglutaminases (EC2.3.2.13; protein-glutamine:gamma-glutamyltransferse; protein-glutamine:amine γ-glutamyltransferase; CAS 80146-85-6) belong to a family of enzymes that catalyze the acyl addition to a primary amine, wherein the gamma-carboxamide group of peptide-bound γ-glutamyl residue is the acyl donor, and the primary amine is the acyl acceptor and the amine donor. Antibody and drug conjugation using a transglutaminase provides the advantages of high selectivity, simplified reaction procedures, and mild reaction conditions. See, e.g., Strop et al., *Chemistry & Biology*, 20:161-167 (2013); and Farias et al., *Bioconj. Chem.* 25(2):240-250 (2014). US20130230543 and US2013/0122020 describe transglutaminase-mediated site-specific conjugation of antibodies and small molecules.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

SUMMARY

The present invention relates generally to transglutaminase-mediated site-specific antibody-drug conjugates (ADCs) with high drug-antibody ratio (DAR) comprising 1) glutamine-containing tags, endogenous glutamines (i.e., native glutamines without engineering, such as glutamines in the variable domains, CDRs, etc.), and/or endogenous glutamines made reactive by antibody engineering or an engineered transglutaminase (e.g., with altered substrate specifity); and 2) amine donor agents comprising amine donor units, linkers, and agent moieties. The inventors have surprisingly discovered that these higher loaded site-specific ADCs (e.g., DAR at least 5 or higher) have higher in vivo potency and less non-specific in vitro cytotoxicity in comparison to the conventional higher loaded ADCs that utilize maleimide linkage. The inventors have further discovered that these higher loaded site-specific ADCs 1) have similar pharmacokinetic profiles as the unconjugated wild-type antibody in mice and improved pharmacokinetic profiles in rats and 2) maintain a comparable safety profile relative to similarly loaded conventional ADCs.

In one aspect, this invention provides an ADC comprising the formula: antibody-$(T\text{-}(X\text{—}Y\text{—}Z_a)_b)_c$, wherein: T is 1) a glutamine-containing tag engineered at a specific site, 2) an endogenous glutamine, and/or 3) an endogenous glutamine made reactive by antibody engineering or an engineered transglutaminase; X is an amine donor unit; Y is a linker; and Z is an agent moiety; X—Y—Z is an amine donor agent site-specifically conjugated to the glutamine-containing tag, the endogenous glutamine, and/or the reactive endogenous glutamine; a is an integer from 1 to 6; b is an integer from 1 to 6; c is an integer from 1 to 20; and wherein the product (drug-antibody ratio) of a, b, and c is at least about 5.

In some embodiments, the T of the antibody-$(T\text{-}(X\text{—}Y\text{—}Z_a)_b)_c$ comprises at least 1 endogenous glutamine (e.g., native or reactive endogenous glutamine). In some embodiments, the reactive endogenous glutamine is made reactive by deglycosylation (e.g., enzymatic deglycosylation) or by an amino acid modification of another amino acid in the antibody (e.g., amino acid substitution at position 297 such as N297Q or N297A (EU numbering scheme)).

In some embodiments, the antibody of the ADC in the present invention (e.g., the transglutaminase-mediated higher loaded ADCs) further comprises a second amino acid modification at positions K222, K340, and/or K370 (e.g., K222R, K340R, and/or K370R).

In some embodiments, the amine donor agent (X—Y—Z) of the ADC is site-specifically conjugated to the glutamine-containing tag at least one or more positions selecting from the group consisting of 1) carboxyl terminus of any of a light chain, a heavy chain, or both the light chain and the heavy chain; 2) amino terminus of any of a light chain, a heavy chain, or both the light chain and the heavy chain; and 3) S60-R61, R108, T135, S160, S168, S190-S192, P189-S192, G200-S202, K222-T225, K222-T223, T223, L251-S254, M252-I253, E294-N297, E293-N297, N297, and/or G385 (e.g., as listed in Table 1), wherein the glutamine-containing tag is inserted in the antibody or replaces one or more endogenous amino acid in the antibody.

In some embodiments, the ADC of the present invention comprises a) amino acid substitutions at positions N297Q and K222R, wherein the amine donor agent (X—Y—Z) is site-specifically conjugated to the endogenous glutamine at position 295 and the substituted glutamine at position 297; and b) one or more glutamine-containing tags, wherein the amine donor agent is site-specifically conjugated to the glutamine-containing tag(s) at a carboxyl terminus of a light chain of the antibody, and wherein the drug-antibody ratio is about 5-7. In some embodiments, the amine donor agent is further site-specifically conjugated to the glutamine-containing tag at one or more positions selecting from the group consisting of S60-R61, R108, T135, S160, S168, S190-S192, P189-S192, G200-S202, K222-T225, K222-T223, T223, L251-S254, M252-I253, E294-N297, E293-N297, N297, and G385 (e.g., as listed in Table 1), wherein the glutamine-containing tag is inserted in the antibody or replaces one or more endogenous amino acid in the antibody, and wherein the drug-antibody ratio is at least about 6. For example, in some embodiments, the amine donor agent is further site-specifically conjugated to the glutamine-containing tag inserted after amino acid position T135 in the antibody heavy chain, and wherein the drug-antibody ratio is about 6-9. In other embodiments, the amine donor agent is further site-specifically conjugated to the glutamine-containing tag at amino acid positions G200-S202 in the antibody light chain, wherein the endogenous amino acid residues are replaced with the glutamine-containing tag, and wherein the drug-antibody ratio is about 6-11.

In some embodiments, the ADC of the present invention comprises an amine donor agent site-specifically conjugated to the glutamine-containing tag a) at a carboxyl terminus of a light chain of the antibody; b) after amino acid position T135 in the antibody heavy chain; and c) at amino acid positions G200-S202 in the antibody light chain, wherein the endogenous amino acid residues are replaced with the glutamine-containing tag, and wherein the drug-antibody ratio is about 5-7.

In some embodiments, the amine donor agent (X—Y—Z) is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly (acetyl-lysine-glycine)-MMAD, amino-PEG3-C2-MMAD, amino-PEG6-C2-MMAD, amino-PEG3-C2-amino-nonanoyl-MMAD, aminocaproyl-Val-Cit-PABC-MMAD, amino-PEG3-C2-Val-Cit-PABC-MMAD, amino-PEG6-C2-Val-Cit-PABC-MMAD, Ac-Lys-Val-Cit-PABC (acetyl-lysine-valine-citrulline-p-aminobenzyloxycarbonyl)-MMAD, aminocaproyl-MMAD, Ac-Lys-β-Ala-MMAD, amino-PEG2-C2-MMAE, aminocaproyl-MMAE, amino-PEG3-C2-MMAE, aminocaproyl-MMAF, aminocaproyl-Val-Cit-PABC-MMAE, amino-PEG-6-C2-Val-Cit-PABC-M MAE, Ac-Lys-Val-Cit-PABC-MMAE, aminocaproyl-Val-Cit-PABC-MMAF, amino-PEG-6-C2-Val-Cit-PABC-MMAF, Ac-Lys-Val-Cit-PABC-MMAF, amino-PEG6-C2-Val-Cit-PABC-0101, Ac-Lys-Val-Cit-PABC-0101, putrescinyl-geldanamycin, Ac-Lys-putrescinyl-geldanamycin, aminocaproyl-3377, amino-PEG6-C2-3377, aminocaproyl-0131, amino-PEG6-C2-0131, [(3R,5R)-1-{3-[2-(2-aminoethoxy)ethoxy]propanoyl}piperidine-3,5-diyl]bis-Val-Cit-PABC-MMAD, [(3R,5R)-1-{3-[2-(2-aminoethoxy)ethoxy]propanoyl}piperidine-3,5-diyl]bis-Val-Cit-PABC-MMAE, 2-aminoethoxy-PEG6-NODAGA, and N-2-acetyl-L-lysyl-L-valyl-N~5~-carbamoyl-N-[4-({[(2-{[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide. In some embodiments, the amine donor agent is a biocompatible polymer comprising a reactive amine and an agent moiety.

In some embodiments, the amine donor unit-linker (X—Y) is linear or branched. In some embodiments, the X—Y is selected from the group consisting of Ac-Lys-Gly, aminocaproic acid, Ac-Lys-β-Ala, amino-PEG2-C2, amino-PEG3-C2, amino-PEG6-C2, Ac-Lys-Val-Cit-PABC, amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine.

In some embodiment, the agent moiety (Z) is a cytotoxic agent selected from the group consisting of an anthracycline, an auristatin, a camptothecin, a combretastatin, a dolastatin, a duocarmycin, an enediyne, a geldanamycin, an indolinobenzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, isosteres, analogs, or derivatives thereof.

In another aspect, the invention provides a pharmaceutical composition comprising a plurality of higher loaded ADCs as described herein, wherein an average drug-antibody ratio is at least about 5.0. In one variation, provided is a pharmaceutical composition comprising a plurality of ADCs, wherein at least one ADC is the higher loaded ADC as described herein, and wherein an average drug-antibody ratio is at least about 4.1. In another variation, the invention provides a pharmaceutical composition comprising the higher loaded ADC as described herein, and a pharmaceutically acceptable excipient.

In another aspect, the invention provides a method for preparing the ADC as described herein, comprising the steps of: a) providing an antibody-T molecule comprising the antibody and the glutamine-containing tag; the antibody with the endogenous glutamine; and/or the antibody with the reactive endogenous glutamine; b) contacting the amine donor agent comprising the amine donor unit, linker, and agent moiety (X—Y—Z) with the antibody-T molecule in the presence of a transglutaminase; and c) allowing the antibody-T to covalently link to the amine donor agent to form the antibody-drug conjugate. In some embodiments, the conjugate has conjugation efficiency of at least about 51%.

In some embodiment, the methods provided herein further comprise a purification step, wherein the ADC is purified by a chromatography step.

In some embodiments, the transglutaminase is a microbial, purified, or engineered transglutaminase.

In another aspect, the invention provides a method of treating a cancer in a subject in need thereof, comprising administering to the subject an effective amount of a pharmaceutical composition comprising the ADC as described herein.

In another aspect, the invention provides a method of inhibiting tumor growth or progression in a subject in need thereof, comprising administering to the subject an effective amount of a pharmaceutical composition comprising the ADC as described herein.

In another aspect, the invention provides a method of diagnosing cancer in a subject suspected of suffering from cancer, comprising a) contacting a sample of the subject with the ADC as described herein under conditions that result in binding of the ADC with a cancer-related protein, and b) determining binding of the ADC to the cancer-related protein.

In some embodiments, the antibody in the ADC as described herein is a monoclonal antibody, a polyclonal antibody, a human antibody, a humanized antibody, a chimeric antibody, a bispecific antibody, a minibody, a diabody, or an antibody fragment.

In some embodiments, the glutamine-containing tag in the ADC as described herein comprises an amino acid sequence selected from the group consisting of Q, LQG, LLQGG (SEQ ID NO:1), LLQG (SEQ ID NO:2), LSLSQG (SEQ ID NO:3), GGGLLQGG (SEQ ID NO:4), GLLQG (SEQ ID NO:5), LLQ, GSPLAQSHGG (SEQ ID NO:6), GLLQGGG (SEQ ID NO:7), GLLQGG (SEQ ID NO:8), GLLQ (SEQ ID NO:9), LLQLLQGA (SEQ ID NO:10), LLQGA (SEQ ID NO:11), LLQYQGA (SEQ ID NO:12), LLQGSG (SEQ ID NO:13), LLQYQG (SEQ ID NO:14), LLQLLQG (SEQ ID NO:15), SLLQG (SEQ ID NO:16), LLQLQ (SEQ ID NO:17), LLQLLQ (SEQ ID NO:18), LLQGR (SEQ ID NO:19), LLQGPP (SEQ ID NO:20), LLQGPA (SEQ ID NO:21), GGLLQGPP (SEQ ID NO:22), GGLLQGA (SEQ ID NO:23), LLQGPGK (SEQ ID NO:25), LLQGPG (SEQ ID NO:26), LLQGP (SEQ ID NO:27), LLQP (SEQ ID NO:28), LLQPGK (SEQ ID NO:29), LLQAPGK (SEQ ID NO:30), LLQGAPG (SEQ ID NO:31), LLQGAP (SEQ ID NO:32), and LLQLQG (SEQ ID NO:36).

BRIEF DESCRIPTION OF THE DRAWINGS

FIG. 1 shows the cytotoxicity of site-specific ADCs with increasing DARs in the high target expressing BxPC3 cells in comparison to the conventionally conjugated ADC with a DAR 7.2. m7E6 is an anti-Trop2 (Trophoblast cell-surface antigen 2, also known as M1S1, GA733-1, EGP-1, or TACSTD2) antibody, H7c, L11b, TG6, and LCQ04 represent the glutamine-containing transglutaminase tag and the location of such tag in the antibody (see Table 1); N297Q represents amino acid substitution from N to Q at position 297 of the Trop2 antibody; and K222R represents amino acid substitution from K to R at position 222 of the Trop2 antibody; maleimido represents a conventional conjugation method through cysteine conjugation. These abbreviations apply to all other figures described herein.

FIG. 2 shows the cytotoxicity of the site-specific ADCs with increasing DARs in the medium target expressing Colo205 cells in comparison to the conventionally conjugated ADC with a DAR 7.2.

FIG. 3 shows the cytotoxicity of the site-specific ADCs with increasing DARs in the low target expressing CF-PAC1 cells in comparison to the conventionally conjugated ADC with a DAR 7.2.

FIG. 4 shows the non-specific cytotoxicity of the site-specific ADCs with increasing DARs in the SW620 cells with no target expression in comparison to the conventionally conjugated ADC with a DAR 7.2.

FIG. 5 shows the cytotoxicity of higher loaded site-specific ADCs of the present invention in the Colo205 cells with moderate expression of the target in comparison to the conventionally conjugated ADCs with similar DARs.

FIG. 7 also shows the efficacy of the higher-loaded site-specific ADCs of the present invention in inducing long term tumor stasis in the Colo 205 Xenograft Model in comparison to the conventionally conjugated ADCs with similar DARs.

FIG. 10(a) shows the ADC toxicokinetics of conventionally conjugated ADC with a DAR 7.8 and site-specific ADC with a DAR 7.76 dosed at 200 mg/kg. FIG. 10(b) shows body weight gain of mice dosed at 200 mg/kg with high loaded site-specific ADCs with a DAR 5.85 and with a DAR 7.71, and a conventionally conjugated ADC with a DAR 7.8. FIGS. 10(c) and 10(d) show liver enzymes activity and clinical pathology parameters from samples obtained on day 14 from mice dosed at 200 mg/kg with high loaded site-specific (SS) ADCs "DAR6" (m7E6 N297Q/K222R/LCQ04 amino-PEG6-C2-MMAD; DAR 5.85), and SS "DAR8" (m7E6 N297Q/K222R/LCQ04/H7c amino-PEG6-C2-MMAD; DAR 7.76), and conventional ADC "Cys DAR8" (m7E6 maleimido PEG6-C2-MMAD; DAR 7.8). AP, AST, and ALT represent aspartate aminotransferase, alanine transaminase, and alkaline phosphatase, respectively.

FIG. 15 also shows the cytotoxicity of the site-specific ADCs with increasing DARs in the moderate target expressing Colo205 cells in comparison to the site-specific ADCs with a lower DAR (e.g., 1.96 and 3.9).

FIG. 16 also shows the cytotoxicity of the site-specific ADCs with increasing DARs in the low target expressing CF-PAC1 cells in comparison to the site-specific ADCs with a lower DAR (e.g., 1.96 and 3.9).

DETAILED DESCRIPTION

Figure 6:
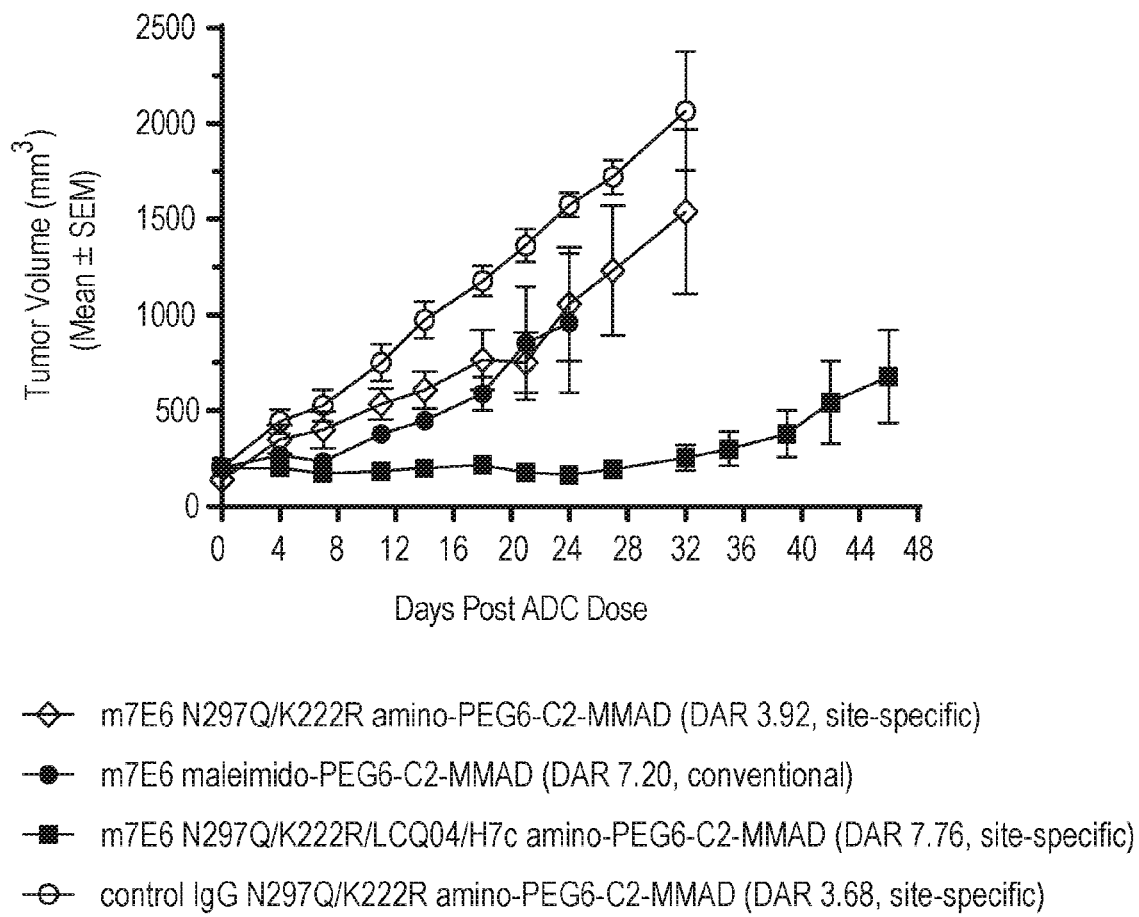
FIG. 6 shows the efficacy of the higher loaded site-specific ADCs of the present invention in inducing long term tumor stasis in the Colo205 Xenograft Model in comparison to the conventionally conjugated ADC with a DAR 7.2.

The present invention relates generally to transglutaminase-mediated site-specific antibody-drug conjugates (ADCs) with high drug-antibody ratio (DAR) comprising 1) glutamine-containing tags, endogenous glutamines (i.e., native glutamines without engineering, such as glutamines in variable domains, CDRs, etc.), and/or endogenous glutamines made reactive by antibody engineering or an engineered transglutaminase; and 2) amine donor agents comprising amine donor units, linkers, and agent moieties, wherein the DAR is at least about 5. Antibody-drug conjugates utilizing the conventional maleimide linkage with DARs of two to four have previously been found to be superior to their higher loaded counterparts in terms of in vivo efficacy, tolerability, and pharmacokinetics resulting in higher therapeutic index. Described here are higher loaded site-specific ADCs (e.g., DAR at least 5 or higher) having higher potency in vivo and less in vitro non-specific cytotoxicity in comparison to the conventional higher loaded ADCs. A single dose of a higher loaded site-specific ADC disclosed herein significantly outperformed the conventional ADCs with similar DARs in terms of long term tumor growth stasis. Furthermore, these higher loaded site-specific ADCs have similar pharmacokinetic profiles as the unconjugated wild-type antibody in mice and improved PK profile over the conventional higher loaded ADCs with a similar DAR in rat. These higher loaded site-specific ADCs also maintain a comparable safety profile relative to conventional ADCs with equivalent drug loading.

Accordingly, higher loaded site-specific ADCs are provided, each ADC comprising the formula: antibody-(T-(X—Y—$Z_a)_b)_c$, wherein: T is 1) a glutamine-containing tag engineered at a specific site, 2) an endogenous glutamine, and/or 3) an endogenous glutamine made reactive by antibody engineering or an engineered transglutaminase; X is an amine donor unit; Y is a linker; and Z is an agent moiety; X—Y—Z is an amine donor agent site-specifically conjugated to the glutamine-containing tag, the endogenous glutamine, and/or the reactive endogenous glutamine; a is an integer from 1 to 6; b is an integer from 1 to 6; c is an integer from 1 to 20; and wherein the product (drug-antibody ratio) of a, b, and c is at least about 5.

Also provided are methods of treating a cancer, inhibiting tumor growth or progression, inhibiting metastasis of cancer cells or tumors, or inducing tumor regression in a subject in need thereof, comprising administering to the subject an effective amount of the pharmaceutical composition comprising the ADCs as described herein.

Also provided are methods for preparing the ADC as described herein, comprising the steps of: a) providing an antibody-T molecule comprising the antibody and the glutamine-containing tag; and/or the antibody with the endogenous and/or reactive endogenous glutamine; b) contacting the amine donor agent with the antibody-T molecule in the presence of a transglutaminase; and c) allowing the antibody-T to covalently link to the amine donor agent to form the ADC. In some embodiments, the transglutaminase is an engineered transglutaminase.

GENERAL TECHNIQUES AND DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

The term "glutamine-containing tag", "glutamine tag," "Q-containing tag", "Q-tag", or "transglutaminase tag," as used herein refers to a polypeptide or a protein containing one or more Gln residue(s) that acts as an amine acceptor or acyl donor in the transglutaminase reaction.

The term "amine donor agent" or "acyl acceptor" as used herein refers to an agent containing one or more reactive amines (e.g., primary amines). For example, the amine donor agent can comprise an amine donor unit (e.g., primary amine $NH_2$), a linker (e.g., a molecule that is linked to an amine donor unit and contains additional functionality for attachment to a payload such as a small molecule, a polypeptide, or a biocompatible polymer), and an agent moiety (e.g., a payload such as a small molecule). The amine donor agent can also be a polypeptide (e.g., an antibody) or a biocompatible polymer containing one or more reactive lysine, N-termini, or reactive amines.

As used herein, the term "site specificity," "site-specifically conjugated," or "site-specifically crosslinked" refers to the specific conjugation or crosslinking of the amine donor agent to the antibody at a specific site (e.g., at various positions listed in Table 1) via a glutamine-containing tag, endogenous glutamine, and/or an endogenous glutamine made reactive by the antibody engineering or an engineered transglutaminase. Site specificity can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS-MS), and time-of-flight mass spectrometry (TOF-MS), hydrophobic interaction chromatography, ion exchange chromatography, site-directed mutagenesis, fluorescence-labeling, size exclusion chromatography, and X-ray crystallography.

As used herein, the term "an endogenous glutamine (Q) made reactive" refers to an endogenous glutamine that has been made accessible, exposed, or reactive to the amine donor agent in the presence of a transglutaminase by antibody engineering (e.g., enzymatic deglycosylation and/or amino acid modification) or by an engineered transglutaminase.

As used herein, the term "biocompatible polymer" refers to a polymer (e.g., repeating monomeric or structural units) that is suitable for therapeutic or medical treatment in a recipient (e.g., human) without eliciting any undesirable local or systemic effects in the recipient. A biocompatible polymer (synthetic, recombinant, or native) can be a water soluble or water insoluble polymer. A biocompatible polymer can also be a linear or a branched polymer.

As used herein, the term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies (e.g., COVX-BODY™), multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. On one aspect, the immunoglobulin is a human, murine, monkey, or rabbit immunoglobulin.

The term "Fab containing polypeptide" as used herein refers to a polypeptide comprising a Fab fragment, Fab' fragment, or "(Fab')2 fragment." A Fab-containing polypeptide may comprise part or all of a wild-type hinge sequence (generally at the carboxyl terminus of the Fab portion of the polypeptide). A Fab-containing polypeptide may be obtained or derived from any suitable immunoglobulin, such as from at least one of the various IgG1, IgG2, IgG3, or IgG4 subtypes, or from IgA, IgE, IgD or IgM. A Fab-containing polypeptide may be a Fab-containing fusion polypeptide, wherein one or more polypeptides are linked to a Fab-containing polypeptide. A Fab fusion combines the Fab polypeptide of an immunoglobulin with a fusion partner, which in general may be any protein, polypeptide, or small molecule. Virtually any protein or small molecule may be linked to the Fab polypeptide to generate a Fab-containing fusion polypeptide. Fab-containing fusion partners may include, but are not limited to, the target-binding region of a receptor, an adhesion molecule, a ligand, an enzyme, a cytokine, a chemokine, or some other protein or protein domain.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

"Antibody fragments" as used herein comprise only a portion of an intact antibody, wherein the portion preferably retains at least one, preferably most or all, of the functions normally associated with that portion when present in an intact antibody.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas, linking of Fab' fragments, or mutations at the antibody hinge and CH3 domains. See, e.g., Songsivilai & Lachmann, *Clin. Exp. Immunol.* 79:315-321 (1990); Kostelny et al., *J. Immunol.* 148:1547-1553 (1992); and Strop et al., *J. Mol. Biol.* 420(3):204-219 (2012). The two binding sites of a bispecific antibody will bind to two different epitopes, which may reside on the same or different protein targets.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-15 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

The "hinge region," "hinge sequence," and variation thereof, as used herein, includes the meaning known in the art, which is illustrated, for example, Janeway et al., ImmunoBiology: the immune system in health and disease, (Elsevier Science Ltd., NY) (4$^{th}$ ed., 1999); Bloom et al., Protein Science (1997), 6:407-415; Humphreys et al., *J. Immunol. Methods* (1997), 209:193-202.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at amino terminus of the Fc-containing polypeptide). An Fc-containing polypeptide may also be a dimer. An Fc-containing polypeptide may be obtained or derived from any suitable immunoglobulin, such as from at least one of the various IgG1, IgG2, IgG3, or IgG4 subtypes, or from IgA, IgE, IgD or IgM. Although the boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991.

An Fc-containing polypeptide may be an Fc-containing fusion polypeptide, wherein one or more polypeptides are linked to an Fc-containing polypeptide. An Fc fusion combines the Fc polypeptide of an immunoglobulin with a fusion partner, which in general may be any protein, polypeptide, or small molecule. Virtually any protein or small molecule may be linked to the Fc region to generate an Fc-containing fusion polypeptide. Fc-containing fusion partners may include, but are not limited to, the target-binding region of a receptor, an adhesion molecule, a ligand, an enzyme, a cytokine, a chemokine, or some other protein or protein domain.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains (i.e., Fc domain). Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

The terms "polypeptide", "oligopeptide", "peptide" and "protein" are used interchangeably herein to refer to chains of amino acids of any length, preferably relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As used herein, the term "wild-type amino acid," "wild-type IgG," or "wild-type mAb" refers to a sequence of amino acids or nucleic acids that occurs naturally within a certain population (e.g., human, mice, rats, cells, etc.).

As used herein, the term "conjugation efficiency" or "crosslinking efficiency" is the ratio between the experimentally measured amounts of the ADC as described herein divided by the maximum expected ADC amount. Conjugation efficiency or crosslinking efficiency can be measured by various techniques well known to persons skilled in the art, such as hydrophobic interaction chromatography. Conjugation efficiency can also be measured at different temperature, such as room temperature or 37° C.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; de Haas et al., 1995, *J. Lab. Clin. Med.*, 126:330-41; Nimmerjahn et al., 2005, *Immunity* 23:2-4. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, cancer remission, decreasing cancer symptoms, increasing the quality of life of those suffering from cancer, decreasing the dose of other medications required to treat cancer, delaying the progression of cancer, curing cancer, and/or prolong survival of a cancer patients.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various cancer-related diseases or conditions (such as gastric, head and neck, lung, ovarian, and pancreatic cancers), decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

The term "purify," and grammatical variations thereof, is used to mean the removal, whether completely or partially, of at least one impurity from a mixture containing the ADC and one or more impurities, which thereby improves the level of purity of the ADC in the composition (i.e., by decreasing the amount (ppm) of impurity(ies) in the composition).

Reference to "about" a value or parameter herein includes (and describes) embodiments that are directed to that value or parameter per se. For example, description referring to "about X" includes description of "X." Numeric ranges are inclusive of the numbers defining the range.

An "individual" or a "subject" is a mammal, more preferably, a human. Mammals also include, but are not limited to, farm animals, sport animals, pets, primates, horses, dogs, cats, mice, and rats.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

The residue designations in this application are based on the EU numbering scheme of the constant domain (Edelman et al., *Proc. Natl. Acad. Sci. USA*, 63(1):78-85 (1969).

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting Antibody-Drug Conjugates with High Drug Loading The antibody-drug conjugates herein comprise an antibody site-specifically conjugated to an amine donor agent (e.g., a small molecule coupled to a linker with an amine donor unit) via an engineered glutamine-containing tag, an endogenous glutamine (i.e., native glutamines without engineering, such as glutamines in the variable domains, CDRs, etc.), and/or a reactive endogenous glutamine, wherein the drug-antibody ratio (DAR) is at least about 5 (e.g., at least 5 drugs/payloads per antibody). The endogenous glutamine can be made reactive (i.e., the ability to form a covalent bond as an acyl donor in the presence of an amine and a transglutaminase) by modifying one or more amino acid(s) (e.g., amino acid deletion, insertion, substitution, or mutation) in the antibody, by enzymatic deglycosylation, or by reacting with an engineered transglutaminase. Accordingly, in one aspect, provided is an antibody-drug conjugate (ADC) comprising the formula: antibody-(T-(X—Y—$Z_a$)$_b$)$_c$, wherein: T is 1) a glutamine-containing tag engineered at a specific site, 2) an endogenous glutamine, and/or 3) an endogenous glutamine made reactive by antibody engineering or an engineered transglutaminase; X is an amine donor unit; Y is a linker; and Z is an agent moiety; X—Y—Z is an amine donor agent site-specifically conjugated to the glutamine-containing tag, the endogenous glutamine, and/or the reactive endogenous glutamine; a is an integer from 1 to 6; b is an integer from 1 to 6; c is an integer from 1 to 20; and wherein the product (drug-antibody ratio) of a, b, and c is at least about 5. Both the glutamine-containing tag, the endogenous glutamine, and/or the reactive glutamine on the antibody, and the amine donor agent (X—Y—Z) described herein, are substrates for transglutaminase, and the linkage between the glutamine-containing tag and/or the endogenous/reactive glutamine, and the amine donor agent, is of the formula $CH_2$—$CH_2$—CO—NH—, wherein NH— is linked to a linker and an agent moiety.

Transglutaminases are protein-glutamine γ-glutamyl-transferases (EC 2.3.2.13), which typically catalyze pH-dependent transamidation of glutamine residues with lysine residues. The transglutaminase used in the invention described herein can be obtained or made from a variety of sources, or engineered to catalyze transamidation of one or more endogenous glutamine residues with one or more lysine residues or amine donor agents containing one or more reactive amines. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the mTGase polypeptide is derived from a fungal protein (e.g., *Oomycetes, Actinomycetes, Saccharomyces, Candida, Cryptococcus, Monascus*, or *Rhizopus* transglutaminases). In some embodiments, the mTGase polypeptide is derived from Myxomycetes (e.g., *Physarum polycephalum* transglutaminase). In some embodiments, the mTGase polypeptide is derived from a bacterial protein, such as transglutaminase from *Streptoverticillium* sp. or *Streptomyces* sp. (e.g., *Streptomyces mobarensis* or *Streptoverticillium mobarensis*). In some embodiments, the mTGase polypeptide is derived from a bacterial protein, such as transglutaminase from, but not limited to, *Streptoverticillium mobarensis, Streptoverticillium griseocarneum, Streptoverticillium ladakanum, Streptomyces mobarensis, Streptomyces viridis, Streptomyces ladakanum, Streptomyces caniferus, Streptomyces platensis, Streptomyces hygroscopius, Streptomyces netropsis, Streptomyces fradiae, Streptomyces roseovertivillatus, Streptomyces cinnamaoneous, Streptomyces griseocarneum, Streptomyces lavendulae, Streptomyces lividans, Streptomyces lydicus, Streptomyces sioyansis, Actinomadura* sp., *Bacillus* (e.g., *Bacillus circulans, Bacillus subtilis*, etc.), *Corynebacterium ammoniagenes, Corynebacterium glutamicum, Clostridium, Enterobacter* sp., *Micrococcus, Providencia* sp., or isolates thereof. In some embodiments, the transglutaminase is a calcium independent transglutaminase which does not require calcium to induce enzyme conformational changes and allow enzyme activity. In some embodiments, the mTGase polypeptide is derived from *S. mobarensis*. Commercially available calcium independent transglutaminase such as ACTIVA™ (Ajinomoto, Japan) is also suitable for the present invention.

In some embodiments, the transglutaminase used in the invention described herein is an engineered transglutaminase which catalyzes transamidation of one or more endogenous glutamine residues in the antibody with one or more lysine residues or reactive amines in the amine donor agent. For example, one or more wild-type amino acid residues in the naturally occurring transglutaminase can be deleted, or replaced or substituted with another amino acid residue(s) to make the engineered transglutaminase.

In some embodiments, the transglutaminase used in the invention described herein can also be a recombinant protein produced using recombinant techniques known to persons skilled in the art. In some embodiments, the transglutaminase used in the invention described herein can be a purified protein. For example, the purified transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is about any of 50%, 55%, 60%, 65%, 70%, 75%, 80%, 85%, 90%, 95%, 96%, 97%, 98%, 99%, or 100% pure.

In some embodiments, the glutamine-containing tag of the ADC as described herein is not spatially adjacent to a reactive Lys in the antibody. For example, the glutamine-containing tag is not spatially adjacent to a reactive Lys in the carboxyl terminus, the amino terminus, or both the carboxyl and the amino termini of the polypeptide.

In some embodiments, the ADC of the present invention comprises at least 1 endogenous glutamine made reactive in a transamidation reaction by antibody engineering or by an engineered transglutaminase. In some embodiments, the antibody engineering is antibody deglycosylation (e.g., enzymatic deglycosylation); or amino acid modification including amino acid deletion, insertion, substitution, mutation, or any combination thereof on the antibody. For example, the wild-type amino acid Asn (N) at position 297 in an antibody is substituted or replaced with amino acid Ala (A), resulting in aglycosylation at position 297 and reactive endogenous glutamine (Q) at position 295. In another example, the amino acid modification in the antibody is an amino acid substitution from N to Q at position 297, resulting in aglycosylation at position 297, reactive endogenous Q at position 295, and site-specific conjugation between the N297Q and Q295 and one or more amine donor agents at these two sites in the presence of a transglutaminase.

In some embodiments, the ADC of the present invention comprises a glutamine-containing tag engineered at at least one or more positions including, but not limited to, 1) carboxyl terminus of any of a light chain, a heavy chain, or both the light chain and the heavy chain; 2) amino terminus of any of a light chain, a heavy chain, or both the light chain and the heavy chain; and 3) S60-R61, R108, T135, S160, S168, S190-S192, P189-S192, G200-S202, K222-T225, K222-T223, T223, L251-S254, M252-I253, E294-N297, E293-N297, N297, and/or G385, wherein the glutamine-containing tag is inserted in the antibody or replaces one or more endogenous amino acid in the antibody, wherein the drug-antibody ratio is at least about 5. Examples of the specific glutamine-containing tag and corresponding engineered position are provided in Table 1. Accordingly, in some embodiments, the ADC of the present invention comprises a DAR of at least about 5 (e.g., 5 drugs/payloads per antibody) and a glutamine-containing tag engineered at any one or more of the positions as listed in Table 1.

TABLE 1

| Glutamine-containing Tag Name | Sequence | Amino Acid Positions |
|---|---|---|
| TG6 | LLQGA (SEQ ID NO: 11) | C-terminus of the antibody heavy chain (e.g., K447) |
| LCQ04 | GGLLQGA (SEQ ID NO: 23) | C-terminus of the antibody light chain |
| LCQ05 | GGLLQGPP (SEQ ID NO: 22) | C-terminus of the antibody light chain |
| H7c | LLQG (SEQ ID NO: 2) | Insertion after residue T135 in the antibody heavy chain |
| L11b | LLQG (SEQ ID NO: 2) | Replacement of residues G200-S202 with the glutamine-containing tag in the antibody light chain |
| H1 | LLQGSG (SEQ ID NO: 13) | N-terminus |
| H8a | LLQG (SEQ ID NO: 2) | Insertion after residue S160 in the antibody heavy chain |
| H10 | LLQG (SEQ ID NO: 2) | Replacement of residues S190-S192 with the glutamine-containing tag in the antibody heavy chain |
| H10a | LLQYQG (SEQ ID NO: 14) | Replacement of residues P189-S192 with the glutamine-containing tag in the antibody heavy chain |
| H10b | LLQLLQG (SEQ ID NO: 15) | Replacement of residues P189-S192 with the glutamine-containing tag in the antibody heavy chain |

TABLE 1-continued

| Glutamine-containing Tag Name | Sequence | Amino Acid Positions |
|---|---|---|
| H12 | LLQG (SEQ ID NO: 2) | Replacement of residues K222-T225 with the glutamine-containing tag in the antibody heavy chain |
| H12c | LLQG (SEQ ID NO: 2) | Replacement of residues K222-T223 with the glutamine-containing tag in the antibody heavy chain |
| H12d | LLQG (SEQ ID NO: 2) | Insertion after residue T223 in the antibody heavy chain |
| H13a | SLLQG (SEQ ID NO: 16) | Replacement of residues L251-S254 with the glutamine-containing tag in the antibody heavy chain |
| H13b | LQG | Replacement of residues M252-I253 with the glutamine-containing tag in the antibody heavy chain |
| H16 | LLQG (SEQ ID NO: 2) | Replacement of residues E294-N297 with the glutamine-containing tag in the antibody heavy chain |
| H16a | LLQLQG (SEQ ID NO: 36) | Replacement of residues E293-N297 with the glutamine-containing tag in the antibody heavy chain |
| H16b | LLQLLQG (SEQ ID NO: 15) | Replacement of residues E293-N297 with the glutamine-containing tag in the antibody heavy chain |
| H16c | LLQLQ (SEQ ID NO: 17) | Replacement of residues E294-N297 with the glutamine-containing tag in the antibody heavy chain |
| H16d | LLQLLQ (SEQ ID NO: 18) | Replacement of residues E294-N297 with the glutamine-containing tag in the antibody heavy chain |
| N297Q | Q | Replacement of residue N297 with the glutamine-containing tag in the antibody |
| N297A | A | Replacement of residue N297 with amino acid A, resulting in aglycosylation at position 297 and accessible/reactive endogenous glutamine at position 295 |
| H21a | LLQG (SEQ ID NO: 2) | Insertion after residue G385 in the antibody heavy chain |
| L2 | LLQG (SEQ ID NO: 2) | Replacement of residues S60-R61 with the glutamine-containing tag in the antibody light chain |
| L4b | LLQG (SEQ ID NO: 2) | Insertion after residue R108 in the antibody light chain |
| L8a | LLQG (SEQ ID NO: 2) | Insertion after residue S168 in the antibody light chain |

TABLE 1-continued

| Glutamine-containing Tag Name | Sequence | Amino Acid Positions |
|---|---|---|
| L11b | LLQG (SEQ ID NO: 2) | Replacement of residues G200-S202 with the glutamine-containing tag in the antibody light chain |
| L11c | LLQGR (SEQ ID NO: 19) | Replacement of residues G200-S202 with the glutamine-containing tag in the antibody light chain |
| TG4 | LLQYQGA (SEQ ID NO: 12) | C-terminus of the antibody heavy chain (e.g., K447) |
| TG5 | LLQLLQGA (SEQ ID NO: 10) | C-terminus of the antibody heavy chain (e.g., K447) |
| TG17 | LLQGPP (SEQ ID NO: 20) | C-terminus of the antibody heavy chain (e.g., K447) |

In some embodiments, the antibody of the ADC of the present invention further comprises a second amino acid modification at position(s) 222, 340, and/or 370 (EU numbering) relative to the wild-type antibody at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the other (e.g., non-wild type) amino acid is Arg (e.g., K222R, K340R, or K370R). In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val.

Accordingly, in some embodiments, the ADC of the present invention comprises a) an amino acid substitutions at positions N297Q and K222R, wherein the amine donor agent is site-specifically conjugated to the endogenous glutamine at position 295 and the substituted glutamine at position 297; and b) one or more glutamine-containing tag(s), wherein the amine donor agent is site-specifically conjugated to the glutamine-containing tag(s) at a carboxyl terminus of a light chain of the antibody; and wherein the drug-antibody ratio (DAR) is about 5-7. In some embodiments, the glutamine-containing tag at the carboxyl terminus of the light chain of the antibody is GGLLQGA (SEQ ID NO: 23) or GGLLQGPP (SEQ ID NO: 22).

In some embodiments, the ADC of the present invention comprises a) an amino acid substitutions at positions N297Q and K222R, wherein the amine donor agent is site-specifically conjugated to the endogenous glutamine at position 295 and the substituted glutamine at position 297; b) one or more glutamine-containing tag(s), wherein the amine donor agent is site-specifically conjugated to the glutamine-containing tag(s) at a carboxyl terminus of a light chain of the antibody; c) one or more glutamine-containing tag(s), wherein the amine donor agent is further site-specifically conjugated to the glutamine-containing tag at one or more positions selected from the group consisting of S60-R61, R108, T135, S160, S168, S190-S192, P189-S192, G200-S202, K222-T225, K222-T223, T223, L251-S254, M252-I253, E294-N297, E293-N297, N297, and G385 in the antibody, wherein the glutamine-containing tag is inserted in the antibody or replaces one or more endogenous amino acid in the antibody; and wherein the drug-antibody ratio is at least about 6. For example, in some embodiments, the ADC of the present invention also comprises a) an amino acid substitutions at positions N297Q and K222R, wherein the amine donor agent is site-specifically conjugated to the endogenous glutamine at position 295 and the substituted glutamine at position 297; b) one or more glutamine-containing tag(s), wherein the amine donor agent is site-specifically conjugated to the glutamine-containing tag(s) at a carboxyl terminus of a light chain of the antibody; c) one or more glutamine tag(s), wherein the amine donor agent is further site-specifically conjugated to the glutamine-containing tag at a carboxyl terminus of a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23) or GGLLQGPP (SEQ ID NO: 22; and the glutamine-containing tag at the carboxyl terminus of the heavy chain of the antibody is LLQGA (SEQ ID NO: 11) or LLQGPP (SEQ ID NO: 20).

In one variation, the ADC of the present invention comprises a) an amino acid substitutions at positions N297Q and K222R, wherein the amine donor agent is site-specifically conjugated to the endogenous glutamine at position 295 and the substituted glutamine at position 297; b) one or more glutamine-containing tag(s), wherein the amine donor agent is site-specifically conjugated to the glutamine-containing tag(s) at a carboxyl terminus of a light chain of the antibody; c) one or more glutamine-containing tag(s), wherein the amine donor agent is further site-specifically conjugated to the glutamine-containing tag inserted after amino acid position T135 in a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23) or GGLLQGPP (SEQ ID NO: 22; and the glutamine-containing tag inserted after T135 in the heavy chain of the antibody is LLQG (SEQ ID NO: 2).

In another variation, the ADC of the present invention comprises a) an amino acid substitutions at positions N297Q and K222R, wherein the amine donor agent is site-specifically conjugated to the endogenous glutamine at position 295 and the substituted glutamine at position 297; b) one or more glutamine-containing tag(s), wherein the amine donor agent is site-specifically conjugated to the glutamine-containing tag(s) at a carboxyl terminus of a light chain of the antibody; c) one or more glutamine-containing tag(s), wherein the amine donor agent is further site-specifically conjugated to the glutamine-containing tag at amino acid positions G200-S202 in a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23) or GGLLQGPP (SEQ ID NO: 22); and the glutamine-containing tag at amino acid positions G200-S202 in the light chain of the antibody is LLQG (SEQ ID NO: 2).

In some embodiments, the ADC of the present invention also comprises a) an amino acid substitutions at positions N297Q and K222R, wherein the amine donor agent is site-specifically conjugated to the endogenous glutamine at position 295 and the substituted glutamine at position 297; b) one or more glutamine-containing tag(s), wherein the amine donor agent is site-specifically conjugated to the glutamine-containing tag(s) at a carboxyl terminus of a light chain of the antibody; c) one or more glutamine-containing tag(s), wherein the amine donor agent is further site-specifically conjugated to the glutamine-containing tag at amino acid positions G200-S202 in a light chain of the antibody; (d) one or more glutamine-containing tag(s), wherein the amine donor agent is further site-specifically conjugated to the glutamine-containing tag inserted after amino acid position T135 in a heavy chain of the antibody; and wherein the drug-antibody ratio (DAR) is about 9-11. In some embodiments, the glutamine-containing tag at the carboxyl terminus of the light chain of the antibody is GGLLQGA (SEQ ID NO: 23) or GGLLQGPP (SEQ ID NO: 22); the glutamine-containing tag at amino acid positions G200-S202 in the light chain of the antibody is LLQG (SEQ ID NO: 2); and the glutamine-containing tag inserted after T135 in the heavy chain of the antibody is also LLQG (SEQ ID NO: 2).

In some embodiments, the ADC of the present invention also comprises an amine donor agent site-specifically conjugated to the glutamine-containing tag a) at a carboxyl terminus of a light chain of the antibody; b) after amino acid position T135 in the antibody heavy chain; and c) at amino acid positions G200-S202 in the antibody light chain, wherein the endogenous amino acid residues are replaced with the glutamine-containing tag, and wherein the drug-antibody ratio is about 5-7. In some embodiments, the glutamine-containing tag at the carboxyl terminus of the light chain of the antibody is GGLLQGA (SEQ ID NO: 23) or GGLLQGPP (SEQ ID NO: 22); the glutamine-containing tag at amino acid positions G200-S202 in the light chain of the antibody is LLQG (SEQ ID NO: 2); and the glutamine-containing tag inserted after T135 in the heavy chain of the antibody is also LLQG (SEQ ID NO: 2).

The drug-antibody ratio (DAR) of the ADC of the present invention is about 5 to about 720. In some embodiments, the DAR is at least about any of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, 550, 600, 650, 700, and 710.

In some embodiments, the glutamine-containing tag for the ADC described herein comprises an amino acid sequence XXQX (SEQ ID NO:37), wherein X can be a conventional or nonconventional amino acid, as described herein. For example, in some embodiments, X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp). In some embodiments, the glutamine-containing tag comprises an amino acid sequence selected from the group consisting of Q, LQG, LLQGG (SEQ ID NO:1), LLQG (SEQ ID NO:2), LSLSQG (SEQ ID NO:3), GGGLLQGG (SEQ ID NO:4), GLLQG (SEQ ID NO:5), LLQ, GSPLAQSHGG (SEQ ID NO:6), GLLQGGG (SEQ ID NO:7), GLLQGG (SEQ ID NO:8), GLLQ (SEQ ID NO:9), LLQLLQGA (SEQ ID NO:10), LLQGA (SEQ ID NO:11), LLQYQGA (SEQ ID NO:12), LLQGSG (SEQ ID NO:13), LLQYQG (SEQ ID NO:14), LLQLLQG (SEQ ID NO:15), SLLQG (SEQ ID NO:16), LLQLQ (SEQ ID NO:17), LLQLLQ (SEQ ID NO:18), LLQGR (SEQ ID NO:19), LLQGPP (SEQ ID NO:20), LLQGPA (SEQ ID NO:21), GGLLQGPP (SEQ ID NO:22), GGLLQGA (SEQ ID NO:23), LLQGPGK (SEQ ID NO:25), LLQGPG (SEQ ID NO:26), LLQGP (SEQ ID NO:27), LLQP (SEQ ID NO:28), LLQPGK (SEQ ID NO:29), LLQAPGK (SEQ ID NO:30), LLQGAPG (SEQ ID NO:31), LLQGAP (SEQ ID NO:32), and LLQLQG (SEQ ID NO:36). In some embodiments, the glutamine-containing tag comprises an amino acid sequence LLQGA (SEQ ID NO:11), LQG, GGLLQGA (SEQ ID NO:23), LLQGPA (SEQ ID NO:21), LLQGPP (SEQ ID NO:20), GGLLQGPP (SEQ ID NO:22), LLQGSG (SEQ ID NO:13), LLQG (SEQ ID NO:2), LLQYQG (SEQ ID NO:14), LLQLLQG (SEQ ID NO:15), LLQLQG (SEQ ID NO:36), LLQLLQ (SEQ ID NO:18), LLQLQ (SEQ ID NO:17), LLQGR (SEQ ID NO:19), LLQYQGA (SEQ ID NO:12), SLLQG (SEQ ID NO:16), or LLQLLQGA (SEQ ID NO:10). In some embodiments, the acyl donor glutamine-containing tag does not comprise an amino acid sequence selected from the group consisting of LGGQGGG (SEQ ID NO:38), GGGQGGL (SEQ ID NO:39), GXGQGGG (SEQ ID NO:40), GGXQGGG (SEQ ID NO:41), GGGQXGG (SEQ ID NO:42), and GGGQGXG (SEQ ID NO:43), wherein X is G, A, S, L, V, F, Y, R, N, or E). Other exemplary tags are also described, for example, in US20130230543 and US2013/0122020.

In some embodiments, the antibody of the ADCs as described herein comprises an amino acid modification at the last amino acid position in the carboxyl terminus relative to a wild-type antibody at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the insertion comprises inserting one or more amino acid(s) (e.g., inserting one, two, three or more amino acids). In some embodiments, the other (e.g., non-wild type) or inserted amino acid is Arg. In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val. For example, in some embodiments, the last amino acid in the carboxyl terminus of the antibody (e.g., the heavy chain of an antibody) can be deleted, and the glutamine-containing tag engineered to the C-terminus of the polypeptide comprises the amino acid sequence LLQGA (SEQ ID NO:11) or LLQGPP (SEQ ID NO:20).

In some embodiments, the antibody comprises an amino acid modification at the first amino acid position in the amino terminus relative to a wild-type antibody at the same position. In some embodiments, the modification is an amino acid deletion, insertion, substitution, mutation, or any combination thereof. In some embodiments, the substitution comprises replacing a wild type amino acid with another (e.g., non-wild type) amino acid. In some embodiments, the insertion comprises inserting an amino acid. In some embodiments, the non-wild type or inserted amino acid is Arg. In some embodiments, the other (non-wild type or inserted) amino acid is Ala, Asn, Asp, Cys, Glu, Gln, Gly, His, Ile, Leu, Met, Phe, Pro, Ser, Thr, Trp, Tyr, or Val.

In some embodiments, the ADC described herein comprises a full length antibody heavy chain and an antibody light chain. In some embodiments, the antibody described herein is a monoclonal antibody, a polyclonal antibody, a human antibody, a humanized antibody, a chimeric antibody, a bispecific antibody, a minibody, a diabody, or an antibody fragment.

In some embodiments, the antibody is an IgG. In some embodiments, the IgG is selected from the group consisting of IgG1, IgG2, IgG3, and IgG4.

In some embodiments, the antibody is an IgA, IgE, IgD, or IgM.

In some embodiments, the effector function (e.g., as measured by Fcγ3 and/or C1q binding) of the ADCs described herein decreases no greater than about any of 1-fold, 2-fold, 3-fold, 4-fold, or 5-fold relative to a wild type antibody. In some embodiments, the antibody of the ADC is an IgG, wherein the effector function of the IgG decreases no greater than about 2-fold relative to a wild type IgG. In other embodiments, the effector function of the IgG decreases about 2-fold relative to a wild type IgG. In other embodiments, the effector function of the IgG decreases more than about 2-fold relative to a wild type IgG. In some embodiments, the antibody of the ADC is an IgG, wherein the effector function of the IgG decreases no greater than about 1-fold relative to a wild type IgG. In other embodiments, the effector function of the IgG decreases about 1-fold relative to a wild type IgG. In some embodiments, the effector function of the IgG decreases more than about any of 1-fold, 3-fold, 4-fold, or 5-fold relative to a wild type IgG.

In some embodiments, the effector function (e.g., as measured by Fcγ3 and/or C1q binding) of the ADC described herein increases at least about 1-fold to 3000-fold relative to a wild type antibody. In some embodiments, the effector function of the ADC increases at least about any of 1- to 5-fold, 6- to 10-fold, 11- to 15-fold, 16- to 20-fold, 21- to 25-fold, 26- to 30-fold, 31- to 35-fold, 36- to 40-fold, 41- to 45-fold, 46- to 50-fold, 51- to 55-fold, 56- to 60-fold, 61- to 65-fold, 66- to 70-fold, 71- to 75-fold, 76- to 80-fold, 81- to 85-fold, 86- to 90-fold, 91- to 95-fold, 96- to 100-fold, 101- to 200-fold, 201- to 300-fold, 301- to 500-fold, 501- to 1000-fold, 1001- to 1500-fold, 1501- to 2000-fold, 2001- to 2500-fold, 2501- to 3000-fold relative to a wild type antibody. In some embodiments, the antibody of the ADC is an IgG, wherein the effector function of the IgG increases about 1-fold to 300-fold relative to a wild type IgG. In some embodiments, the effector function of the IgG increases about any of 2-fold, 3-fold, 4-fold, 5-fold, 10-fold, 15-fold, 20-fold, 40-fold, 60-fold, 80-fold, 100-fold, 150-fold, 200-fold, 250-fold, 300-fold, 400-fold, 500-fold, 600-fold, 700-fold, 800-fold, 900-fold, 1000-fold, 1500-fold, 2000-fold, 2500-fold, or 3000-fold relative to a wild type IgG.

In some embodiments, the amine donor agent has the formula: X—Y—Z, wherein X is an amine donor unit; Y is a linker; and Z is an agent moiety.

The number of the amine donor agents which may be conjugated to the antibody is dependent on 1) the number of glutamine-containing tags which are linked/inserted to the antibody as well as the number of glutamines on the glutamine-containing tag; and/or 2) the number of endogenous glutamines on the antibody (i.e., native glutamines without engineering, such as glutamines in the variable domains, CDRs, etc.) and/or 3) the number of endogenous glutamines made reactive by the antibody engineering as described herein or an engineered transglutaminase. For example, two amine donor agents may be site-specifically conjugated to an antibody at the carboxyl termini of the two light chains, and four amine donor agents may be site-specifically conjugated to the antibody at positions Q295 and N297Q. In some embodiments, the amine donor agent can be the same or different at each conjugation position.

The amine donor unit of the present invention is a primary amine ($NH_2$) that provides a substrate for transglutaminase to allow conjugation of the agent moiety to the antibody via the glutamine-containing tag, the endogenous glutamine, and/or the reactive endogenous glutamine. Accordingly, the linkage between the glutamine-containing tag, the endogenous glutamine, and/or the reactive endogenous glutamine; and the amine donor unit is of the formula $CH_2$—$CH_2$—CO—NH—, wherein one NH— is linked to one linker and one or more agent moieties.

The linker of the present invention can be a cleavable or a non-cleavable linker. For example, the linker (with amine donor unit) or the amine donor agent can be released from the antibody. In some embodiments, the linker can be a peptide linker (e.g., conventional and/or nonconventional amino acid(s)) and/or a non-peptide linker. Examples of a non-peptide linker include an alkyl linker and a PEG (polyethylene glycol) linker.

In some embodiments, the amine donor unit-linker (e.g., X—Y) is a linear unit comprising an agent moiety. In other embodiments, the amine donor unit-linker is a branched unit (e.g., at least 2 units) comprising at least about 2, 3, 4, 5, 6, 7, 8, 9, 10, 11, 12, or more agent moieties. In one variation, the agent moiety on a branched linker can be the same or different agent moieties.

Exemplary amine donor unit-linkers include, but are not limited to, Ac-Lys-Gly, aminocaproic acid, Ac-Lys-β-Ala, amino-PEG2-C2, amino-PEG3-C2, amino-PEG6-C2, Ac-Lys-Val-Cit (citrulline)-PABC (p-aminobenzyloxycarbonyl), amino-PEG3-C2-Val-Cit-PABC, amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC-, Ac-Lys-putrescine, or 2-aminoethoxy.

The agent moiety of the engineered polypeptide of the present invention includes a small molecule, a protein or polypeptide, and a biocompatible polymer.

In some embodiments, a small molecule is a cytotoxic agent, an immunosuppressive agent, or an imaging agent (e.g., a fluorophore). In some embodiments, the cytotoxic agent is a chemotherapeutic agent.

Examples of a cytotoxic agent include, but are not limited to, anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof.

The anthracyclines are derived from bacteria Strepomyces and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

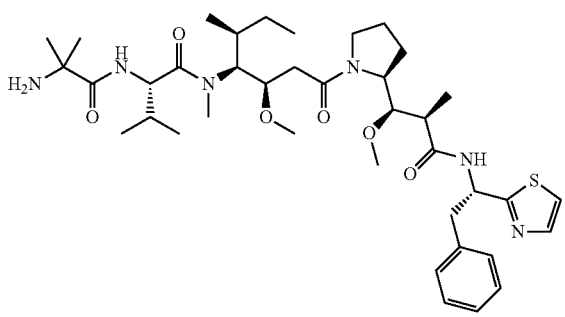

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide) having the following structure:

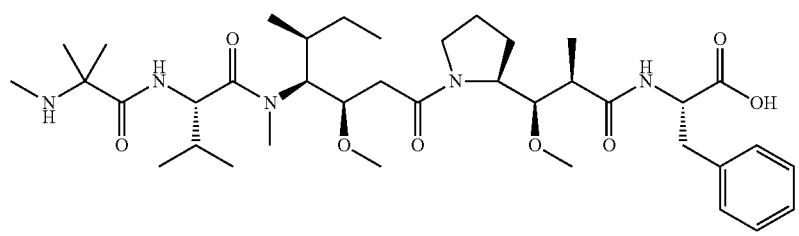 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In some embodiments, the auristatin is 3377-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide) having the following structure:

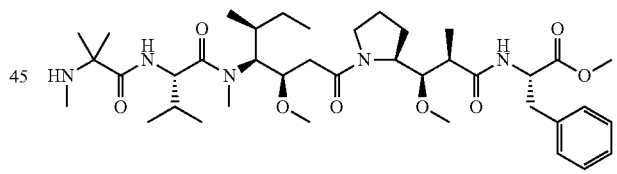

In other embodiments, the auristatin is 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

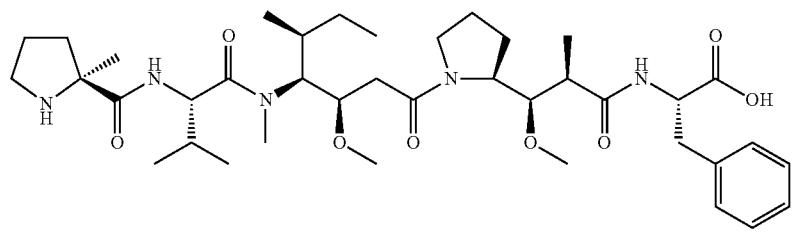

In other embodiments, the auristatin is 0121(2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

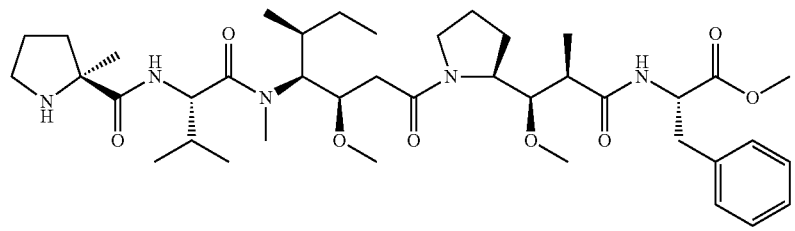 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycin and CC-1065 are DNA alkylating agents with cytotoxic potency. See Boger and Johnson, *PNAS* 92:3642-3649 (1995). Exemplary duocarmycin and CC-1065 include, but are not limited to, (+)-duocarmycin A and (+)-duocarmycin SA, (+)-CC-1065, and the compounds as disclosed in the international application PCT/IB2015/050280 including, but not limited to, N~2~-acetyl-L-lysyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide having the structure:

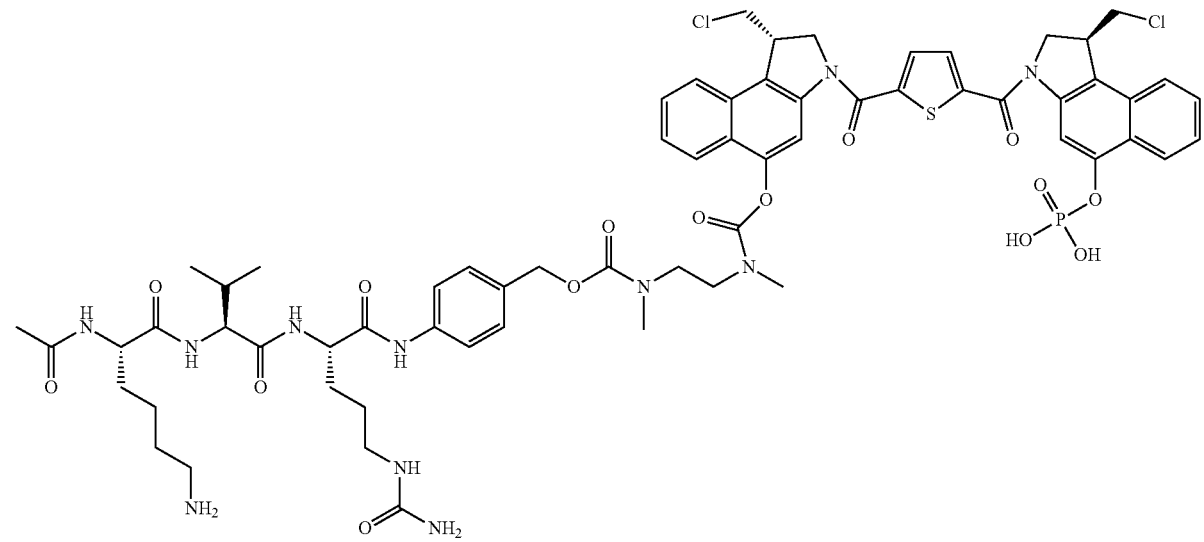 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)c2ccc(C(=O)N3C[C@@H](CCl)c4c3cc(OP(=O)(O)O)c3ccccc43)s2)cc1)C(C)C]

,

N~2~-acetyl-L-lysyl-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]p ent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

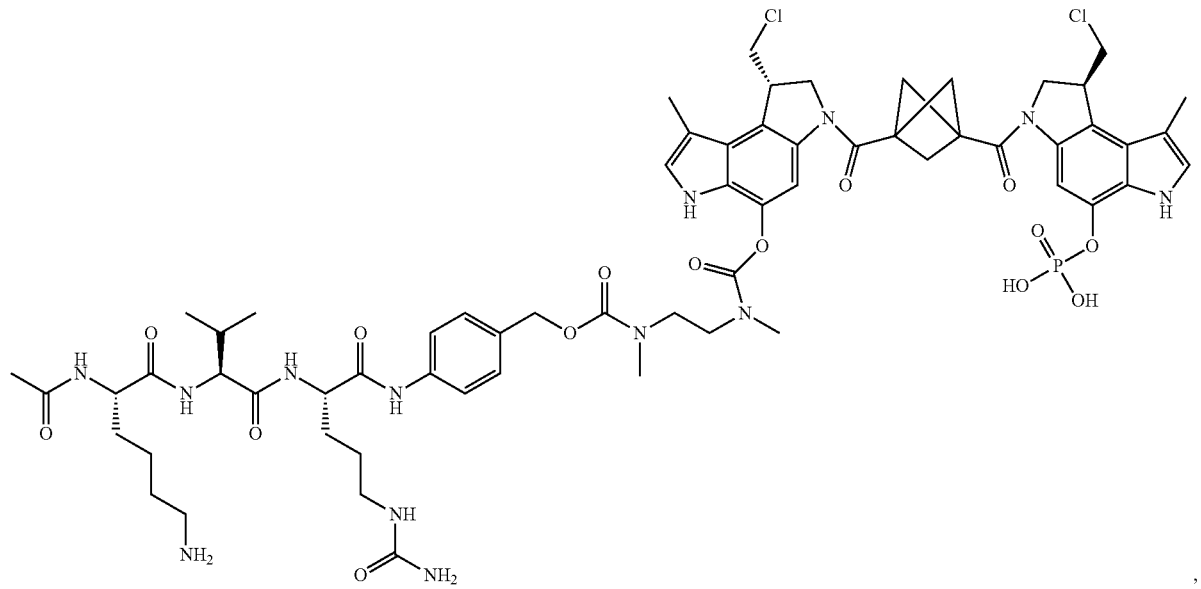 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23CCC(C(=O)N4C[C@@H](CCl)c5c4cc(OP(=O)(O)O)c4[nH]cc(C)c54)(CC2)C3)cc1)C(C)C]

N~2~-acetyl-L-lysyl-L-valyl-N~5~-carbamoyl-N-[4-({[(2-{[({(8S)-8-(chloromethyl)-6-[(4-{[(1S)-1-(chloromethyl)-8-methyl-5-(phosphonooxy)-1,6-dihydropyrrolo[3,2-e]indol-3(2H)-yl]carbonyl}pentacyclo[4.2.0.0~2,5~.0~3,8~.0~4,7~]oct-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

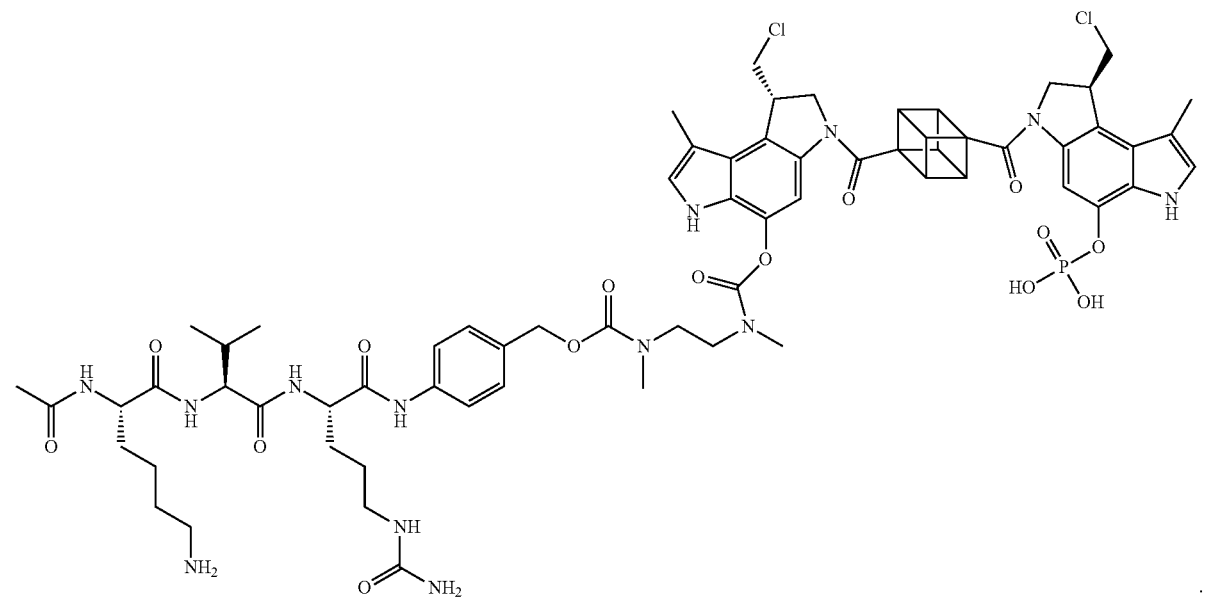 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23C4C5C2C2C3C4C52C(=O)N2C[C@@H](CCl)c3c2cc(OP(=O)(O)O)c2[nH]cc(C)c32)cc1)C(C)C]

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, uncialamicin, dynemicin, and their derivatives.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Hemiasterlin and its analogues (e.g., HTI-286) bind to the tubulin, disrupt normal microtubule dynamics, and, at stoichiometric amounts, depolymerize microtubules.

Maytansines or their derivatives maytansinoids inhibit cell proliferation by inhibiting the mcirotubules formation during mitosis through inhibition of polymerization of tubulin. See Remillard et al., Science 189:1002-1005 (1975). Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464, and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate having the structure Vinca alkyloids are also anti-tubulin agents. Exemplary vinca alkyloids include, but are not limited to, vincristine, vinblastine, vindesine, and vinorelbine.

In some embodiments, the agent moiety is an immunosuppressive agent. Examples of an immunosuppressive agent include, but are not limited to, gancyclovier, etanercept, tacrolimus, sirolimus, voclosporin, cyclosporine, rapamycin, cyclophosphamide, azathioprine, mycophenolgate mofetil, methotrextrate, and glucocorticoids and their analogs and derivatives.

In some embodiments, the agent moiety is an imaging agent (e.g., a fluorophore or a chelator), such as fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N', N'',N'''-tetraacetic acid (DOTA), 1,4,7-triazacyclononane-1, 4,7-triacetic acid (NOTA), 1,4,7-triazacyclononane, 1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

In some embodiments, the agent moiety is a polypeptide. In some embodiments, the polypeptide is an antibody, such as a humanized, human, chimeric, or murine monoclonal antibody.

In some embodiments, the agent moiety is a toxin polypeptide (or a toxin protein). Examples of a toxin polypeptide include, but are not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca ameri-*

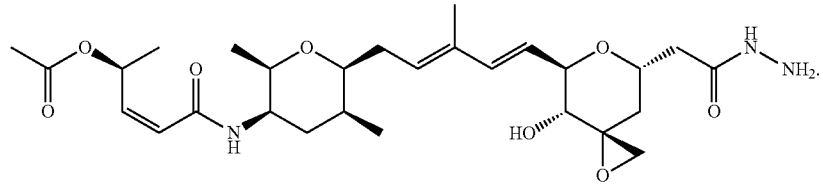 [SMILES: CC(=O)O[C@@H](C)/C=C\C(=O)N[C@@H]1C[C@H](C)[C@H](C/C=C(C)/C=C/[C@H]2O[C@H](CC(=O)NN)C[C@@]3(CO3)[C@@H]2O)O[C@@H]1C]

Examples of pladienolides include, but are not limited to, Pladienolide B, Pladienolide D, and E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Tubulysins are natural products isolated from a strain of myxobacteria that has been shown to depolymerize microtubules and induce mitotic arrest. Exemplary tubulysins include, but are not limited to, tubulysin A, tubulysin B, and tubulysin D.

*cana* proteins (PAPI, PAPII, and PAP-S), *Momordica Charantia* inhibitor, curcin, crotin, *Sapaonaria Officinalis* inhibitor, gelonin, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, radioisotopes or other labels can be incorporated in the agent moiety (e.g., by binding to a chelator) for conjugation of an antibody to an amine donor agent that bears a chelator. Examples of a radioisotope or other labels include, but are not limited to, $^{3}$H, $^{14}$C, $^{15}$N, $^{35}$S, $^{18}$F, $^{32}$P, $^{33}$P, $^{64}$Cu, $^{68}$Ga, $^{89}$Zr, $^{90}$Y, $^{99}$Tc, $^{123}$I, $^{124}$I, $^{125}$I, $^{131}$I, $^{111}$In, $^{131}$In, $^{153}$Sm, $^{186}$Re, $^{188}$Re, $^{211}$At, $^{212}$Bi, and $^{153}$Pb.

In some embodiments, the agent moiety is a biocompatible polymer. The antibody can be conjugated to the biocompatible polymer via the glutamine-containing tag, an endogenous glutamine, and/or a reactive endogenous glutamine, to improve the biological characteristics of the antibody, e.g., to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the amine donor agent (X—Y—Z) is wherein X is $NH_2$ (i.e., thus forming a covalent bond with glutamine as $CH_2$—$CH_2$—CO—NH—), m is a 0 to 20, n is 1 to 8, p is 0 to 3, q is 0 or 1, amino acid is any conventional or nonconventional amino acid, and Z is a cytotoxic agent or an imaging agent.

Conventional or naturally occurring amino acids are divided into groups based on common side-chain properties: (1) non-polar: Met, Ala, Val, Leu, Ile; (2) polar without charge: Cys, Ser, Thr, Asn, Gln; (3) acidic (negatively charged): Asp, Glu; (4) basic (positively charged): Lys, Arg; and (5) residues that influence chain orientation: Gly, Pro; and (6) aromatic: Trp, Tyr, Phe, His. Conventional amino acids include L or D stereochemistry.

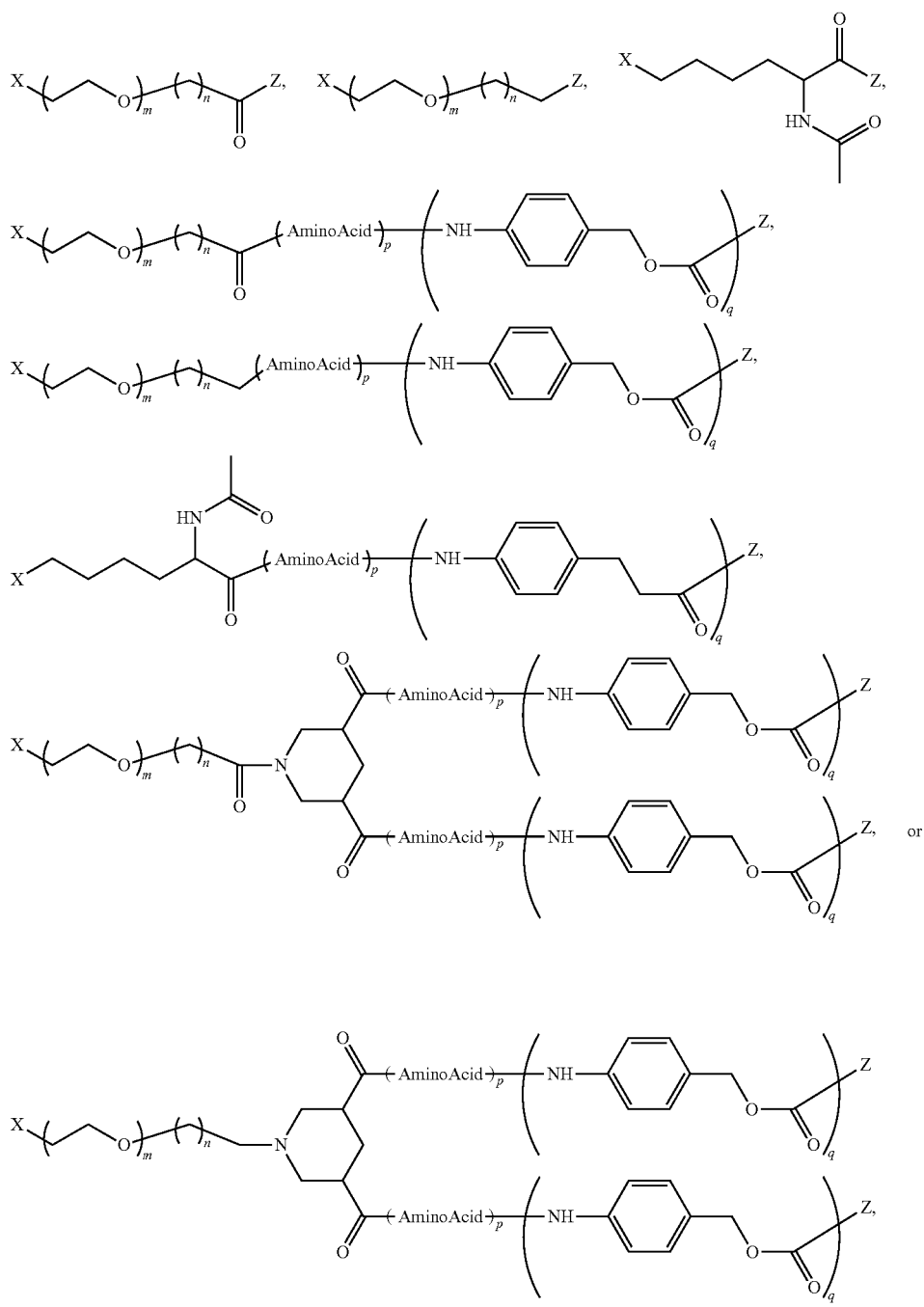

Unconventional amino acids are non-naturally occurring amino acids. Examples of an unconventional amino acid include, but are not limited to, aminoadipic acid, beta-alanine, beta-aminopropionic acid, aminobutyric acid, piperidinic acid, aminocaprioic acid, aminoheptanoic acid, aminoisobutyric acid, aminopimelic acid, citrulline, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N, N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acid derivatives (e.g., 4-hydroxyproline).

In some embodiments, the amine donor agent is a biocompatible polymer comprising a reactive amine and an agent moiety.

In some embodiments, the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly-MMAD, amino-PEG3-C2-MMAD, amino-PEG6-C2-MMAD, amino-PEG3-C2-amino-nonanoyl-MMAD, aminocaproyl-Val-Cit-PABC-MMAD, Ac-Lys-β-Ala-MMAD, Aminocaproyl-MMAD, amino-PEG6-C2-Val-Cit-PABC-MMAD, Ac-Lys-Val-Cit-PABC-MMAD, Ac-Lys-Val-Cit-PABC-0101, amino-PEG3-C2-Val-Cit-PABC-MMAD, amino-PEG6-C2-Val-Cit-PABC-0101, aminocaproyl-MMAE, amino-PEG3-C2-MMAE, amino-PEG2-C2-MMAE, aminocaproyl-MMAF, aminocaproyl-Val-Cit-PABC-MMAE, amino-PEG6-C2-Val-Cit-PABC-MMAF, aminocaproyl-Val-Cit-PABC-MMAF, amino-PEG2-C2-MMAF, amino-PEG3-C2-MMAF, putrescinyl-geldanamycin, Ac-Lys-putrescinyl-geldanamycin, aminocaproyl-3377, aminocaproyl-0131, amino-PEG6-C2-0131, amino-PEG6-C2-3377, aminocaproyl-0121, amino-PEG6-C2-0121, [(3R,5R)-1-{3-[2-(2-aminoethoxy)ethoxy]propanoyl}piperidine-3,5-diyl]bis-Val-Cit-PABC-MMAD, [(3R,5R)-1-{3-[2-(2-aminoethoxy)ethoxy]propanoyl}piperidine-3,5-diyl]bis-Val-Cit-PABC-MMAE, 2-aminoethoxy-PEG6-NODAGA (or 2,2'-(7-(1-amino-28-carboxy-25-oxo-3,6,9,12,15,18,21-heptaoxa-24-azaoctacosan-28-yl)-1,4,7-triazonane-1,4-diyl)diacetic acid), and N-2-acetyl-L-lysyl-L-valyl-N~5~-carbamoyl-N-[4-({[(2-{[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide. In some embodiments, the amine donor agent is Ac-Lys-Val-Cit-PABC-MMAD, Ac-Lys-Val-Cit-PABC-0101, or amino-PEG6-C2-MMAD. In some embodiments, the acyl donor glutamine-containing tag comprises the amino acid sequence GGLLQGA (SEQ ID NO: 23) or GGLLQGPP (SEQ ID NO:22), and additionally LLQGA (SEQ ID NO: 11), LLQGPP (SEQ ID NO:20) or LLQG (SEQ ID NO: 2), and the amine donor agent is Ac-Lys-Val-Cit-PABC-MMAD, Ac-Lys-Val-Cit-PABC-0101, and/or amino-PEG6-C2-MMAD. Exemplary structures of the amine donor agent are listed in Table 2.

TABLE 2
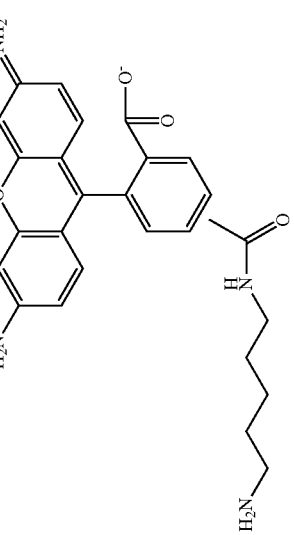
Alexa 488 cadaverine
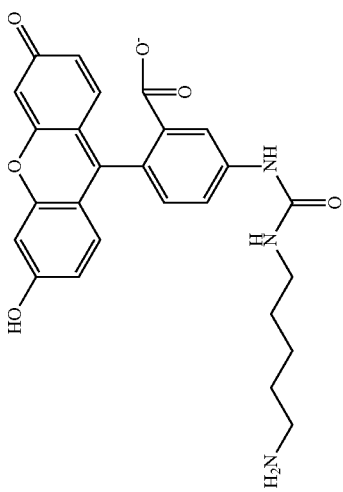
5-FITC cadaverine
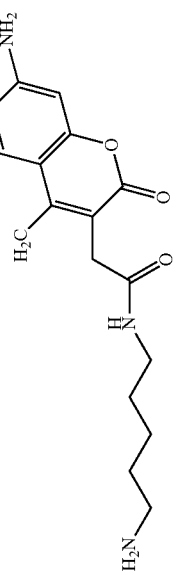
Alexa 350 cadaverine TABLE 2-continued
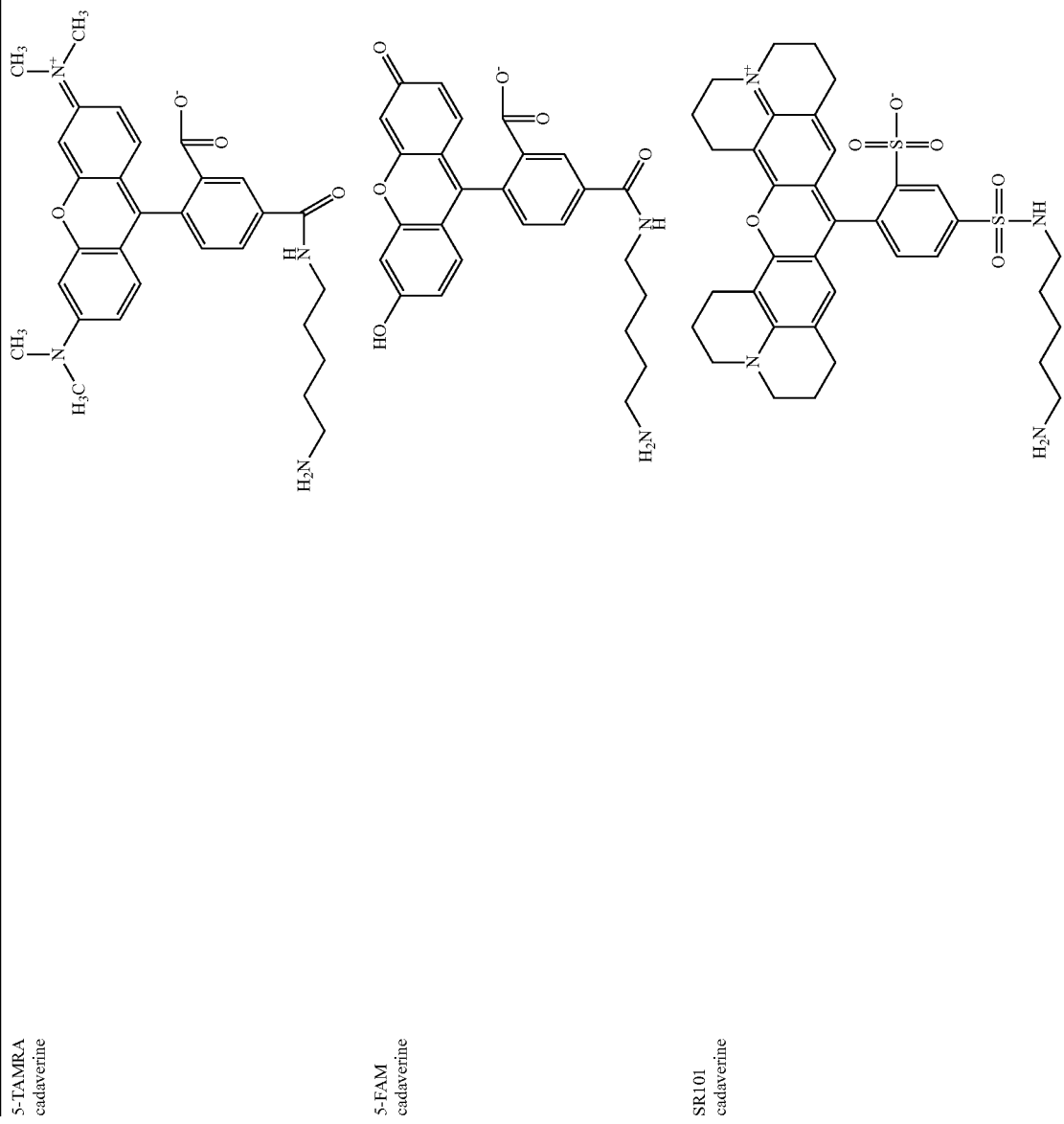
5-TAMRA cadaverine
5-FAM cadaverine
SR101 cadaverine TABLE 2-continued
| | |
|---|---|
| 5,6-TAMRA cadaverine | 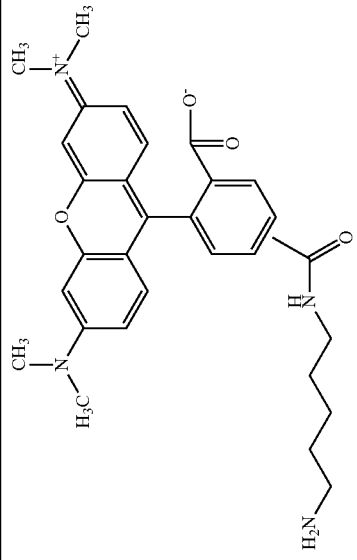 |
| 5-FAM lysine | 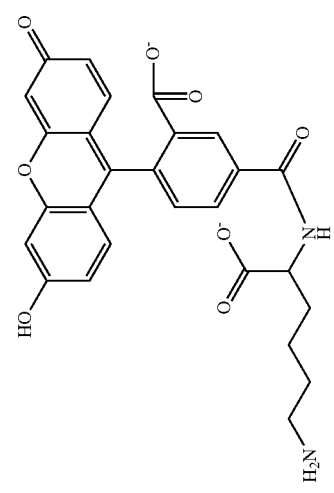 |
| Ac-Lys-Gly-MMAD | 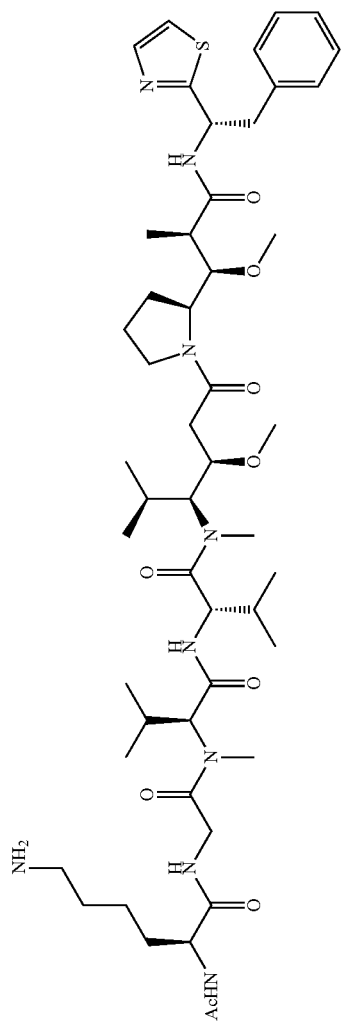 |

TABLE 2-continued
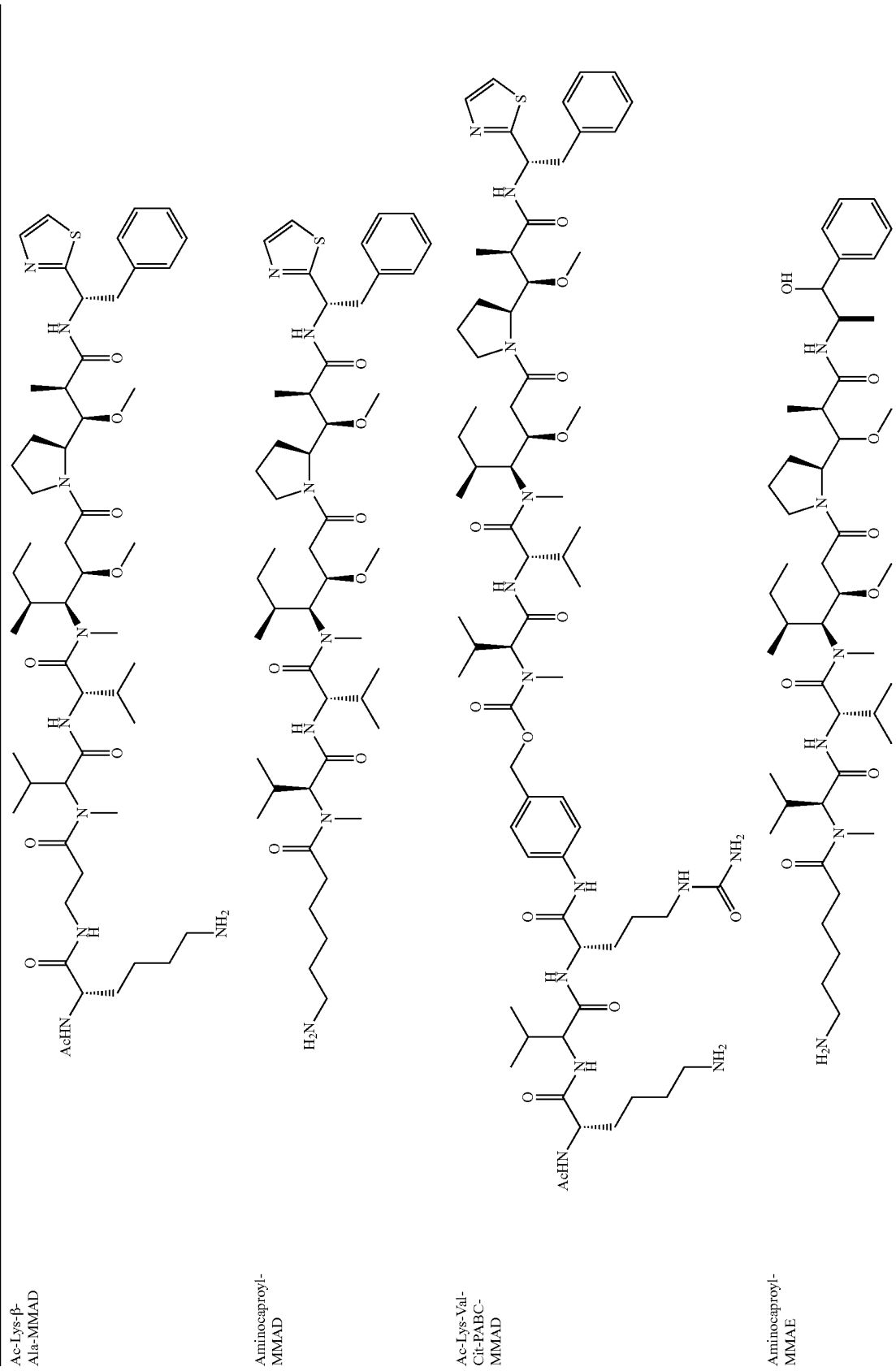
Ac-Lys-β-Ala-MMAD
Aminocaproyl-MMAD
Ac-Lys-Val-Cit-PABC-MMAD
Aminocaproyl-MMAE TABLE 2-continued

| Amino-PEG2-C2-MMAE (or Amino-PEG2-Propionyl-MMAE) |
| Amino-PEG3-C2-MMAE (or Amino-PEG3-Propionyl-MMAE) |
| Aminocaproyl-MMAF |
| Aminocaproyl-Val-Cit-PABC-MMAF |

TABLE 2-continued

| Name | Structure |
|---|---|
| Amino-PEG3-C2-MMAD (or Amino-PEG3-Propionyl-MMAD) | 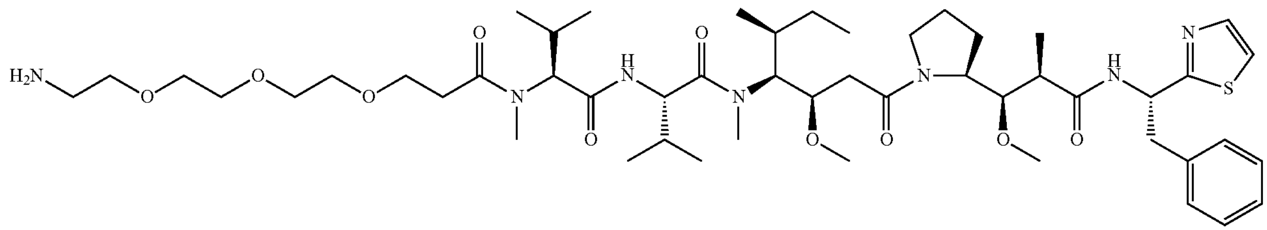 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)CCOCCOCCOCCN)C(C)C] |
| Amino-PEG6-C2-MMAD (or Amino-PEG6-Propionyl-MMAD) | 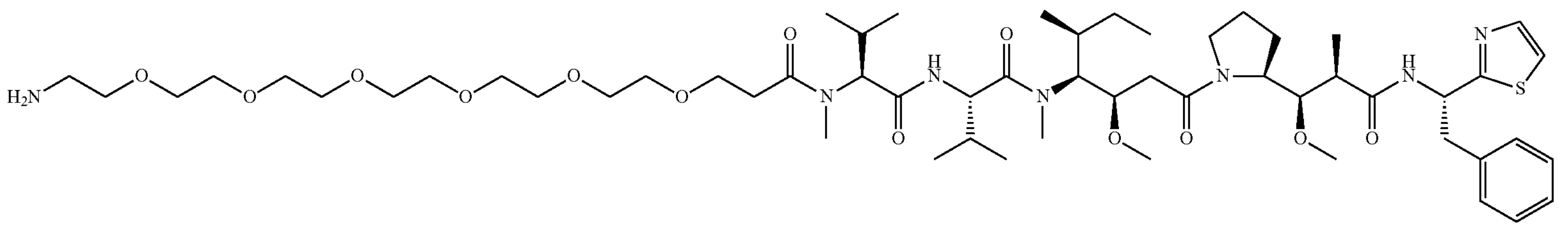 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)CCOCCOCCOCCOCCOCCOCCN)C(C)C] |
| Amino-PEG3-C2-aminononanoyl-MMAD (or Amino-PEG3-Propionyl-aminononanoyl-MMAD) | |
| Amino-nonanoyl-MMAD | 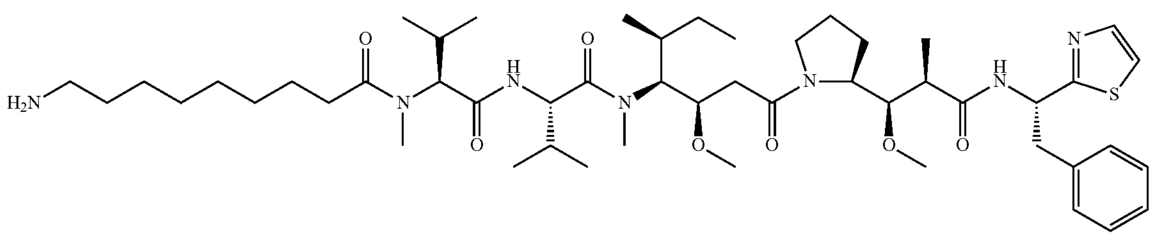 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)CCCCCCCCN)C(C)C] |

TABLE 2-continued
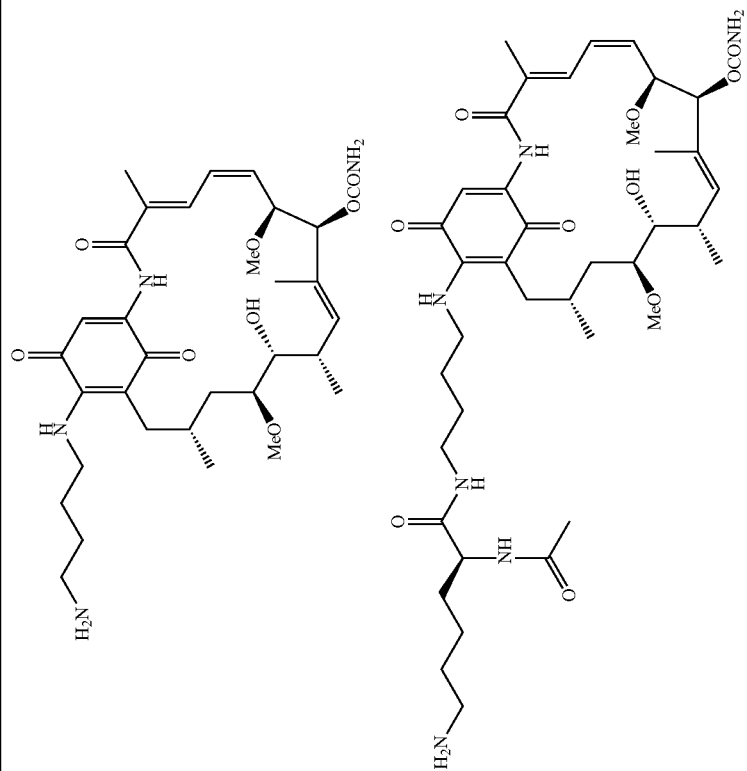
Putrescinyl-Geldanamycin
Ac-Lys-Putrescinyl-Geldanamycin TABLE 2-continued
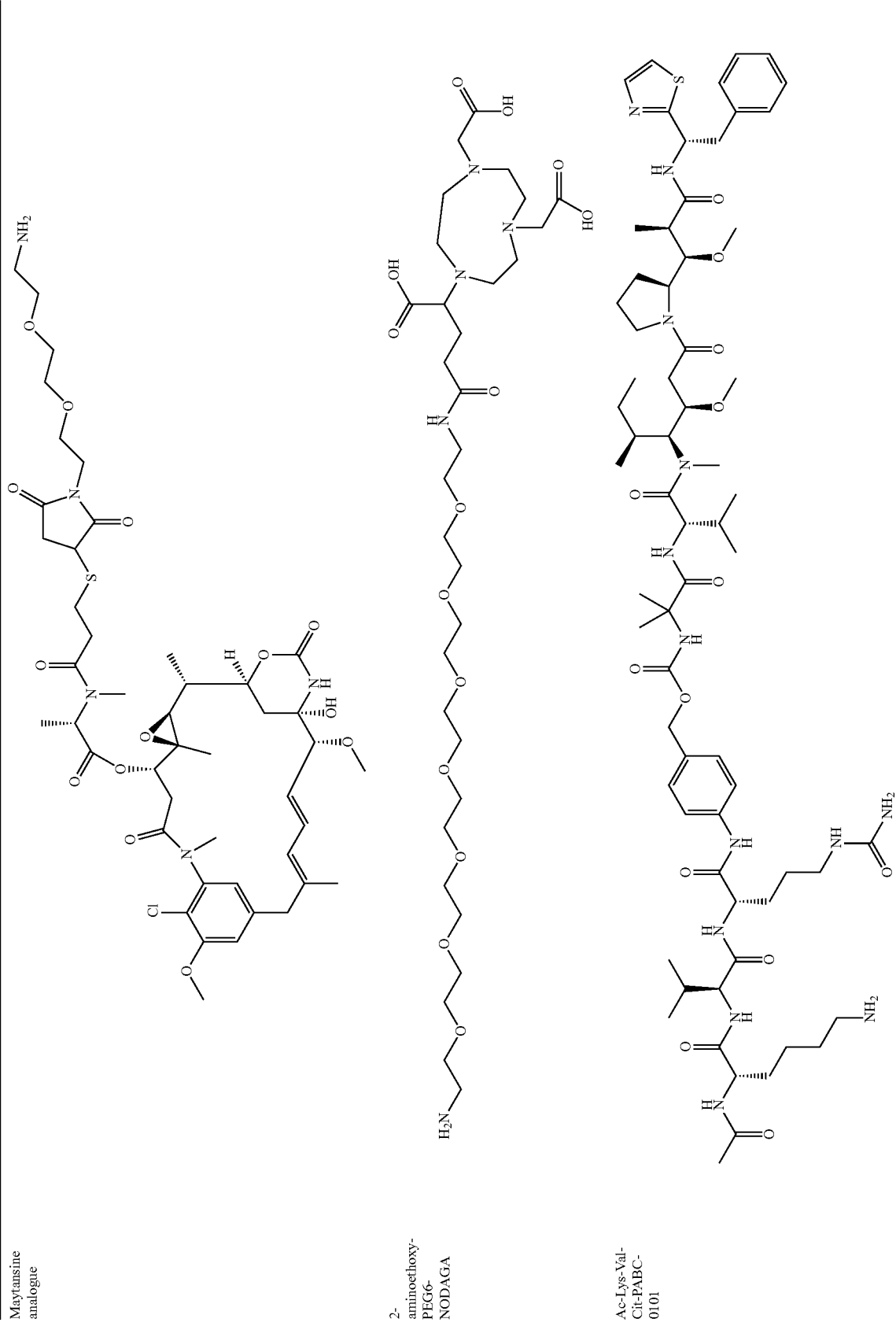
Maytansine analogue
2-aminoethoxy-PEG6-NODAGA
Ac-Lys-Val-Cit-PABC-0101

TABLE 2-continued
| Amino-PEG6-C2-3377 | 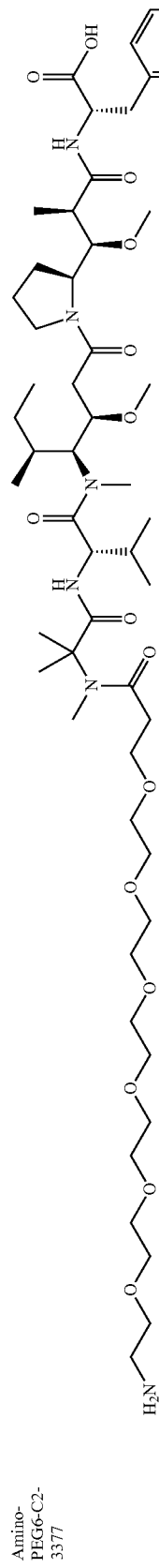 |
| --- | --- |
| Amino-PEG6-C2-0131 | 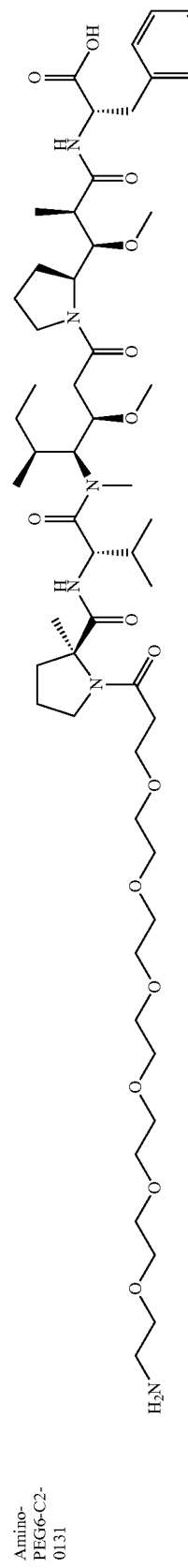 |
| Amino-PEG6-C2-0121 | 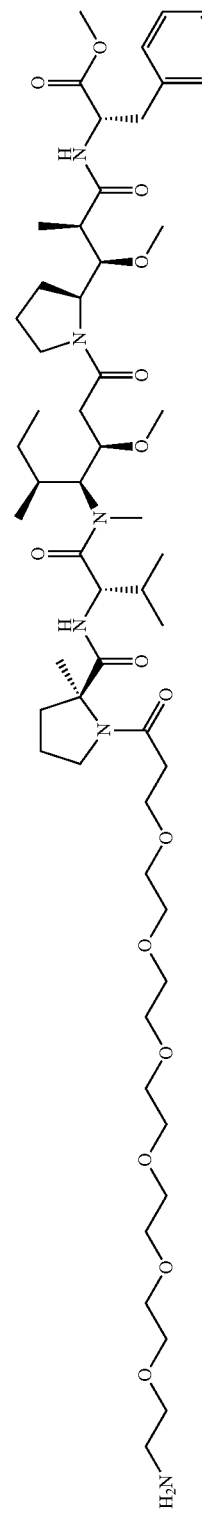 |
| Amino-PEG6-C2-Val-Cit-PABC-MMAE | 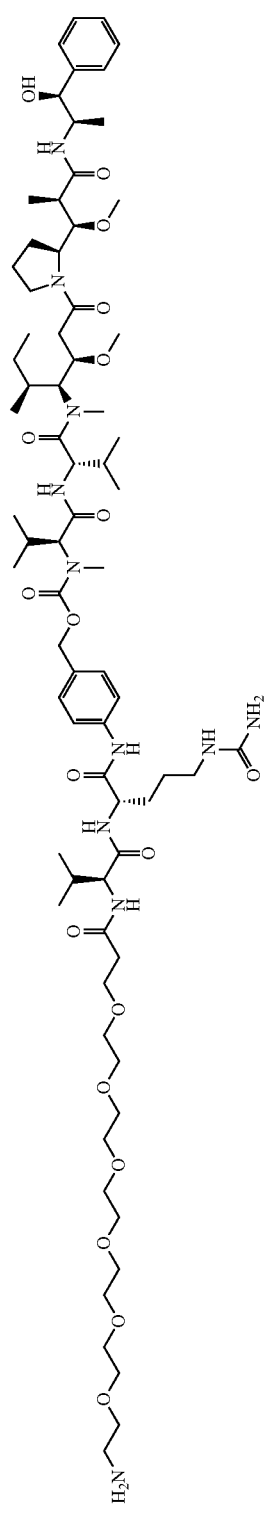 |

TABLE 2-continued

| Amino-PEG6-C2-Val-Cit-PABC-MMAF | Amino-PEG6-C2-Val-Cit-PABC-0101 |

TABLE 2-continued
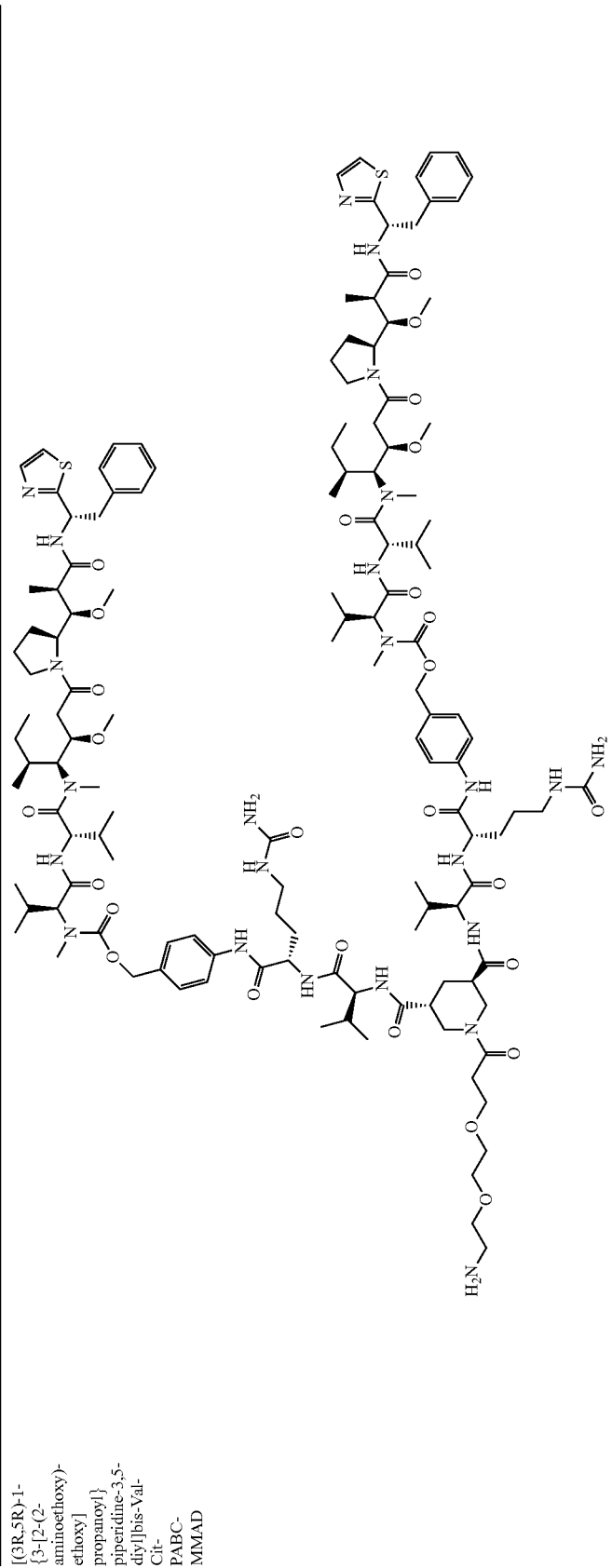
[(3R,5R)-1-
{3-[2-(2-
aminoethoxy)-
ethoxy]
propanoyl}
piperidine-3,5-
diyl]bis-Val-
Cit-
PABC-
MMAD TABLE 2-continued
[(3R,5R)-1-{3-[2-(2-aminoethoxy)ethoxy]propanoyl}piperidine-3,5-diyl]bis-Val-Cit-PABC-MMAE
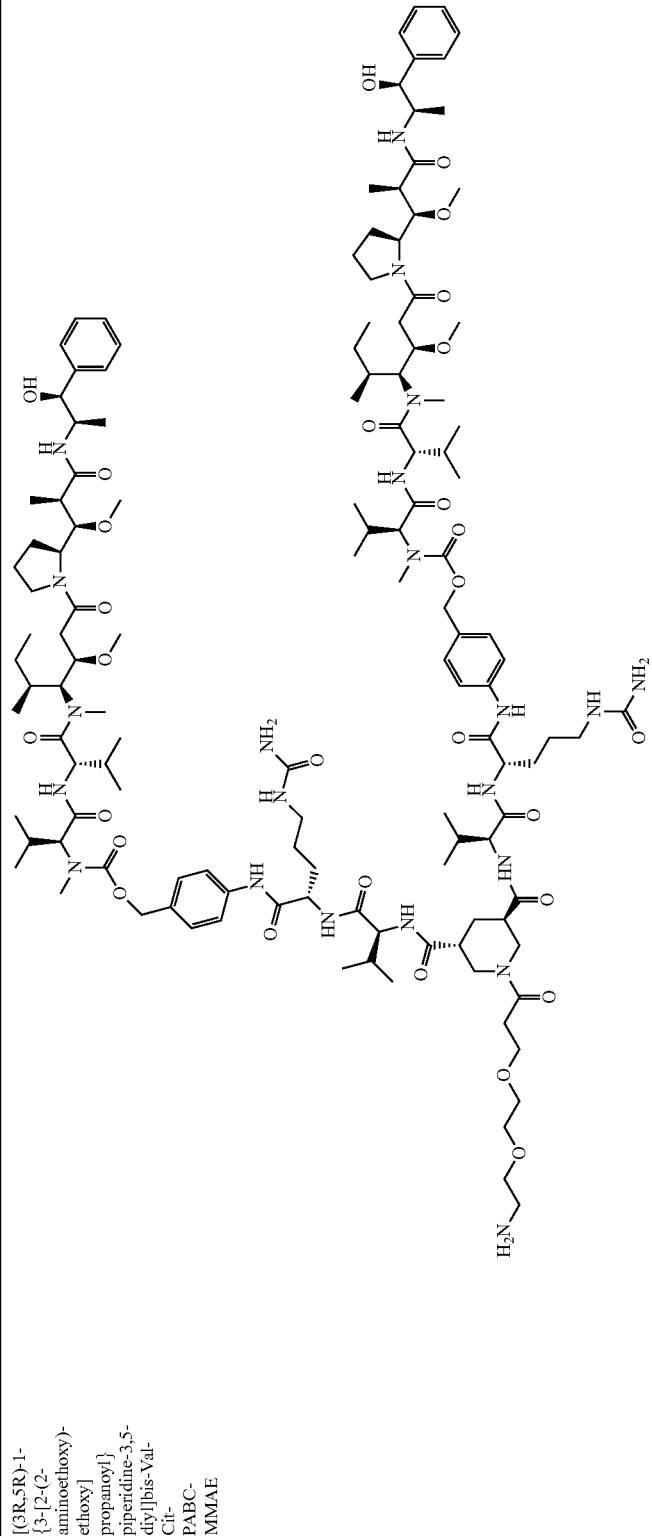

TABLE 2-continued
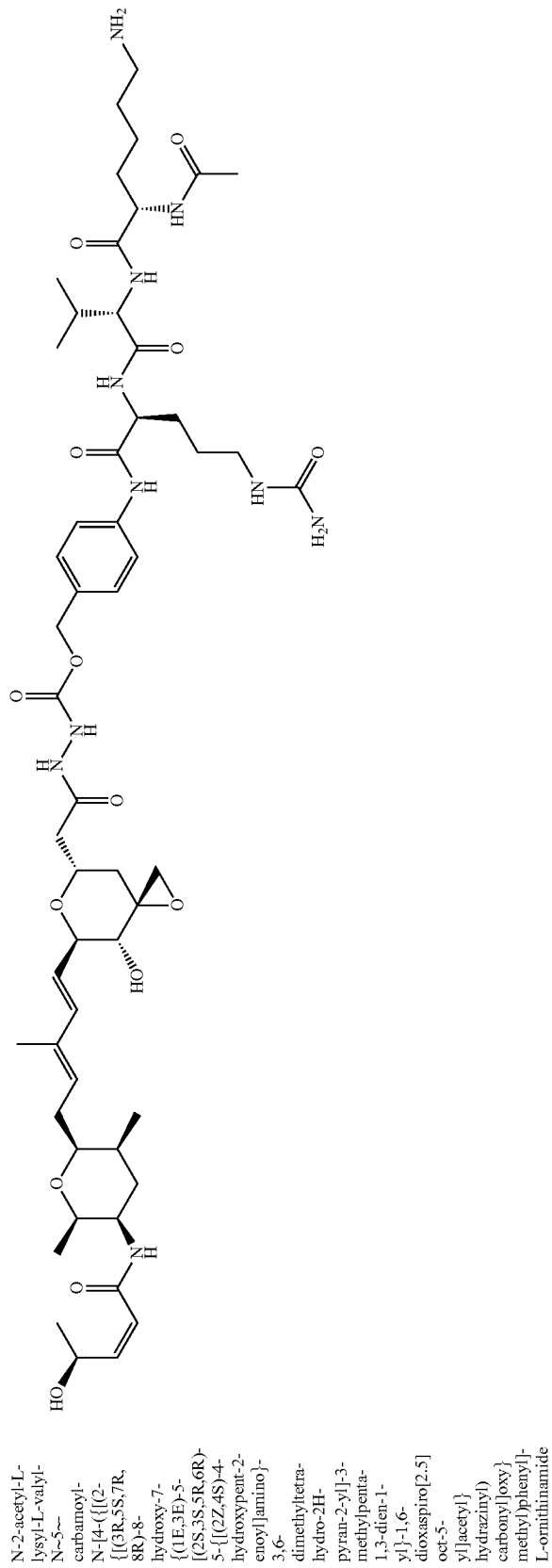
N-2-acetyl-L-lysyl-L-valyl-N-5—carbamoyl-N-[4-({[(2-{[(3R,5S,7R,8R)-8-hydroxy-7-{(1E,3E)-5-[(2S,3S,5R,6R)-5-[((2Z,4S)-4-hydroxypent-2-enoyl]amino]-3,6-dimethyltetra-hydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide Methods for Making the Higher Loaded Antibody-Drug Conjugate Methods for making the ADCs described herein are also provided. In one aspect, the invention provides a method for preparing an ADC comprising the formula: antibody-(T-(X—Y—$Z_a$)$_b$)$_c$, wherein: T is 1) a glutamine-containing tag engineered at a specific site, 2) an endogenous glutamine, and/or 3) an endogenous glutamine made reactive by antibody engineering or an engineered transglutaminase; X is an amine donor unit; Y is a linker; and Z is an agent moiety; X—Y—Z is an amine donor agent site-specifically conjugated to the glutamine-containing tag, the endogenous glutamine, and/or the reactive endogenous glutamine; a is an integer from 1 to 6; b is an integer from 1 to 6; c is an integer from 1 to 20; and wherein the product (drug-antibody ratio) of a, b, and c is at least about 5, comprising the steps of: a) providing an antibody-T molecule comprising the antibody and the glutamine-containing tag; and/or the antibody with the endogenous and/or reactive endogenous glutamine; b) contacting the amine donor agent with the antibody-T molecule in the presence of a transglutaminase (e.g., an engineered transglutaminase or a purified transglutaminase); and c) allowing the antibody-T to covalently link to the amine donor agent to form the antibody-drug conjugate. In some embodiments, the antibody-T molecule is expressed in CHO cells.

In some embodiments, the ADC prepared using the methods described herein has conjugation efficiency of at least about 51%. In some embodiments, the ADC has conjugation efficiency of at least about any of 51%-60%, 61%-70%, 71%-80%, 81%-90%, or 91%-100%. In some embodiments, the ADC has conjugation efficiency of about any of 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100%.

In some embodiments, the molar concentration ratio between the amine donor agent contacted and the antibody-T molecule contacted is from about 4:1 to about 10000:1. For example, the molar concentration ratio between the amine donor agent (e.g., a cytotoxic drug) and the antibody (e.g., attached to a glutamine-containing tag or containing a native/reactive glutamine) loaded or used for the transglutaminase-catalyzed conjugation reaction can be about 20:1. In some embodiments, the concentration ratio between the amine donor agent contacted and the antibody-T molecule contacted is about any of 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

In some embodiments, when an antibody is conjugated with an amine donor agent via a glutamine-containing tag, an endogenous glutamine, and/or a reactive endogenous glutamine at a specific site, the ADC is more stable (e.g., longer in vivo ADC half-life) and/or have higher exposure. For example, the ADC comprising amino modifications of N297Q and K222R; glutamine-containing tag(s) at carboxyl terminus at the light chain and/or the heavy chain of the antibody, and/or at one or more positions in the antibody light chain or heavy chain (e.g., see Table 1) as described herein, is more stable than the conventional ADC with the maleimide linkage.

In some embodiments, the methods provided herein further comprise a purification step. The ADCs described herein can be purified using various purification methods, such as, e.g., hydroxylapatite chromatography; dialysis; affinity chromatography; hydrophobic interaction chromatography (HIC) (e.g, fractionation on a HIC); ammonium sulphate precipitation; polyethylene glycol or polyethylene glycol derivative precipitation, anion or cation exchange chromatography; reverse phase HPLC; chromatography on silica; chromatofocusing; SDS-PAGE, gel filtration, size exclusion chromatography, and weak partitioning chromatography.

In some embodiments, at least one purification step comprises a step of affinity chromatography method. Protein A ligand (synthetic, recombinant, or native) may be used to affinity purify the engineered Fc-containing polypeptide conjugates described herein. Synthetic or recombinant Protein A ligand may be purchased commercially from GE Healthcare (Piscataway, N.J.), Pierce (Rockford, Ill.), Sigma-Aldrich (St. Louis, Mo.), or Applied Biosystems (Foster City, Calif.), and native Protein A ligand (e.g., MABSELECT™, PROSEP™ Va, and PROSEP™ Ultra Plus) may be purchased commercially from GE Healthcare (Piscataway, N.J.) or Millipore (Billerica, Mass.).

In some embodiments, the purified ADC as described herein resulting from the purification step is highly pure, i.e., at least about any of 70%-75%, 75%-80%, 80%-85%, 85%-90%, 90%-95%, 95%-98%, or 99% pure. For example, the purified ADC is about any of 80%, 85%, 90%, 91%, 92%, 93%, 94%, 95%, 96%, 97%, 98%, or 99% pure.

Method of Using Antibody-Drug Conjugates with High Drug Loading

The ADCs of the present invention are useful in various applications including, but are not limited to, therapeutic treatment methods and diagnostic treatment methods.

In one aspect, the invention provides a method for treating a cancer in a subject. Accordingly, in some embodiments, provided is a method of treating a cancer in a subject in need thereof comprising administering to the subject an effective amount of a composition (e.g., pharmaceutical composition) comprising the ADC as described herein. As used herein, cancers include, but are not limited to, a solid cancer (such as bladder, breast, cervical, choriocarcinoma, colon, esophageal, gastric, glioblastoma, head and neck, kidney, liver, lung (e.g., Non Small Cell Lung Cancer (NSCLC)), oral, ovarian, pancreatic, prostate, and skin cancer); and a liquid cancer (such as acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, multiple myeloma, Non-Hodgkin Lymphoma (NHL) (including follicular lymphoma (FL) and diffuse large B-cell lymphoma (DLBCL)), and adult T-cell leukemia).

In some embodiments, provided is a method of inhibiting tumor growth or progression in a subject in need thereof, comprising administering to the subject an effective amount of a composition comprising the ADCs as described herein. In other embodiments, provided is a method of inhibiting metastasis of cancer cells or tumors (e.g., solid or liquid tumors) in a subject in need thereof, comprising administering to the subject an effective amount of a composition comprising the ADCs as described herein. In other embodiments, provided is a method of inducing tumor regression in a subject in need thereof, comprising administering to the subject an effective amount of a composition comprising the ADCs as described herein.

In another aspect, provided is a method of detecting, diagnosing, and/or monitoring a condition associated with a cancer-related protein (e.g., Trop-2, BRCA1, BRCA2, HER2, VEGF, CD20, CD25, EFGR, 5T4, CD22, etc.) in vivo or in vitro. Accordingly, in some embodiments, provided is a method of diagnosing cancer in a subject suspected of suffering from cancer, comprising a) contacting a sample of the subject with the ADC as described herein under conditions that result in binding of the ADC with a cancer-related protein, and b) determining binding of the ADC to the cancer-related protein.

The agent moiety in the ADCs as described herein can be a detectable moiety such as an imaging agent and an enzyme-substrate label. The ADCs as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the ADCs as described herein. The therapeutic agents include, but are not limited to, a second ADC (e.g., conventional ADC such as brentuximab vedotin (ADCETRIS®) and ado-trastuzumab emtansine (KADCYLA®)), an antibody (e.g., an anti-VEGF antibody, an anti-HER2 antibody, anti-CD25 antibody, and/or an anti-CD20 antibody), an angiogenesis inhibitor, a cytotoxic agent (e.g., docetaxel, cisplatin, doxorubicin, mitomycin, tamoxifen, or fluorouracil), and an anti-inflammatory agent (e.g., prednisone, and progesterone).

Pharmaceutical Compositions

The present invention also provides a pharmaceutical composition comprising the higher loaded ADCs as described herein in a pharmaceutically acceptable excipient or carrier. The ADCs can be administered alone or in combination with one or more other ADCs of the present invention or in combination with one or more other drugs (or as any combination thereof). For example, the ADCs of the present invention can be administered in combination with the conventional ADCs (e.g., DAR of 1-4) or the site-specific ADCs using transglutaminase-mediated conjugation technology as described herein with DARs of 1-4. The methods and uses of the invention thus also encompass embodiments of combinations (co-administration) with other active agents, as detailed below.

As used herein, the term "co-administration," "co-administered," or "in combination with" is intended to mean and does refer to the following: (i) simultaneous administration of a combination of an ADC disclosed herein and therapeutic agent(s) to a patient in need of treatment, when such components are formulated together into a single dosage form which releases said components at substantially the same time to said patient; (ii) substantially simultaneous administration of such combination of an ADC disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an ADC disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an ADC disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient.

Generally, the ADCs disclosed herein are suitable to be administered as a formulation in association with one or more pharmaceutically acceptable excipient(s). The term 'excipient' is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the antibody.

The present invention also provides a pharmaceutical composition comprising a plurality of higher loaded ADCs of the present invention as described herein, wherein an average drug-antibody ratio (DAR) is about 5.0 to about 720.0. In some embodiments, the average DAR is at least about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 16.0, 16.5, 17.0, 17.5, 18.0, 18.5, 19.0, 19.5, 20.0, 30.0, 40.0, 50.0, 60.0, 70.0, 80.0, 90.0, 100.0, 110.0, 120.0, 130.0, 140.0, 150.0, 200.0, 250.0, 300.0, 350.0, 400.0, 450.0, 500.0, 550.0, 600.0, 650.0, or 700.0.

In one variation, the present invention further provides a pharmaceutical composition comprising a plurality of ADCs, wherein at least one ADC is the higher loaded ADC of the present invention as described herein, and wherein an average drug-antibody ratio is about 4.1 to about 720.0. In some embodiments, the average DAR is at least about 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 16.0, 16.5, 17.0, 17.5, 18.0, 18.5, 19.0, 19.5, 20.0, 30.0, 40.0, 50.0, 60.0, 70.0, 80.0, 90.0, 100.0, 110.0, 120.0, 130.0, 140.0, 150.0, 200.0, 250.0, 300.0, 350.0, 400.0, 450.0, 500.0, 550.0, 600.0, 650.0, or 700.0. For example, the pharmaceutical composition can comprise one or more site-specific ADCs having DAR of at least about 5 as described herein, and one or more site-specific ADCs (using transglutaminase-mediated conjugation technology as described herein) having DAR of 1, 2, 3, or 4. As another example, the pharmaceutical composition can comprise 1) one or more site-specific ADCs having DAR of at least about 5 as described herein, 2) one or more site-specific ADCs (using transglutaminase-mediated conjugation technology as described herein) having DAR of 1, 2, 3, or 4, and 3) one or more conventional ADCs with the maleimide linkage with DAR of 1, 2, 3, 4, or more.

In some embodiments, the ADCs described herein can be deimmunized to reduce immunogenicity upon administration to a subject suing known techniques such as those described, e.g., in PCT Publication WO98/52976 and WO00/34317.

Pharmaceutical compositions of the present invention and methods for their preparation are readily apparent to those skilled in the art. Such compositions and methods for their preparation may be found, for example, in Remington's Pharmaceutical Sciences, 22nd Edition (Mack Publishing Company, 2012). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the engineered polypeptide conjugates disclosed herein.

The pharmaceutical compositions of the invention are typically suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the engineered Fc-containing polypeptide, e.g., antibody-drug conjugate or bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the agent moiety (e.g., small molecules such as cytotoxic agent) and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of an ADC disclosed herein is typically in the range of about 0.01 mg to about 1200 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of an ADC as disclosed herein is about 0.01 to about 1000 mg/patient/month. In certain embodiments, the ADC may be administered at about 1 to about 200 or about 1 to about 150 mg/patient/month. In some embodiments, the patient is human.

Kits

The invention also provides kits (or articles of manufacture) for use in the treatment of the disorders described above. Kits of the invention include one or more containers comprising a purified ADC and instructions for using the conjugate for treating a disease. For example, the instructions comprise a description of administration of the ADC to treat a disease, such as cancer (e.g., a solid or liquid cancer). The kit may further comprise a description of selecting an individual suitable for treatment based on identifying whether that individual has the disease and the stage of the disease.

The instructions relating to the use of the ADC generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is the higher loaded ADC as described herein. The container may further comprise a second pharmaceutically active agent.

Kits may optionally provide additional components such as buffers and interpretive information. Normally, the kit comprises a container and a label or package insert(s) on or associated with the container.

EXAMPLES

It is understood that the examples and embodiments described herein are for illustrative purposes only and that various modifications or changes in light thereof will be suggested to persons skilled in the art and are to be included within the spirit and purview of this application.

Example 1

Cytotoxicity of Increasingly Higher Loaded, Site-Specifically Conjugated Anti-Trop-2-ADCs in Cells with High Expression of the Target (BxPC3, Trop2+++)

This example illustrates the in vitro cytotoxicity of higher loaded ADCs (site-specific and conventional) in high target expressing BxPC3 cells.

Antibody-Drug Conjugation a. Transglutaminase-Mediated Antibody-Drug Conjugation Chimeric mouse anti-Trop-2 antibodies were expressed as human IgG1 subtypes engineered with glutamine-containing transglutaminase ("Q") tags at various amino acid positions (e.g., TG6, LCQ04, H7c, L11b, see Table 1) and conjugated with various linkers and payloads (e.g., aminocaproyl-vc-PABC-M MAD (aminocaproyl-Valine-Citrulline-p-amino-benzyloxycarbonyl-MMAD); amino-PEG6-C2-MMAD). In one instance, the transglutaminase tags were engineered at both the light chain and heavy chain C-termini of the antibody, as well as at position 297 of the human IgG (EU numbering scheme) (e.g., the wild-type amino acid asparagine (N) was substituted with glutamine at position 297 of the Trop-2 antibody (N297Q)). Combination of tags engineered at both the light chain and the heavy chain, or multiple sites within the heavy or light chain of the antibodies, carried multiple conjugation sites per antibody (e.g., DAR of 4-10). Anti-Trop-2 antibody conjugation to a payload (e.g., MMAD) was then achieved via microbial transglutaminase-catalyzed transamidation reaction between the anti-Trop-2 antibody carrying a glutamine-containing tag(s) at the specific site (e.g., carboxyl terminus and/or amino terminus of the heavy chain or light chain, position 297, and/or at another site of the antibody) and an amine-containing linker linked to a payload (e.g., MMAD). In some instances, the wild-type amino acid lysine at position 222 (EU numbering scheme) of the antibody was replaced with amino acid arginine ("K222R"). For example, the K222R substitution was found to have the surprising effect of resulting in more homogenous antibody and payload conjugate composition, and/or significant decrease in interchain crosslinking with the glutamine tag on the C terminus of the antibody light chain. In the transamidation reaction, the glutamine on the antibody acted as an acyl donor, and the amine-containing compound acted as an acyl acceptor (amine donor). Purified anti-Trop-2 antibody in the concentration of 33 µM was incubated with a 10-100 M excess acyl acceptor, ranging between 33-3300 µM, in the presence of 1-3% (w/v) *Streptoverticillium mobaraense* transglutaminase (ACTIVA™, Ajinomoto, Japan) in 150 mM sodium chloride or sodium sulfate, and 25 mM MES, HEPES [4-(2-hydroxyethyl)-1-piperazineethanesulfonic acid] or Tris HCl buffer at pH range 6.2-9.2. The reaction conditions were adjusted for individual acyl acceptor derivatives, and the optimal efficiency and specificity were typically observed for 33 µM antibody, 660 µM derivative, and 2% (w/v) transglutaminase in 150 mM NaCl, 25 mM Tris HCl, pH 8.5. Following incubation at 37° C. for 16-20 hours, the antibody was purified on MabSelect SuRe™ resin or Butyl Sepharose™ High Performance (GE Healthcare, Piscataway, N.J.) using standard chromatography methods known to persons skilled in the art, such as commercial affinity chromatography and hydrophobic interaction chromatography from GE Healthcare.

b. Conventional Antibody-Drug Conjugation

To generate an antibody (e.g., a chimeric mouse anti-Trop-2 antibody (m7E6) conjugated with PEG6-C2-MMAD via the conventional maleimide linkage with an average drug loading of 4 (e.g., 4 MMAD per antibody molecule), antibody at 5 mg/mL was first reduced with 7.5 molar equivalents of TCEP (tris(2-carboxyethyl)phosphine) in buffer containing 25 mM Tris, pH 7.5, 150 mM NaCl for 2 hrs at 37° C. A 7.5 molar excess of maleimido-PEG6-C2-MMAD was added to the reduced antibody at room temperature (approximately 22° C.) and incubated for 1 hour. The reaction mixture was dialyzed against PBS (Phosphate Buffered Saline) at 4° C. and sterile filtered through a 0.2 µm filter. To generate m7E6 with maleimido-PEG6-C2-MMAD to a drug loading of 8, antibody was reduced with a 10 molar excess of TCEP in reaction buffer as above with inclusion of 50 mM EDTA (Ethylenediaminetetraacetic acid). A 12 molar excess of maleimido-PEG6-C2-MMAD was added to the reduced antibody and material processed as above. To generate m7E6 conjugated with maleimido-PEG6MMAD to a drug loading of 6, antibody was reduced with 8 fold molar excess of TCEP in buffer as for the DAR 8 reduction, followed by the addition of 8 fold molar excess of maleimido-PEG6-C2-MMAD. To purify the DAR 6 species, the reaction mixture was diluted to obtain a buffer composition of 0.75 M ammonium sulfate, 25 mM potassium phosphate, pH 7 (Buffer A). The material was applied to a 2×1 ml Butyl HP Hi Trap (GE Healthcare) connected in series, washed with 2 CV (column volume) Buffer A, and eluted with a 20 CV linear gradient into 25 mM potassium phosphate, pH 7, with 20% isopropanol. Fractions containing DAR 6 were pooled, dialyzed against PBS, concentrated using a 10 kDa Amicon Ultra centrifugal filter unit (Millipore Corporation).

In Vitro Studies

In vitro cytotoxicity studies of chimeric anti-Trop2 antibodies m7E6 H7c amino-PEG6-C2-MMAD (DAR 1.96, site-specific), m7E6 L11b amino-PEG6-C2-MMAD (DAR 1.96, site-specific), m7E6 TG6 amino-PEG6-C2-MMAD (DAR 1.99, site-specific), m7E6 LCQ04/K222R amino PEG6-C2-MMAD (DAR 1.97, site-specific), m7E6 N297Q/K222R amino-PEG6-C2-MMAD (DAR 3.83, site-specific), m7E6 N297Q/K222R/LCQ04 amino-PEG6-C2-MMAD (DAR 5.85, site-specific), m7E6 N297Q/K222R/LCQ04/TG6 amino-PEG6-C2-MMAD (DAR 7.71, site-specific), m7E6 N297Q/K222R/LCQ04/H7c amino-PEG6-C2-MMAD (DAR 7.76, site-specific), m7E6 N297Q/K222R/LCQ04/L11b amino-PEG6-C2-MMAD (DAR 7.80, site-specific) and m7E6 maleimido-PEG6-C2-MMAD (DAR 7.20, conventional) were performed with target-expressing BxPC3 cells. The number of DAR in this example and the other examples as described herein refers to the ratio of payload per antibody molecule. The linker used was PEG6, and the payload used was MMAD. BxPc3 is a cancer cell line with high target expression levels (Trop-2+++). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. The results of the cytotoxicity assay are shown in FIG. 1 and summarized in Table 3. Three site specific molecules with DAR of 7.71 (m7E6 N297Q/K222R/LCQ04/TG6 amino-PEG6-C2-MMAD), 7.76 (m7E6 N297Q/K222R/LCQ04/H7c amino-PEG6-C2-MMAD) and 7.80 (m7E6 N297Q/K222R/LCQ04/L1 b amino-PEG6-C2-MMAD) were as potent as the conventionally conjugated ADC with a DAR of 7.20 (m7E6 maleimido-PEG6-C2-MMAD).

These results show that while all ADCs achieved near complete cell killing irrespective of their payload loading on high target expressing BxPC3 cells, the higher loaded conjugates were more potent in comparison to the lower loaded conjugates.

TABLE 3

| ADC | DAR | Conjugation | Maximum % cytotoxicity | 50% cytotoxicity (nM) | EC50 (nM) |
| --- | --- | --- | --- | --- | --- |
| m7E6 H7c amino-PEG6-C2-MMAD | 1.96 | site-specific | 89 | 0.435 | 0.313 |
| m7E6 L11b amino-PEG6-C2-MMAD | 1.96 | site-specific | 89 | 0.374 | 0.285 |
| m7E6 TG6 amino-PEG6-C2-MMAD | 1.99 | site-specific | 92 | 0.748 | 0.598 |
| m7E6 LCQ04/K222R amino-PEG6-C2-MMAD | 1.97 | site-specific | 87 | 0.356 | 0.256 |
| m7E6 N297Q/K222R amino-PEG6-C2-MMAD | 3.83 | site-specific | 94 | 0.205 | 0.176 |

TABLE 3-continued

| ADC | DAR | Conjugation | Maximum % cytotoxicity | 50% cytotoxicity (nM) | EC50 (nM) |
|---|---|---|---|---|---|
| m7E6 N297Q/K222R/LCQ04 amino-PEG6-C2-MMAD | 5.85 | site-specific | 95 | 0.144 | 0.135 |
| m7E6 N297Q/K222R/LCQ04/TG6 amino-PEG6-C2-MMAD | 7.71 | site-specific | 96 | 0.120 | 0.106 |
| m7E6 N297Q/K222R/LCQ04/H7c amino-PEG6-C2-MMAD | 7.76 | site-specific | 95 | 0.067 | 0.062 |
| m7E6 N297Q/K222R/LCQ04/L11b amino-PEG6-C2-MMAD | 7.80 | site-specific | 95 | 0.080 | 0.077 |
| m7E6 maleimido-PEG6-C2-MMAD | 7.20 | conventional | 96 | 0.090 | 0.089 |

Example 2

Cytotoxicity of Increasingly Higher Loaded, Site-Specifically Conjugated Anti-Trop-2-ADCs in Cells with Moderate Expression of the Target (Colo205, Trop2+)

This example illustrates the in vitro cytotoxicity of higher loaded ADCs (site-specific and conventional) in medium target expressing Colo205 cells.

In vitro cytotoxicity studies of chimeric anti-Trop2 antibodies m7E6 H7c amino-PEG6-C2-MMAD (DAR 1.96, site-specific), m7E6 L11b amino-PEG6-C2-MMAD (DAR 1.96, site-specific), m7E6 TG6 amino-PEG6-C2-MMAD (DAR 1.99, site-specific), m7E6 LCQ04/K222R amino-PEG6-C2-MMAD (DAR 1.97, site-specific), m7E6 N297Q/K222R amino-PEG6-C2-MMAD (DAR 3.83, site-specific), m7E6 N297Q/K222R/LCQ04 amino-PEG6-C2-MMAD (DAR 5.85, site-specific), m7E6 N297Q/K222R/LCQ04/TG6 amino-PEG6-C2-MMAD (DAR 7.71, site-specific), m7E6 N297Q/K222R/LCQ04/H7c amino-PEG6-C2-MMAD (DAR 7.76, site-specific), m7E6 N297Q/K222R/LCQ04/L11b amino-PEG6-C2-MMAD (DAR 7.80, site-specific), and m7E6 maleimido-PEG6-C2-MMAD (DAR 7.20, conventional) were performed with target-expressing Colo205 cells; Colo205 is a cancer cell line with moderate target expression levels (Trop-2+). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. The results of the cytotoxicity assay are shown in FIG. 2 and summarized in Table 4. ADCs with DAR of 5.85 and above achieved full cell killing. The three site specific molecules with DAR of 7.71 (m7E6 N297Q/K222R/LCQ04/TG6 amino-PEG6-C2-MMAD), 7.76 (m7E6 N297Q/K222R/LCQ04/H7c amino-PEG6-C2-MMAD) and 7.80 (m7E6 N297Q/K222R/LCQ04/L11b amino-PEG6-C2-MMAD) compared well with the conventionally conjugated ADC with a DAR of 7.20 (m7E6 maleimido-PEG6-C2-MMAD).

These results show that increased cell killing activity and potency positively correlate with payload loading of the ADCs on medium target expressing Colo205 cells. Only the higher loaded molecules (e.g., DAR of 5.85 or above) could achieve full cell killing.

TABLE 4

| ADC | DAR | Conjugation | Maximum % cytotoxicity | 50% cytotoxicity (nM) | EC50 (nM) |
|---|---|---|---|---|---|
| m7E6 H7c amino-PEG6-C2-MMAD | 1.96 | site-specific | 49 | 384.42 | n/a |
| m7E6 L11b amino-PEG6-C2-MMAD | 1.96 | site-specific | 39 | not reached | n/a |
| m7E6 TG6 amino-PEG6-C2-MMAD | 1.99 | site-specific | 66 | 44.43 | n/a |
| m7E6 LCQ04/K222R amino-PEG6-C2-MMAD | 1.97 | site-specific | 38 | not reached | n/a |
| m7E6 N297Q/K222R amino-PEG6-C2-MMAD | 3.83 | site-specific | 86 | 3.040 | n/a |
| m7E6 N297Q/K222R/LCQ04 amino-PEG6-C2-MMAD | 5.85 | site-specific | 97 | 0.597 | 0.563 |

TABLE 4-continued

| ADC | DAR | Conjugation | Maximum % cytotoxicity | 50% cytotoxicity (nM) | EC50 (nM) |
|---|---|---|---|---|---|
| m7E6 N297Q/K222R/LCQ04/ TG6 amino-PEG6-C2-MMAD | 7.71 | site-specific | 98 | 0.395 | 0.409 |
| m7E6 N297Q/K222R/LCQ04/ H7c amino-PEG6-C2-MMAD | 7.76 | site-specific | 98 | 0.247 | 0.241 |
| m7E6 N297Q/K222R/LCQ04/ L11b amino-PEG6-C2-MMAD | 7.80 | site-specific | 98 | 0.405 | 0.410 |
| m7E6 maleimido-PEG6-C2-MMAD | 7.20 | conventional | 98 | 0.107 | 0.104 |

Example 3

Cytotoxicity of Increasingly Higher Loaded, Site-Specifically Conjugated Anti-Trop-2-ADCs in Cells with Low Expression of the Target (CF-PAC1, Trop2 (+))

This example illustrates the in vitro cytotoxicity of higher loaded site-specific ADCs in low target expressing CF-PAC1 cells.

In vitro cytotoxicity studies of chimeric anti-Trop2 antibodies m7E6 H7c amino-PEG6-C2-MMAD (DAR 1.96, site-specific), m7E6 L11b amino-PEG6-C2-MMAD (DAR 1.96, site-specific), m7E6 TG6 amino-PEG6-C2-MMAD (DAR 1.99, site-specific), m7E6 LCQ04/K222R amino-PEG6-C2-MMAD (DAR 1.97, site-specific), m7E6 N297Q/K222R amino-PEG6-C2-MMAD (DAR 3.83, site-specific), m7E6 N297Q/K222R/LCQ04 amino-PEG6-C2-MMAD (DAR 5.85, site-specific), m7E6 N297Q/K222R/LCQ04/TG6 amino-PEG6-C2-MMAD (DAR 7.71, site-specific), m7E6 N297Q/K222R/LCQ04/H7c amino-PEG6-C2-MMAD (DAR 7.76, site-specific), m7E6 N297Q/K222R/LCQ04/L11b amino-PEG6-C2-MMAD (DAR 7.80, site-specific) and m7E6 maleimido-PEG6-C2-MMAD (DAR 7.20, conventional) were performed with target-expressing CF-PAC1 cells; CF-PAC1 is a cancer cell line with low target expression levels (Trop-2 (+)). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (e.g., cytotoxicity) occurred were calculated by GraphPad Prism 5 software and expressed as concentration (nM), the maximum cell killing observed at the highest concentration of ADC tested is expressed as percentage of untreated control. Table 5 and FIG. 3 show that increased cell killing activity and potency positively correlate with payload loading of the ADCs on low target expressing CF-PAC1 cells, e.g., the higher the payload loading, the higher the cell killing activity. The three site-specific molecules with DAR of 7.71 (m7E6 N297Q/K222R/LCQ04/TG6 amino-PEG6-C2-MMAD), 7.76 (m7E6 N297Q/K222R/LCQ04/H7c amino-PEG6-C2-MMAD) and 7.80 (m7E6 N297Q/K222R/LCQ04/L11b amino-PEG6-C2-MMAD) compared well with the conventionally conjugated ADC with a DAR of 7.20 (m7E6 maleimido-PEG6-C2-MMAD).

This example also demonstrates that increased cell killing activity and potency positively correlate with payload loading of the ADCs on cells such as low target expressing CF-PAC1 cells.

TABLE 5

| ADC | DAR | Conjugation | Maximum % cytotoxicity | 50% cytotoxicity (nM) | EC50 (nM) |
|---|---|---|---|---|---|
| m7E6 H7c amino-PEG6-C2-MMAD | 1.96 | site-specific | −6 | not reached | n/a |
| m7E6 L11b amino-PEG6-C2-MMAD | 1.96 | site-specific | 1 | not reached | n/a |
| m7E6 TG6 amino-PEG6-C2-MMAD | 1.99 | site-specific | 7 | not reached | n/a |
| m7E6 LCQ04/K222R amino-PEG6-C2-MMAD | 1.97 | site-specific | 2 | not reached | n/a |
| m7E6 N297Q/K222R amino-PEG6-C2-MMAD | 3.83 | site-specific | 12 | not reached | n/a |
| m7E6 N297Q/K222R/LCQ04 amino-PEG6-C2-MMAD | 5.85 | site-specific | 22 | not reached | n/a |

TABLE 5-continued

| ADC | DAR | Conjugation | Maximum % cytotoxicity | 50% cytotoxicity (nM) | EC50 (nM) |
|---|---|---|---|---|---|
| m7E6 N297Q/K222R/LCQ04/ TG6 amino-PEG6-C2-MMAD | 7.71 | site-specific | 34 | not reached | n/a |
| m7E6 N297Q/K222R/LCQ04/ H7c amino-PEG6-C2-MMAD | 7.76 | site-specific | 37 | not reached | n/a |
| m7E6 N297Q/K222R/LCQ04/ L11b amino-PEG6-C2-MMAD | 7.80 | site-specific | 27 | not reached | n/a |
| m7E6 maleimido-PEG6-C2-MMAD | 7.20 | conventional | 48 | not reached | n/a |

Example 4

Cytotoxicity of Increasingly Higher Loaded, Site-Specifically Conjugated Anti-Trop-2-ADCs in Cells with No Expression of the Target (SW620, Trop2−)

This example illustrates the in vitro non-specific cytotoxicity of higher loaded site-specific ADCs in non-target expressing SW620 cells.

In vitro cytotoxicity studies of chimeric anti-Trop2 antibodies m7E6 TG6 amino-PEG6-C2-MMAD (DAR 1.99, site-specific), m7E6 LCQ04/K222R amino-PEG6-C2-MMAD (DAR 1.88, site-specific), m7E6 N297Q/K222R amino-PEG6-C2-MMAD (DAR 3.92, site-specific), m7E6 N297Q/K222R/LCQ04 amino-PEG6-C2-MMAD (DAR 5.85, site-specific), m7E6 N297Q/K222R/LCQ04/TG6 amino-PEG6-C2-MMAD (DAR 7.71, site-specific), m7E6 N297Q/K222R/LCQ04/H7c amino-PEG6-C2-MMAD (DAR 7.76, site-specific), m7E6 N297Q/K222R/LCQ04/L11b amino-PEG6-C2-MMAD (DAR 7.80, site-specific) and m7E6 maleimido PEG6-C2-MMAD (DAR 7.20, conventional) were performed with non target-expressing SW620 cells; SW620 is a cancer cell line with no expression of the target (Trop-2−). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. In this example, the starting concentration of the ADCs was increased over thirteen fold compared to the other in vitro examples from 266 nM to 3500 nM in order to determine if there was a non-target dependent cytotoxic effect of the ADCs. The results of the cytotoxicity assay are shown in FIG. 4 and summarized in Table 6. The three site specific molecules with DAR of 7.71 (m7E6 N297Q/K222R/LCQ04/TG6 amino-PEG6-C2-MMAD), 7.76 (m7E6 N297Q/K222R/LCQ04/H7c amino-PEG6-C2-MMAD) and 7.80 (m7E6 N297Q/K222R/LCQ04/L11b amino-PEG6-C2-MMAD) were significantly less nonspecifically cytotoxic compared to the conventionally conjugated ADC with a DAR of 7.20.

These results show that at higher ADC concentration, non-target dependent cytotoxicity was observed, and that this was lower in the site-specific ADCs relative to the conventional conjugates.

TABLE 6

| ADC | DAR | Conjugation | Maximum % cytotoxicity | 50% cytotoxicity (nM) | EC50 (nM) |
|---|---|---|---|---|---|
| m7E6 TG6 amino-PEG6-C2-MMAD | 1.99 | site-specific | 38 | not reached | n/a |
| m7E6 LCQ04/K222R amino-PEG6-C2-MMAD | 1.88 | site-specific | 10 | not reached | n/a |
| m7E6 N297Q/K222R amino-PEG6-C2-MMAD | 3.92 | site-specific | 46 | not reached | n/a |
| m7E6 N297Q/K222R/LCQ04 amino-PEG6-C2-MMAD | 5.85 | site-specific | 48 | not reached | n/a |
| m7E6 N297Q/K222R/LCQ04/ TG6 amino-PEG6-C2-MMAD | 7.71 | site-specific | 63 | 2173.2 | 1456.0 |

TABLE 6-continued

| ADC | DAR | Conjugation | Maximum % cytotoxicity | 50% cytotoxicity (nM) | EC50 (nM) |
|---|---|---|---|---|---|
| m7E6 N297Q/K222R/LCQ04/ H7c amino-PEG6-C2-MMAD | 7.76 | site-specific | 66 | 2108.9 | 1401.0 |
| m7E6 N297Q/K222R/LCQ04/ L11b amino-PEG6-C2-MMAD | 7.80 | site-specific | 70 | 1472.1 | 1044.0 |
| m7E6 maleimido-PEG6-C2-MMAD | 7.20 | conventional | 79 | 270.5 | 197.2 |

Example 5

Side-by-Side Comparison of Cytotoxicity of Increasingly Higher Loaded, Site-Specifically Conjugated Vs. Conventionally Conjugated Anti-Trop-2-ADCs in Cells with Moderate Expression of the Target (Colo205, Trop2+)

This example illustrates the in vitro increased cytotoxicity and potency of higher loaded site-specific ADCs in medium target expressing Colo205 cells.

In vitro cytotoxicity studies of chimeric anti-Trop2 antibodies m7E6 maleimido-PEG65-C2-MMAD (DAR 4.13, conventional), m7E6 N297Q/K222R amino-PEG6-C2-MMAD (DAR 3.86, site-specific), m7E6 maleimido-PEG6-C2-MMAD (DAR 6.09, conventional), m7E6 N297Q/LCQ04/K222R amino-PEG6-C2-MMAD (DAR 5.86, site specific), m7E6 maleimido-PEG6-C2-MMAD (DAR 7.80, conventional), m7E6 N297Q/K222R/LCQ04/H7c amino-PEG6-C2-MMAD (DAR 7.77, site-specific) and control IgG N297Q/LCQ04/K222R amino-PEG6-C2-MMAD (DAR 5.84, site-specific) were performed with target-expressing Colo205 cells; Colo205 is a cancer cell line with moderate target expression levels (Trop-2+). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (e.g., cytotoxicity) occurred were calculated by GraphPad Prism 5 software and expressed as concentration (nM), the maximum cell killing observed at the highest concentration of ADC tested is expressed as percentage of untreated control. The results of the cytotoxicity assay are shown in FIG. 5 and summarized in Table 7. The three site specific molecules with DAR of 3.86 (m7E6 N297Q/K222R amino-PEG6-C2-MMAD), 5.86 (m7E6 N297Q/LCQ04/K222R amino-PEG6-C2-MMAD) and 7.77 (m7E6 N297Q/K222R/LCQ04/H7c amino-PEG6-C2-MMAD) compared well with the conventionally conjugated ADC with a DAR of 4.13 (m7E6 maleimido-PEG6-C2-MMAD), 6.09 (m7E6 maleimido-PEG6-C2-MMAD) and 7.80 (m7E6 maleimido-PEG6-C2-MMAD), respectively.

These results show that increased cell killing activity and potency positively correlate with payload loading of the ADCs on medium target expressing Colo205 cells (e.g., the higher loaded the molecule, the higher the potency).

TABLE 7

| ADC | DAR | Conjugation | Maximum % cytotoxicity | 50% cytotoxicity (nM) | EC50 (nM) |
|---|---|---|---|---|---|
| m7E6 maleimido-PEG6-C2-MMAD | 4.13 | conventional | 86 | 7.61 | 4.23 |
| m7E6 N297Q/K222R amino-PEG6-C2-MMAD | 3.86 | site-specific | 71 | 8.80 | 2.23 |
| m7E6 maleimido-PEG6-C2-MMAD | 6.09 | conventional | 89 | 3.67 | 1.81 |
| m7E6 N297Q/LCQ04/K222R amino-PEG6-C2-MMAD | 5.86 | site-specific | 82 | 2.34 | 1.24 |
| m7E6 maleimido-PEG6-C2-MMAD | 7.80 | conventional | 94 | 0.28 | 0.24 |
| m7E6 N297Q/K222R/LCQ04/ H7c amino-PEG6-C2-MMAD | 7.77 | site-specific | 88 | 0.82 | 0.65 |
| control IgG N297Q/LCQ04/K222R amino-PEG6-C2-MMAD | 5.84 | site-specific | 6 | not reached | n/a |

Example 6

An Anti-Trop-2 7E6 Site-Specific Auristatin Conjugate with a Drug Antibody Ratio of 7.76 Induced Long Term Tumor Stasis in Colo205 Xenograft Model This example illustrates the efficacy of the higher loaded site-specific ADCs in Colo205 Xenograft model.

In vivo efficacy studies of m7E6 N297Q/K222R/LCQ04/H7c amino-PEG6-C2-MMAD (DAR 7.76, site-specific), m7E6 maleimido-PEG6-C2-MMAD (DAR 7.20), conventional), m7E6 N297Q/K222R amino-PEG6-C2-MMAD (DAR 3.92, site-specific) and control IgG N297Q/K222R amino-PEG6-C2-MMAD (DAR 3.68, site-specific were performed with target-expressing Colo205 xenograft model; Colo205 is a cancer cell line with moderate target expression levels (Trop-2+). Three million Colo205 cancer cells were implanted subcutaneously into 5-8 weeks old nu/nu mice until the tumor sizes reached around 250 mm$^3$. Animals were randomized by tumor sizes, and dosing was done through bolus tail vein injection. 6 mg/kg of mAbs were administered through bolus tail vein injection for a total of 1 dose. Tumor volume was measured twice a week by a Caliper device and calculated with the following formula: Tumor volume=(length×width2)/2. Animals were euthanized if their tumor volumes reached 2000 mm$^3$ or if they lost more than 20% of their body weight. FIG. 6 shows that single dose of the site-specific DAR 7.76 conjugate resulted in long term tumor stasis, significantly outperforming the conventional DAR7.2 conjugate.

Figure 11:
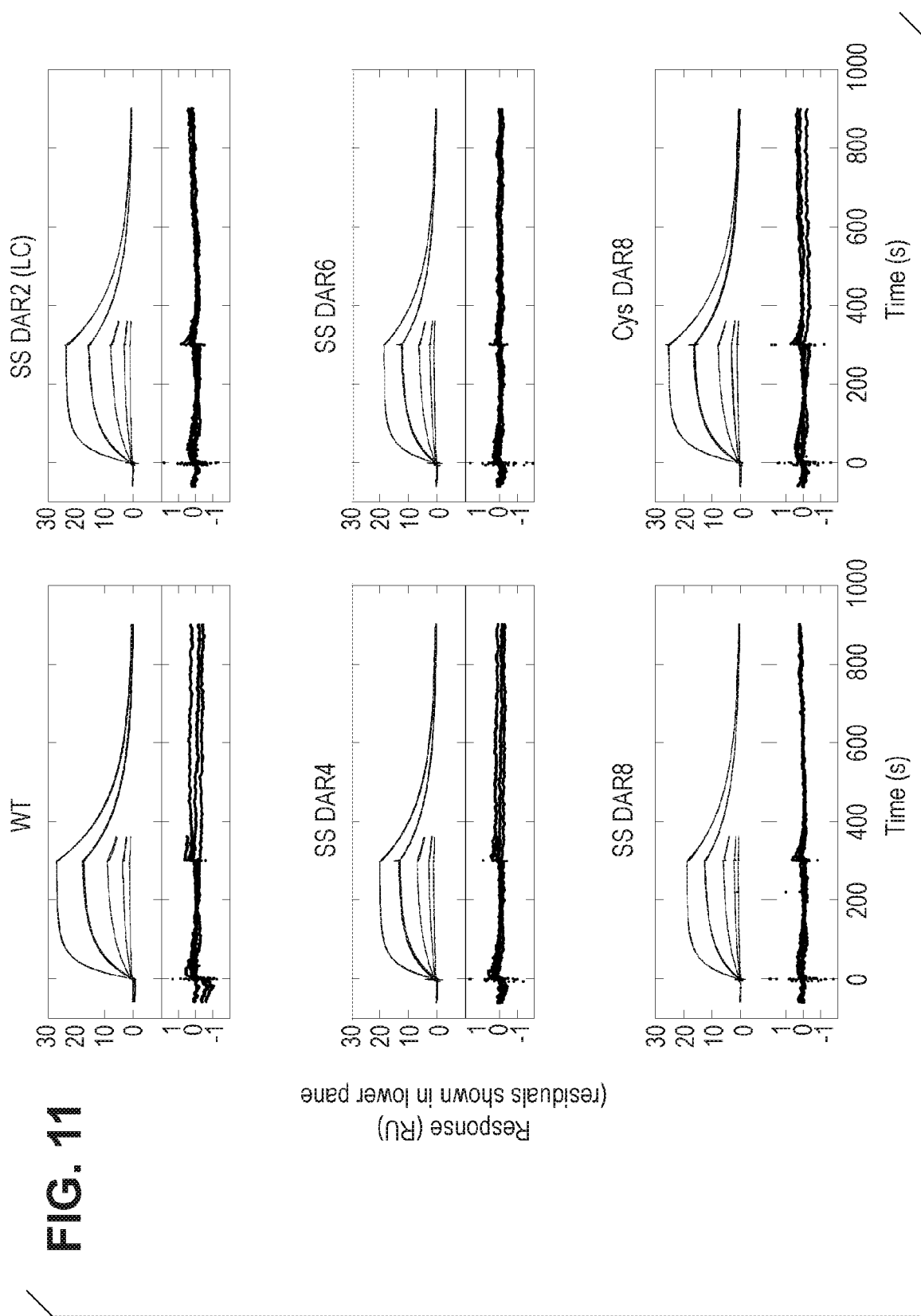
FIG. 11 shows kinetics analysis of the target/IgG interactions in various ADCs, including WT (m7E6-non-conjugated), SS DAR2 (LC) (site-specific m7E6 LCQ04 amino-PEG6-C2-MMAD), SS DAR4 (m7E6 N297Q/K222R amino-PEG6-C2-MMAD), SS DAR6 (m7E6 N297Q/K222R/LCQ04 amino-PEG6-C2-MMAD), SS DAR8 (m7E6 N297Q/K222R/LCQ04/H7c amino-PEG6-C2-MMAD), and Cys DAR8 (m7E6 maleimido PEG6-C2-MMAD). Each panel represents a global analysis of a given IgG with the target (human Trop2) concentrations of 1.2, 3.7, 11, 33, and 100 nM. The black lines represent the measured data, and the red lines represent the global fits; the residuals are shown below each overlay plot.

Further, the difference in potency between the site-specific and the conventional high DAR conjugates was not due to differential target binding of the ADCs, as all ADCs showed similar binding kinetics. FIG. 11 and Table 8. The binding kinetics of target/IgG interactions as shown in FIG. 11 and Table 8 were determined by using the Biacore T200 Surface Plasmon Resonance biosensor (GE Lifesciences, Piscataway N.J.).

TABLE 8

| Conjugate | k$_a$ (1/Ms) | k$_d$ (1/s) | t$_{1/2}$ (min) | K$_D$ (nM) |
|---|---|---|---|---|
| WT | 2.2E+05 | 7.0E−03 | 1.6 | 33 |
| SS DAR2 (LC) | 2.1E+05 | 6.5E−03 | 1.8 | 31 |
| SS DAR4 | 2.2E+05 | 7.0E−03 | 1.7 | 31 |
| SS DAR6 | 2.1E+05 | 6.8E−03 | 1.7 | 32 |
| SS DAR8 | 2.1E+05 | 6.3E−03 | 1.8 | 31 |
| Cys DAR8 | 1.9E+05 | 6.5E−03 | 1.8 | 34 |

WT (m7E6-non-conjugated),
SS DAR2 (LC) ((site-specific) m7E6 LCQ04 amino-PEG6-C2-MMAD),
SS DAR4 (m7E6 N297Q/K222R amino-PEG6-C2-MMAD),
SS DAR6 (m7E6 N297Q/K222R/LCQ04 amino-PEG6-C2-MMAD),
SS DAR8 (m7E6 N297Q/K222R/LCQ04/H7c amino-PEG6-C2-MMAD), and
Cys DAR8 (m7E6 maleimido PEG6-C2-MMAD)

Taken together, this example demonstrates that the ADC of the present invention (e.g., DAR at 7.76) is more efficacious in inducing long term tumor stasis than the conventional ADC with a similar or higher DAR, and that an ADC with DARs lower than 5 is essentially non-efficacious in this model.

Example 7

Anti-Trop-2 7E6 Site-Specific Auristatin Conjugates with a Drug Antibody Ratio of 5.86 and 7.77 are More Effective than the Corresponding Conventional Conjugates and Induced Long Term Tumor Stasis in Colo205 Xenograft Model This example also illustrates the efficacy of the higher loaded site-specific ADCs in Colo205 Xenograft model.

In vivo efficacy studies of m7E6 maleimido-PEG6-C2-MMAD (DAR 4.13, conventional), m7E6 N297Q/K222R amino-PEG6-C2-MMAD (DAR 3.86, site-specific), m7E6 maleimido-PEG6-C2-MMAD (DAR 6.09, conventional), m7E6 N297Q/LCQ04/K222R amino-PEG6-C2-MMAD (DAR 5.86, site-specific), m7E6 maleimido-PEG6-C2-MMAD (DAR 7.80, conventional), m7E6 N297Q/K222R/LCQ04/H7c amino-PEG6-C2-MMAD (DAR 7.77, site-specific) and control IgG N297Q/LCQ04/K222R amino-PEG6-C2-MMAD (DAR 5.84, site-specific) were performed with target-expressing Colo205 xenograft model; Colo205 is a cancer cell line with moderate target expression levels (Trop-2+). Three million Colo205 cancer cells were implanted subcutaneously into 5-8 weeks old nu/nu mice until the tumor sizes reached around 200 mm$^3$. Animals were randomized by tumor sizes, and dosing was done through bolus tail vein injection. 6 mg/kg of mAbs were administered through bolus tail vein injection for a total of 1 dose. Tumor volume was measured twice a week by a Caliper device and calculated with the following formula: Tumor volume=(length×width2)/2. Animals were euthanized if their tumor volumes reached 2000 mm$^3$ or if they lost more than 20% of their body weight. FIG. 7 shows that a single dose of the site-specific DAR 5.86 (m7E6 N297Q/LCQ04/K222R amino-PEG6-C2-MMAD) and site-specific DAR 7.77 (m7E6 N297Q/K222R/LCQ04/H7c amino-PEG6-C2-MMAD) conjugates resulted in long term tumor growth stasis, significantly outperforming the conventional DAR 6.09 (m7E6 maleimido-PEG6-C2-MMAD) and DAR 7.80 (m7E6 maleimido-PEG6-C2-MMAD) conjugates. The difference in potency was not due to differential target binding of the ADCs, as all ADCs showed similar binding kinetics, as discussed in Example 6.

Accordingly, this example also demonstrates that the ADCs of the present invention (e.g., site-specific DAR at 5.86 and 7.77) are more efficacious in inducing long term tumor stasis than the conventional ADC with a similar DAR.

Example 8

Anti-Trop-2 7E6 Site-Specific Auristatin Conjugates with High Drug Antibody Ratio Show Better Pharmacokinetic (PK) Profile in Comparison to the Conventional ADCs This example illustrates the PK profiles for the higher loaded site-specific ADCs in comparison to the conventional higher loaded ADCs in both mice and rats.

Pharmacokinetic studies of the ADCs of the present invention were carried out in both mice and rats and analyzed using ELISA (Enzyme-Linked Immunosorbent Assay) and the DAR was analysed by LC/MS (Liquid Chromatography-Mass Spectometry).

Total Antibody PK Assay

Each well of a 96-well microtiter plate (NUNC) was coated with 100 uL of goat anti-human IgG antibody, Fc specific (Pierce, Rockford, Ill.) at 1 ug/mL in 1×PBS (Cell Gro). The plates were incubated at 4-8° C. overnight. All washing steps were performed with a Biotek ELx405 plate washer with 1×PBS/0.05% Tween. After washing 3 times, plates were blocked with 200 uL of assay buffer (1×PBS/ 0.5% BSA/0.05% Polysorbate 20) and incubated for 1-2 hours at room temperature with gentle agitation. Plates were washed 3 times and 100 uL of standards, controls and samples diluted 1:100 in assay buffer were added to the corresponding wells. After a two-hour incubation with gentle agitation at room temperature, plates were washed 6 times before dispensing 100 uL of the detection antibody (anti-human IgG, Fab specific, HRP-labeled from Sigma (St Louis, Mo.) diluted to 250 ng/mL in assay buffer. The plates were incubated for one more hour with gentle agitation at room temperature before washing 6 times. Then 100 uL of TMB (3,3',5,5'-tetramethylbenzidine) (KPL, Gaithersburg, Md.) was added to each well. Color development was allowed for approximately 5 minutes before stopping the reaction with 100 uL of 1M Phosphoric acid. Absorbance was measured at 450 nm with a reference at 650 nm on a SpectraMax 340 plate reader (Molecular Devices). SoftMax Pro 5.2 software was used to fit standard curves with a 4-parameter regression and calculate sample concentrations.

ADC PK Assay

Each well of a 96-well microtiter plate (NUNC) was coated with 100 uL of goat anti-human IgG antibody at 2 ug/mL in 1×PBS (Cell Gro). The plates were incubated at 4-8° C. overnight. All washing steps were performed on a Biotek ELx405 platewasher with 1×PBS/0.05% Tween. After washing 3 times, plates were blocked with 200 uL/well of assay buffer (1×PBS/0.5% BSA/0.05% Polysorbate 20) and incubated for 1-2 hours at room temperature with gentle agitation. Plates were washed 3 times and 100 uL of standards, controls and samples diluted 1:100 in assay buffer were added in duplicate to the corresponding wells. After a two-hour incubation with gentle agitation at room temperature, plates were washed 6 times before dispensing 100 uL of the detection antibody (biotinylated anti-MMAD monoclonal antibody) diluted to 4 ug/mL in assay buffer. The plates were incubated for 1.5 hours with gentle agitation at room temperature before washing 6 times. Avidin-HRP (Vector Labs, Burlingame, Calif.) was diluted to 0.5 ug/mL in assay buffer and 100 uL was dispensed into each well. Plates were incubated for another hour before washing 6 times. Then 100 uL of TMB (KPL, Gaithersburg, Md.) was added to each well. Color development was allowed for approximately 5 minutes before stopping the reaction with 100 uL of 1M Phosphoric acid. Absorbance was measured at 450 nm with a reference at 650 nm on a SpectraMax 340 plate reader (Molecular Devices, Downingtown, Pa.). SoftMax Pro 5.2 software was used to fit standard curves with a 4-parameter regression and calculate sample concentrations.

LC/MS Intact Mass Analysis of ADC and DAR Calculation

Prior to LC/MS analysis, ADCs (site specific DAR6 and DAR8 and conventional DAR8) were deglycosylated with PNGase F (New England Biolabs Inc., Ipswich, Mass.) under non-denaturing conditions at 37° C. overnight. ADCs (1 μg) were loaded into a reverse phase column packed with a polymeric material (Michrom-Bruker, Fremont, Calif.). LC/MS analysis was performed using Agilent 1100 series HPLC system, comprising binary HPLC pump, degasser, temperature controlled auto sampler, column heater and diode-array detector (DAD), coupled to an Orbitrap Velos Pro (Thermo Fisher Scientific, Somerset, N.J.) mass spectrometer with electrospray ion source. The mobile phases were comprised of solvent A (water 0.1% formic acid) and solvent B (acetonitrile 0.1% formic acid). The HPLC was carried out using an increasing gradient of solvent B over a 30 min run, consisting of isocratic flow of 3% solvent B for 10 min, followed by a gradient up to 97% solvent B over 1 min, held at 97% solvent B for 2 min and followed finally with a equilibration step at 3% solvent B for 17 min. The resulting mass spectra were deconvoluted using ProMass software (Thermo Fisher Scientific, Somerset, N.J.). For site specific ADC, the DAR was calculated using the intact mass of the ADC; For conventional ADC the DAR was calculated from the deconvoluted spectra of the heavy and light chain since conventional ADC lacks intermolecular disulfide bonds and the chains separate under reverse phase conditions. The DAR calculation is based on the relative intensity of the observed DAR species.

In Vivo Studies

Figure 8A:
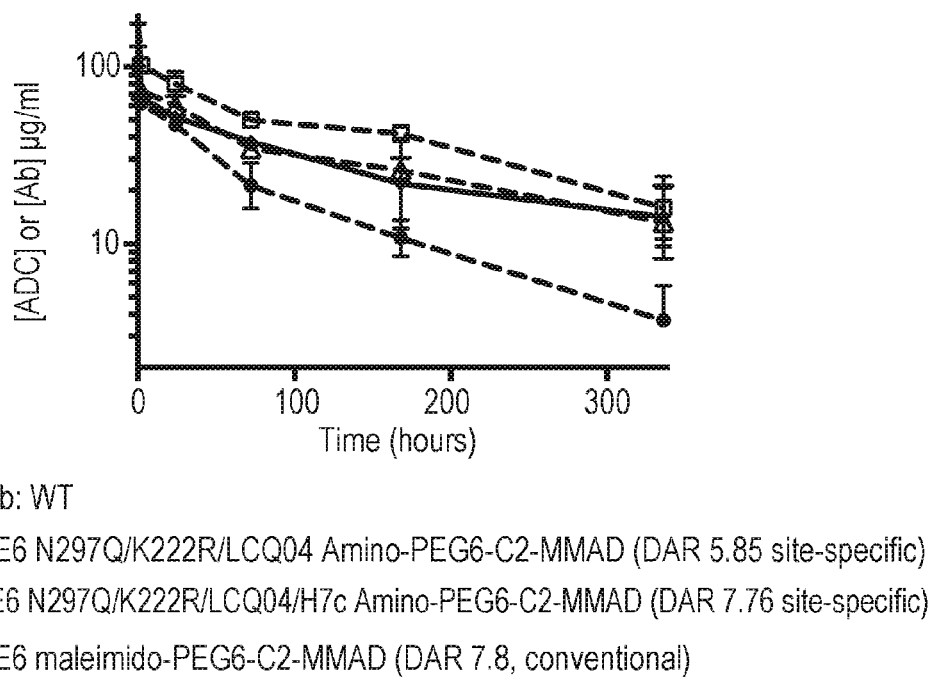
FIGS. 8(a)-8(h) show the PK profiles in mice and rats of the higher loaded site-specific ADCs of the present invention in comparison to the unconjugated wild-type antibody and the conventional ADCs with a similar DAR.
Figure 8B:
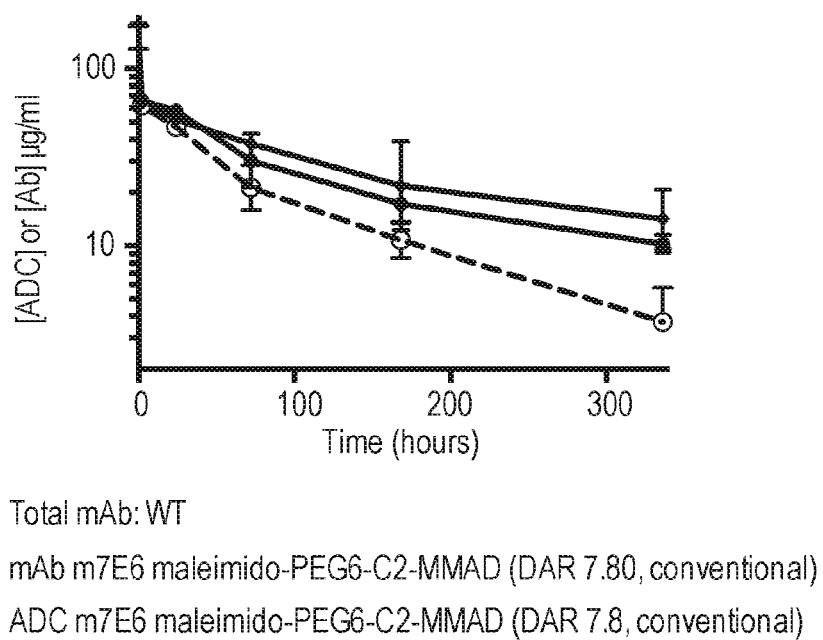
Figure 8C:
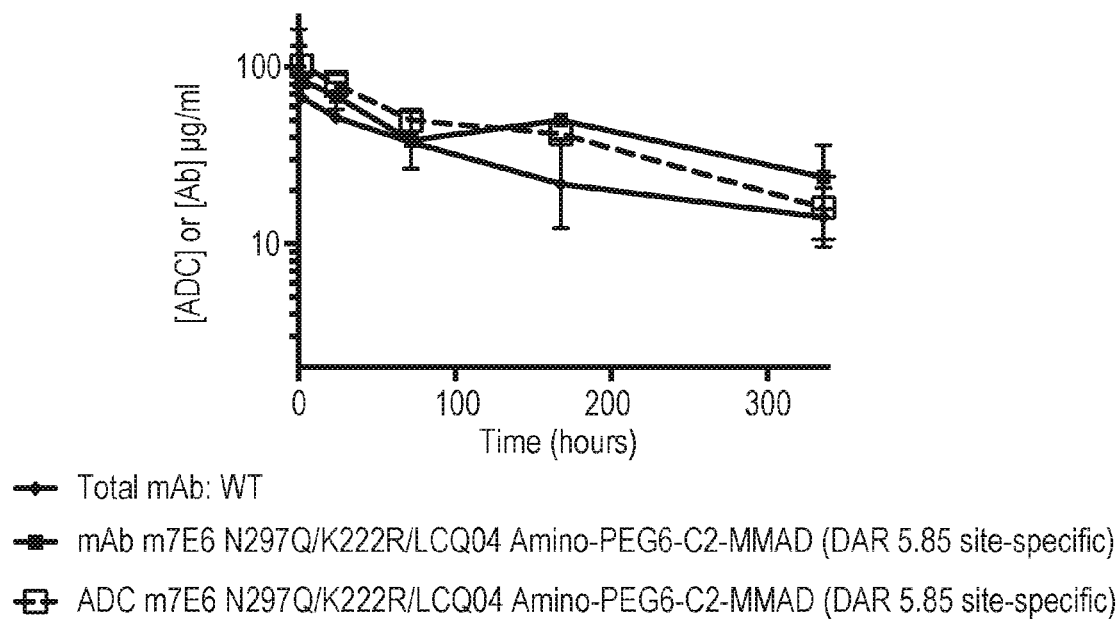
Figure 8D:
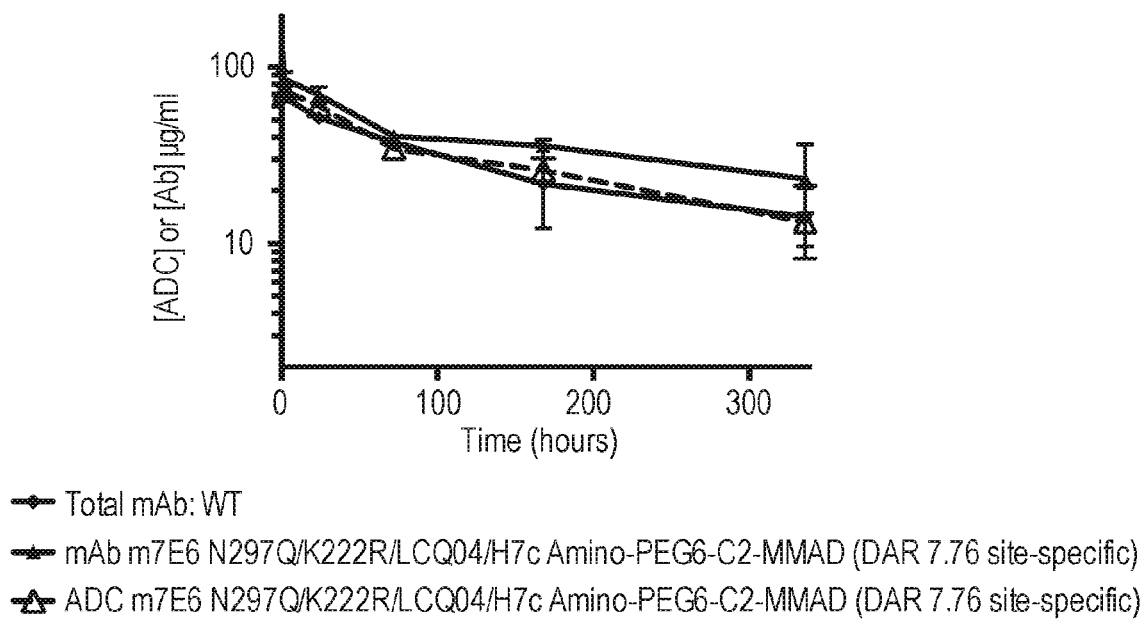

In mice, a single dose (6 mg/kg) of all ADCs was tested in the Colo205 Xenograft model. Under these conditions, antibody m7E6 conjugated to PEG6MMAD as (1) m7E6 N297Q/K222R/LCQ04 amino-PEG6-C2-MMAD (DAR 5.85, site-specific); and 2) m7E6 N297Q/K222R/LCQ04/ H7c amino-PEG6-C2-MMAD (DAR 7.76, site-specific) showed a similar pharmacokinetic profile to the unconjugated wild-type antibody m7E6. Comparison of the total mAb and ADC signals revealed that higher loaded ADCs (mAb or ADC m7E6 N297Q/K222R/LCQ04 amino-PEG6-C2-MMAD (DAR 5.85, site-specific); or mAb or ADC m7E6 N297Q/K222R/LCQ04/H7c amino-PEG6-C2-MMAD (DAR 7.76, site-specific) showed very little payload loss over the two-week period. See FIGS. 8(c) and 8(d). The data indicate that the transglutaminase mediated linkage of amino-PEG6-C2-MMAD results in stable conjugates. In contrast, antibody m7E6 conjugated to maleimido-PEG6-C2-MMAD using the conventional method (m7E6 maleimido-PEG6-C2-MMAD (DAR 7.8) displayed lower ADC exposure relative to both the total mAb and the unconjugated antibody, suggesting loss of payload. See FIG. 8(b). Loss of payload from maleimide-based conjugates has been described previously (see, e.g., Alley et al., *Bioconj. Chem.* 19(3):759-765 (2008); and Shen et al., *Nat. Biotechnol.* 30(2):184-189 (2012)) and is thought to occur through the retro-Michael addition mechanism. The difference in ADC exposure between the conventional conjugates with DAR 8 and ADC conjugates of the present invention is likely responsible for the inferior activity of the conventional ADC conjugates in-vivo.

The decrease in exposure seen in the ELISA assays for the conventional ADCs might be potentiated by the possibility that the ADC assay used in these experiments underestimated the loss of payload from an antibody. More specifically, the ADC ELISA showed a signal not only for DAR 8, but also all other species with lower loading that were generated in-vivo. This effect was more pronounced for higher loaded species, as for ADC with DAR 8 using the conventional conjugation method, there could be up to seven drugs lost without significant change in the ELISA signal. Further, for non-cleavable conventional conjugates such as m7E6 maleimido-PEG6-C2-MMAD (DAR 8), loss of drug was likely the main reason for low in-vivo potency. In contrast, the non-cleavable ADC conjugates of the present invention (e.g., DAR 6 or DAR 8) do not suffer from maleimide instability, and are able to significantly inhibit tumor growth in the moderate target expressing Colo205 Xenograft model.

Figure 8E:
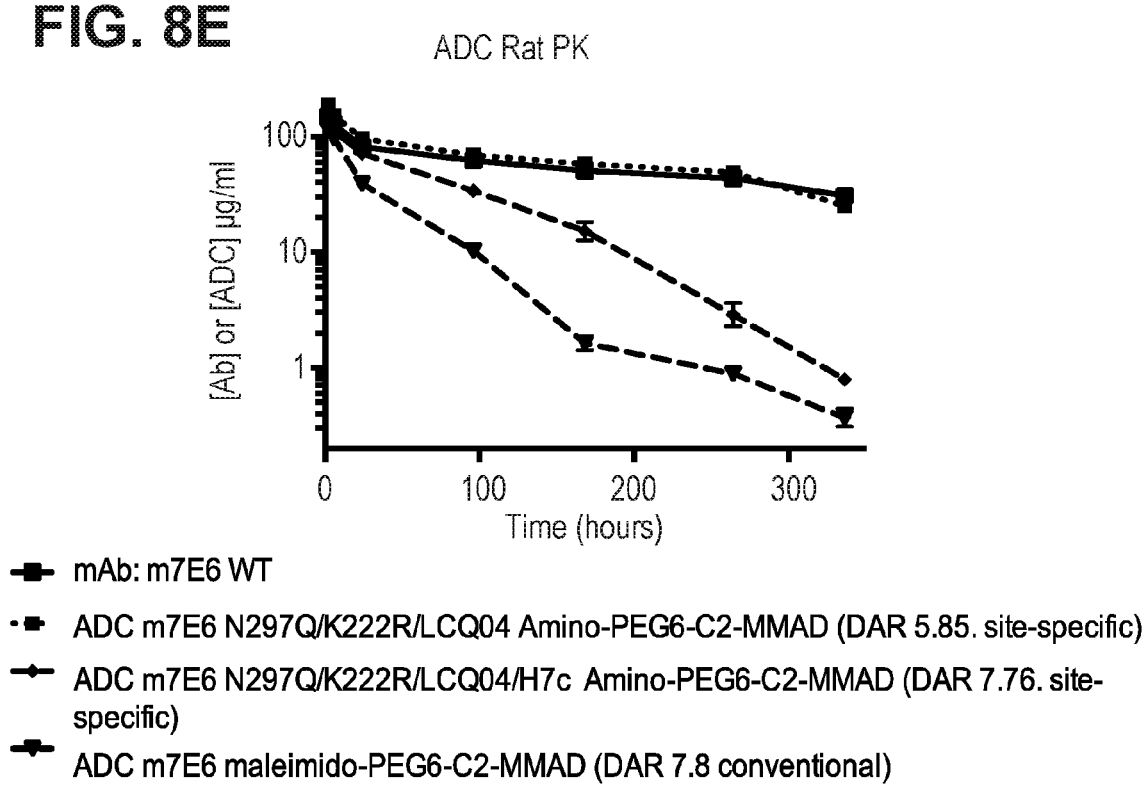
Figure 8F:
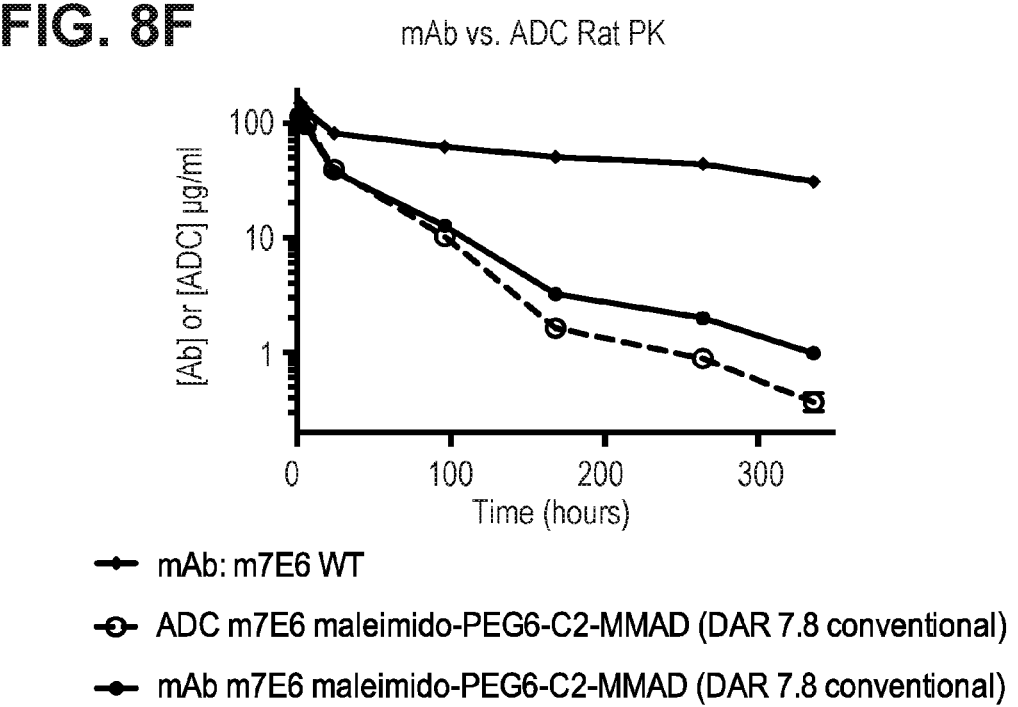
Figure 8G:
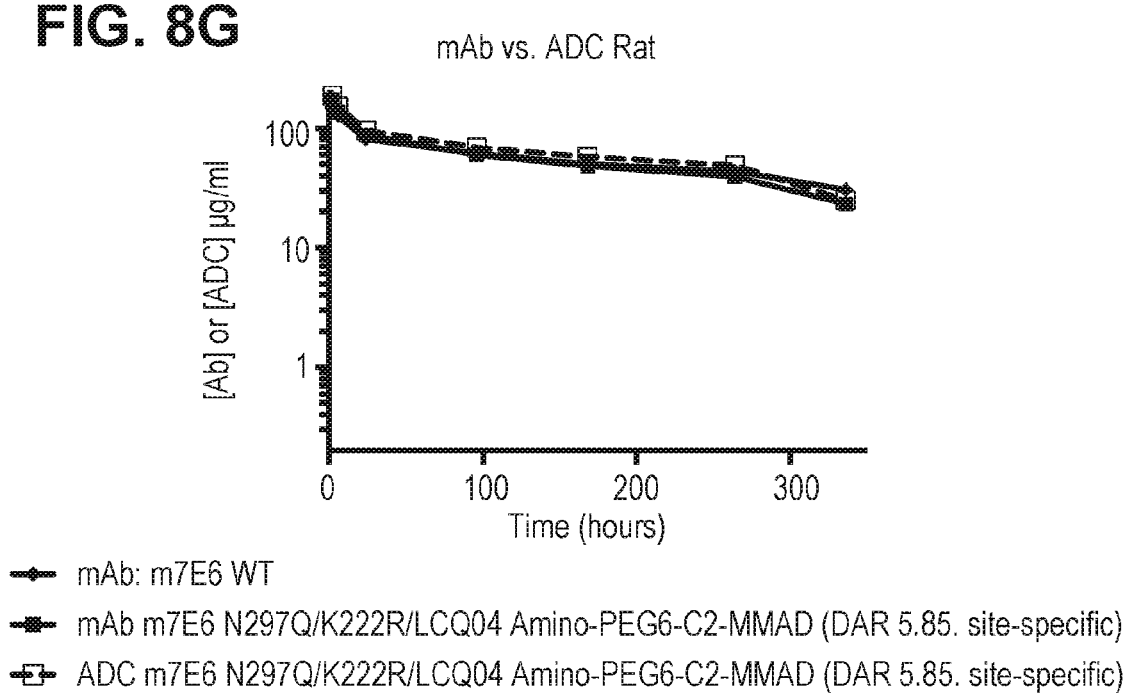
Figure 8H:
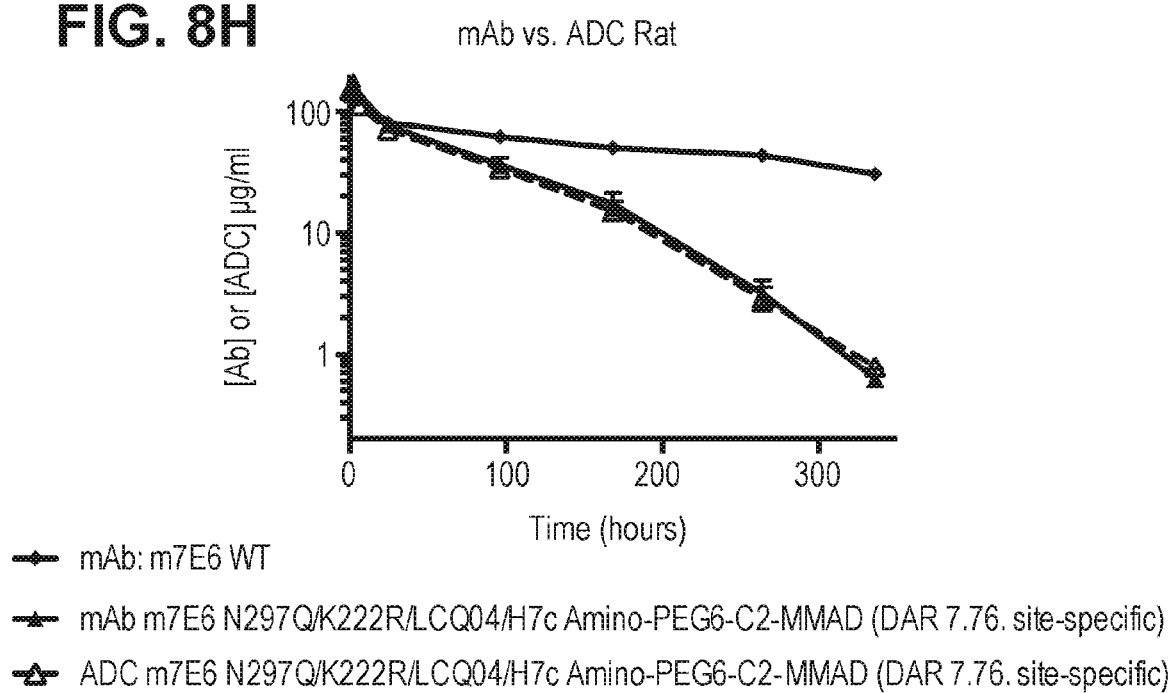

The PK studies of the higher loaded ADCs were also carried out in rats to compare to mice. ADCs based on the conventional conjugation method (m7E6 maleimido-PEG6-C2-MMAD (DAR 7.8)) still had the lowest levels of ADC in circulation. See FIG. 8(e). ADCs of the present invention with DAR 8 (e.g., m7E6 N297Q/K222R/LCQ04/H7c amino-PEG6-C2-MMAD (DAR 7.76 site-specific)) showed intermediate levels of ADCs in circulation, and ADCs of the present invention with DAR 6 (e.g., m7E6 N297Q/K222R/LCQ04 PEG6MMAD (DAR 5.85, site-specific)) showed the highest levels of ADCs in circulation that were comparable to the unconjugated m7E6 antibody. See FIG. 8(e). The conventional ADCs with DAR 7.8 showed the largest differences to the unconjugated antibody where both the total antibody as well as the ADC had much reduced exposures compared to the unconjugated antibody levels. See FIG. 8(f). In the case of m7E6 N297Q/K222R/LCQ04 PEG6MMAD (DAR 5.85, site-specific), the total mAb levels and ADC levels were nearly equivalent to the unconjugated antibody levels. See FIG. 8(g). The total mAb as well as the ADC levels for m7E6 N297Q/K222R/LCQ04/H7c PEG6MMAD were reduced relative to the unconjugated antibody FIG. 8(h). This is in contrast to the PK results from mice, wherein the DAR8 ADC of the present invention showed unconjugated antibody-like PK. These results suggest that combining conjugation sites that individually display wild-type PK can result in decrease of exposure.

Figure 12A:
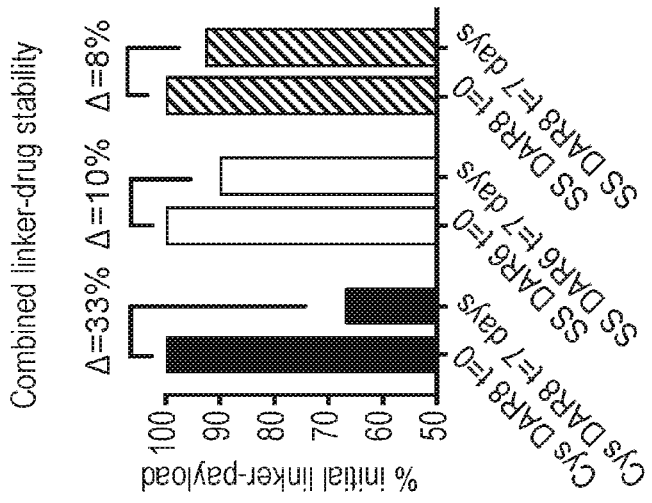
FIGS. 12(a)-12(c) show the linker and/or payload stability analysis by mass-spectrometry from mouse in vivo samples. The figures compare linker stability (FIG. 12(a)), drug stability (FIG. 12(b); Conjugated MMAD C-terminus stability), and combined linker-drug stability (FIG. 12(c)) between the conventionally conjugated ADC with a DAR 8 and high loaded site-specific ADCs with a DAR 6 and DAR 8. "Cys DAR8" represents m7E6 maleimido PEG6-C2-MMAD; "SS DAR6" represents m7E6 N297Q/K222R/LCQ04 amino-PEG6-C2-MMAD; and SS "DAR8_1" represents m7E6 N297Q/K222R/LCQ04/H7c amino-PEG6-C2-MMAD.
Figure 12B:
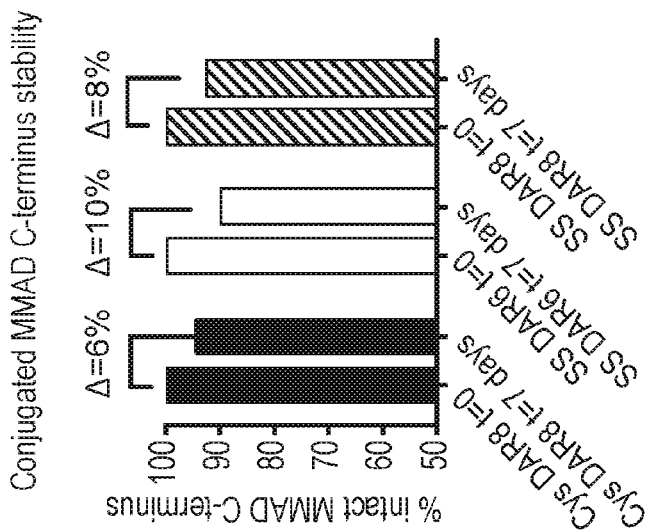
Figure 12C:
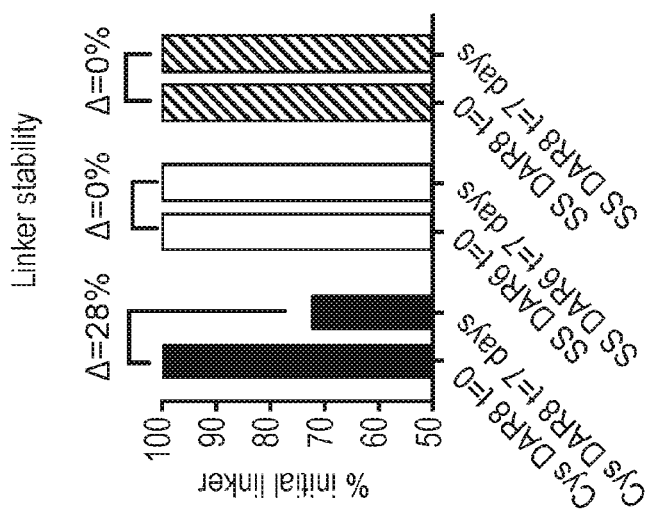

Mass spectrometry analysis of mouse in-vivo samples further revealed that the conventional ADC (e.g., m7E6 maleimido-PEG6-C2-MMAD) has about 28% loss of linker-payload, while the transglutaminase linker remains intact in both the site-specific conjugates DAR6 (m7E6 N297Q/K222R/LCQ04 PEG6MMAD) and DAR8_1 (m7E6 N297Q/K222R/LCQ04/H7c amino-PEG6-C2-MMAD). See FIG. 12(a). The mass spectrometry study also revealed a C-terminal degradation of the drug MMAD which have similar levels in the site-specific DAR6, SS DAR8_1 and conventional DAR8 conjugates (FIG. 12(b)). The combined linker-payload stability of the conjugates is shown in FIG. 12(c).

Taken together, this example demonstrates that higher loaded ADCs of the present invention has similar PK profiles to the unconjugated wild-type antibody in mice, and better PK profiles than the higher-loaded conventional ADCs in rats.

Example 9

Combining ADC Conjugation Sites that Individually Display Wild-Type Pharmacokinetic Profiles can Result in Decrease of Exposure in Rats This example illustrates the PK profiles for the higher loaded site-specific ADCs with different combinations of conjugation sites in rats.

Figure 9A:
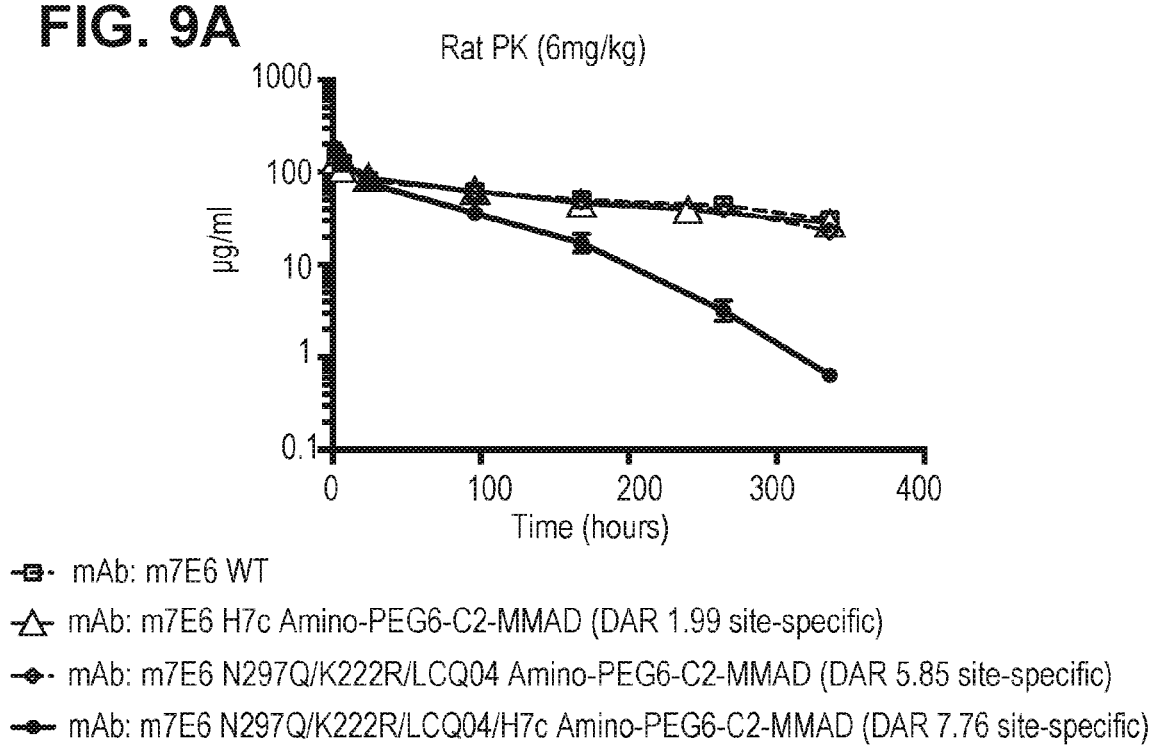
FIGS. 9(a)-9(b) show the PK profiles in rats of the higher loaded site-specific ADCs of the present invention with DARs 7.76 and 7.7 at different combinations of conjugation sites.
Figure 9B:
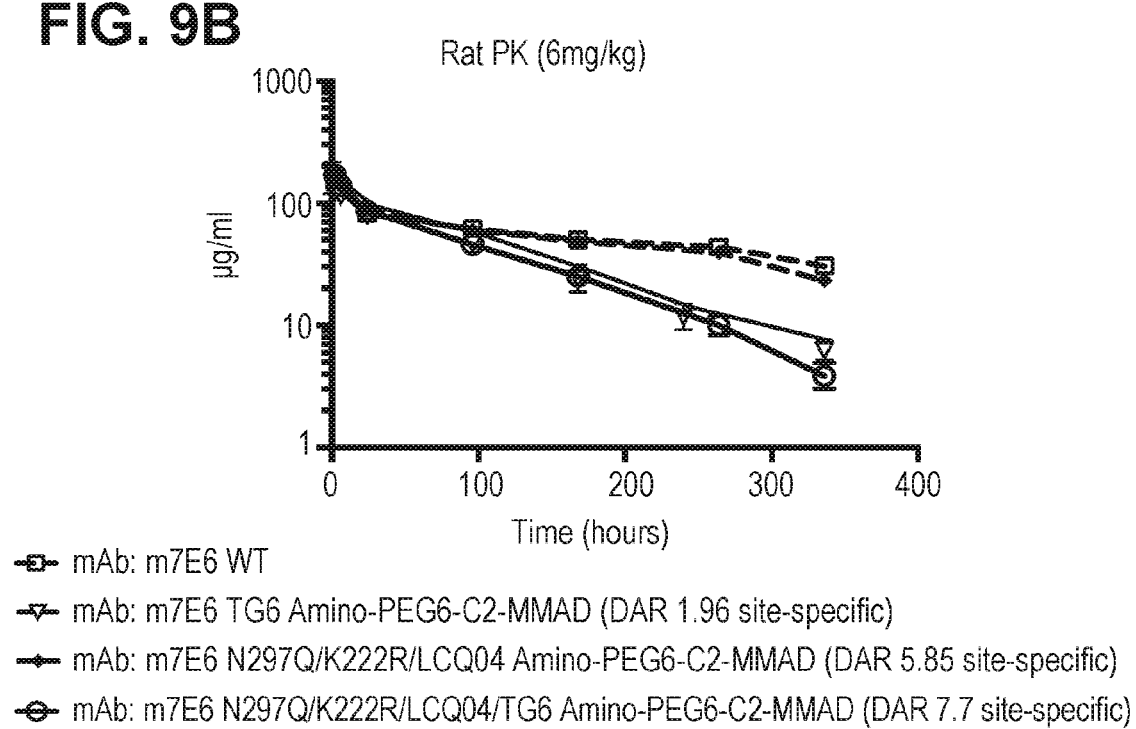

The PK studies of the higher loaded ADCs having different combinations of conjugation sites were also carried out in rats. Site-specific ADC with DAR 7.76 (m7E6 N297Q/K222R/LCQ04/H7c Amino-PEG6-C2-MMAD) was created by combining site-specific ADC with DAR 1.99 (m7E6 H7c Amino-PEG6-C2-MMAD) with site-specific ADC with DAR 5.85 (m7E6 N297Q/K222R/LCQ04 Amino-PEG6-C2-MMAD). Site-specific ADCs with DAR 5.85 and 1.99 showed wild-type PK profiles in rats individually, but showed reduced exposure when combined together as site-specific ADC with DAR 7.76. See FIG. 9(a). In comparison, when the same site-specific ADC with DAR 5.85 (m7E6 N297Q/K222R/LCQ04 Amino-PEG6-C2-MMAD) was combined with a different site-specific ADC with DAR 1.96 (m7E6 TG6 Amino-PEG6-C2-MMAD; conjugation site at the C-terminus of the antibody heavy chain, which is far from the conjugation sites of m7E6 N297Q/K222R/LCQ04 Amino-PEG6-C2-MMAD), the resulting ADC (m7E6 N297Q/K222R/LCQ04/TG6 Amino-PEG6-C2-MMAD (DAR 7.7 site-specific)) displayed no additional decrease in exposure (e.g., no greater decrease than m7E6 TG6 Amino-PEG6-C2-MMAD). See FIG. 9(b).

The data suggest that too many hydrophobic payloads (e.g., MMAD) in close proximity may decrease the PK profile of ADCs in rats. The data also suggest that for conjugation sites that are distant from each other, the PK profile of the combined sites is similar to the shortest individual PK profile in rats.

Example 10

Safety and Tolerability of the Site-Specifically Conjugated Anti-Trop-2 7E6 Auristatin Conjugates in Comparison to the Conventional ADCs in Mice This example illustrates the safety and tolerability of the higher loaded site-specific ADCs in C57Bl/6 mice.

C57Bl/6 mice were given a single dose of 75, 125, or 200 mg/kg of conventionally conjugated ADC (m7E6 maleimido-PEG6-C2-MMAD "DAR8") or site-specific ADCs conjugated with PEG6-C2-MMAD non-cleavable payload (m7E6 N297Q/K222R/LCQ04 amino-PEG6-C2-MMAD ("DAR6") and m7E6 N297Q/K222R/LCQ04/TG6 amino-PEG6-C2-MMAD ("DAR8_1"). Clinical observations, body weight, pharmacokinetics, and clinical pathology parameters were evaluated. More specifically, animals were observed immediately and 2 hour after injection, then daily for two weeks post dose. Body weights were recorded on days 0, 2, 5, 7, 9, 12, and 14. Blood samples were taken for pharmacokinetics at 5 minutes, 7 days, and 14 days post dose and for clinical chemistry and hematology analyses on day 14

Figure 10A:
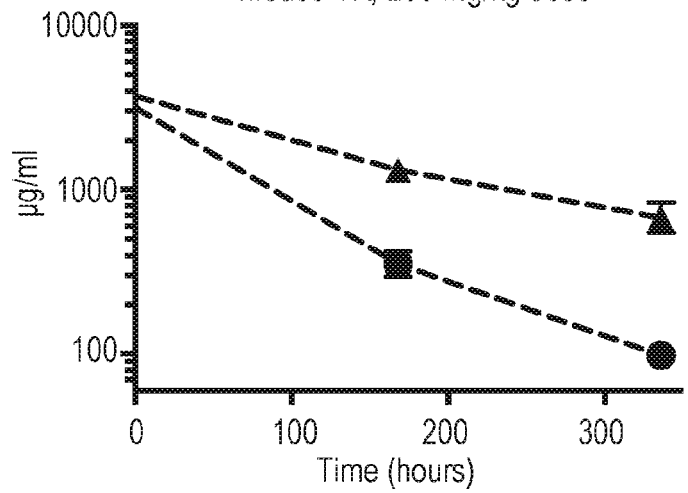
FIGS. 10(a)-10(d) show the toxicology of higher loaded ADCs in C57Bl/6 mice.
Figure 10B:
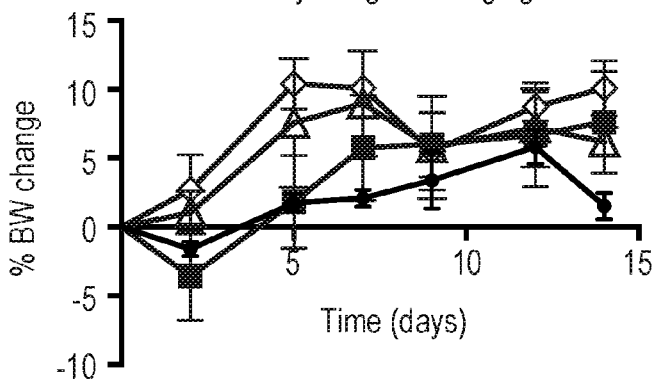
Figure 10C:
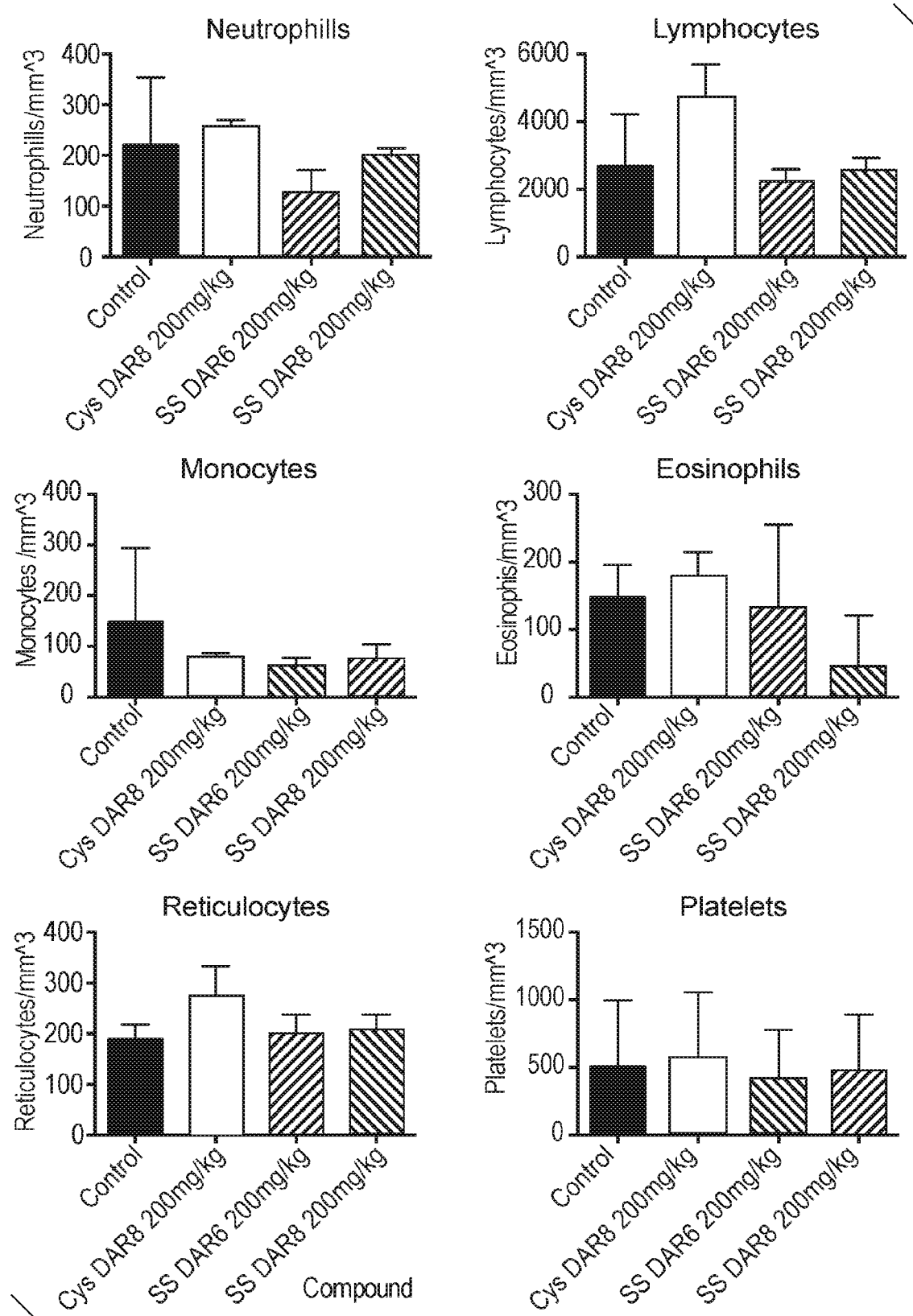
Figure 10D:
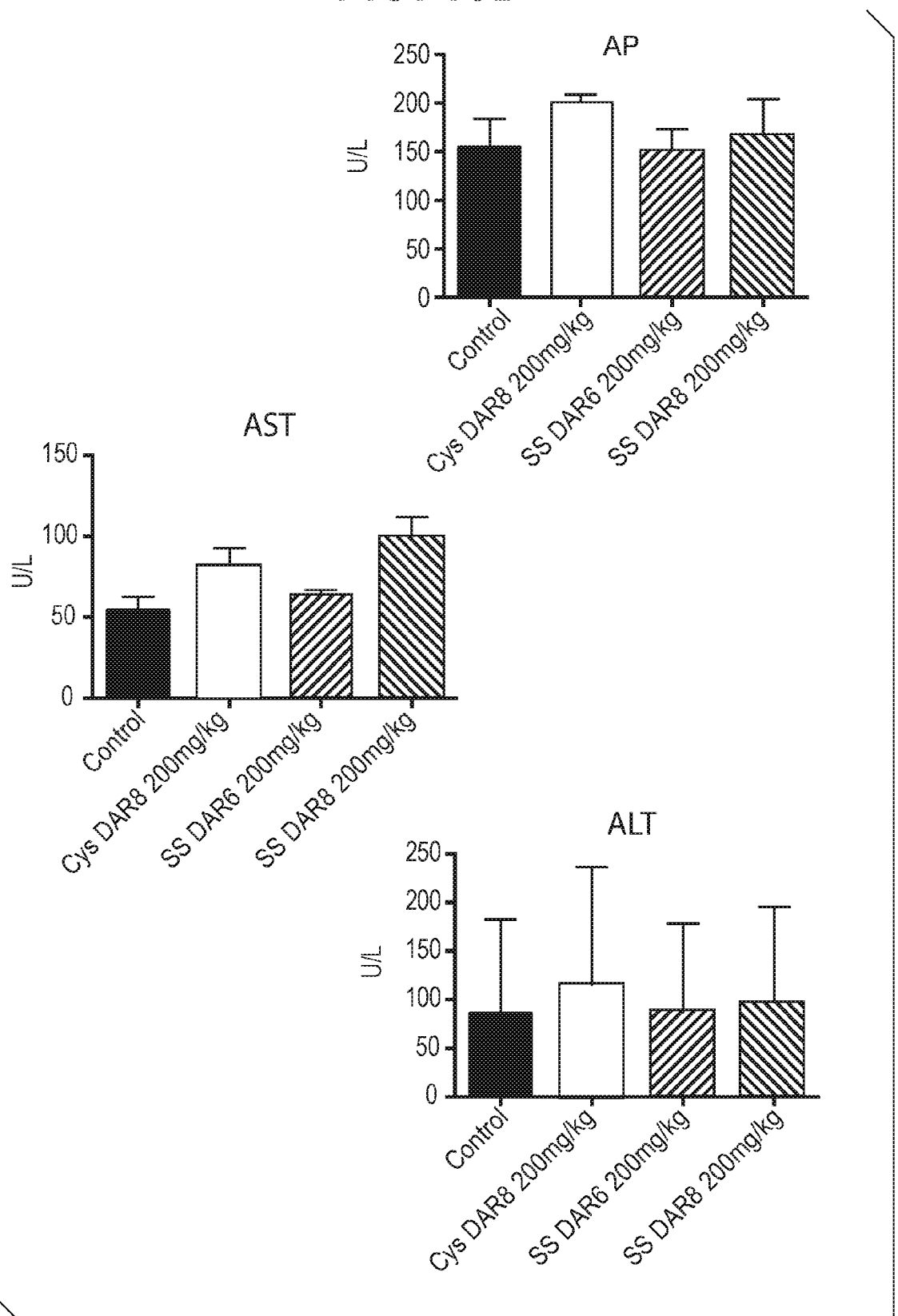

Both conventional and site-specific conjugates were tolerated up to a very high dose of 200 mg/kg. There were no clinical observations or meaningful changes in body weights indicating toxicity. FIG. 10(b). Clinical pathology parameters were evaluated at the end of the study (day 14) for all three conjugates (conventional ADC "DAR8" and two site-specific ADCs "DAR8_1" and "DAR6"), and no toxicologically meaningful or significant changes were observed. FIGS. 10(c) and 10(d). For example, there were no significant changes in liver enzymes aspartate aminotransferase [AST], alanine transaminase [ALT] and alkaline phosphatase [ALP]) and key hematological parameters (neutrophils, reticulocytes, and platelets).

Figure 13A:
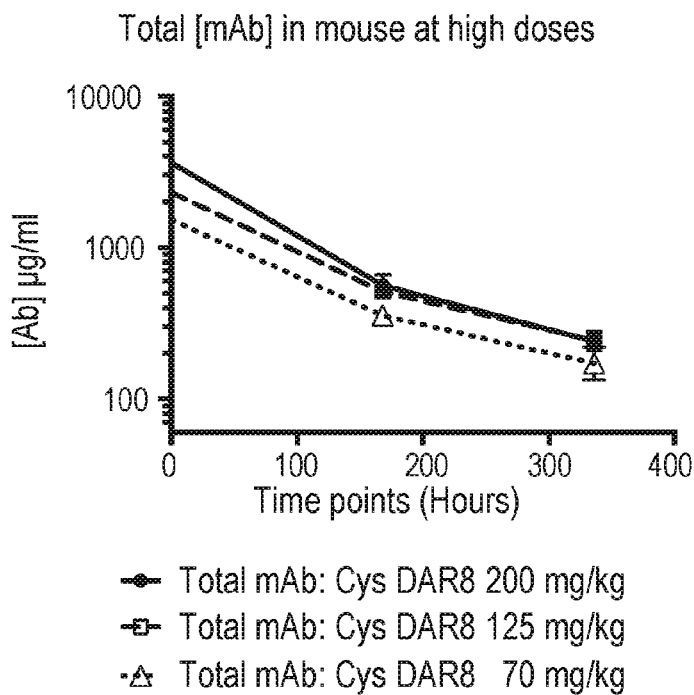
FIGS. 13(a)-13(b) show the toxicokinetics of conventionally conjugated ADC ("Cys DAR8": m7E6 maleimido PEG6-C2-MMAD) and high loaded site-specific ADCs DAR6 (m7E6 N297Q/K222R/LCQ04 amino-PEG6-C2-MMAD) and DAR8_1 (m7E6 N297Q/K222R/LCQ04/H7c amino-PEG6-C2-MMAD) in mice at various antibody concentration and measured at different time points.
Figure 13B:
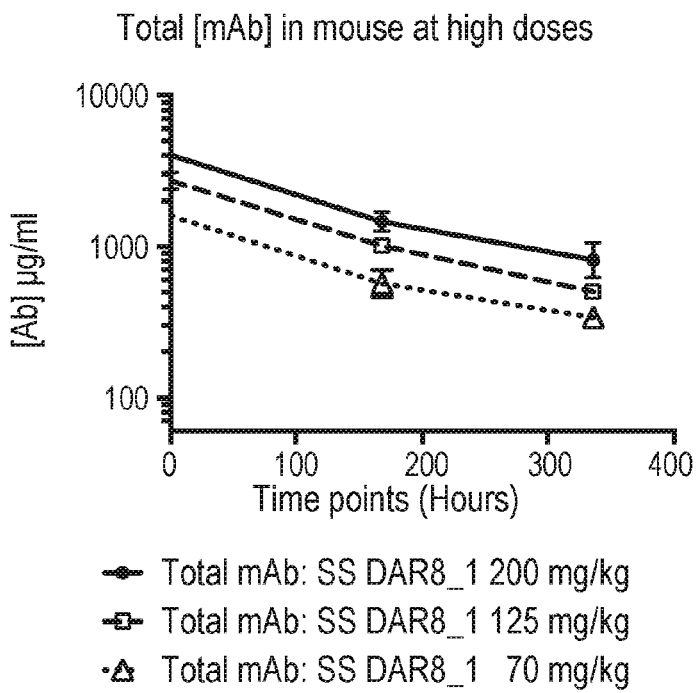

Collectively, the results indicate that both site-specific and conventional conjugates at high doses of 200 mg/kg with DAR of 8 and PEG6-C2-MMAD are well tolerated in mice. Further, relative to conventional DAR8 conjugate, site-specific DAR8_1 conjugate achieved approximately 55% higher exposure. FIG. 10(a). Further, the conventional conjugate with DAR8 also showed lower than expected antibody concentrations at high doses. FIG. 13(a). This phenomenon was not observed for the site-specific ADC DAR8_1, which showed the expected increase in exposure even at the highest tested dose of 200 mg/kg. FIG. 13(b).

Taken together, the site-specific conjugates exhibited a good safety profile with higher ADC exposure in comparison to the conventional conjugates.

Example 11

Cytotoxicity of Increasingly Higher Loaded, Site-Specifically Conjugated Anti-Trop-2-ADCs in Cells with High Expression of the Target (BxPC3, Trop2+++)

This example illustrates the in vitro cytotoxicity of higher loaded ADCs (e.g., DARs 5.95-9.4 (site-specific conjugation)) in high target expressing BxPC3 cells.

Figure 14:
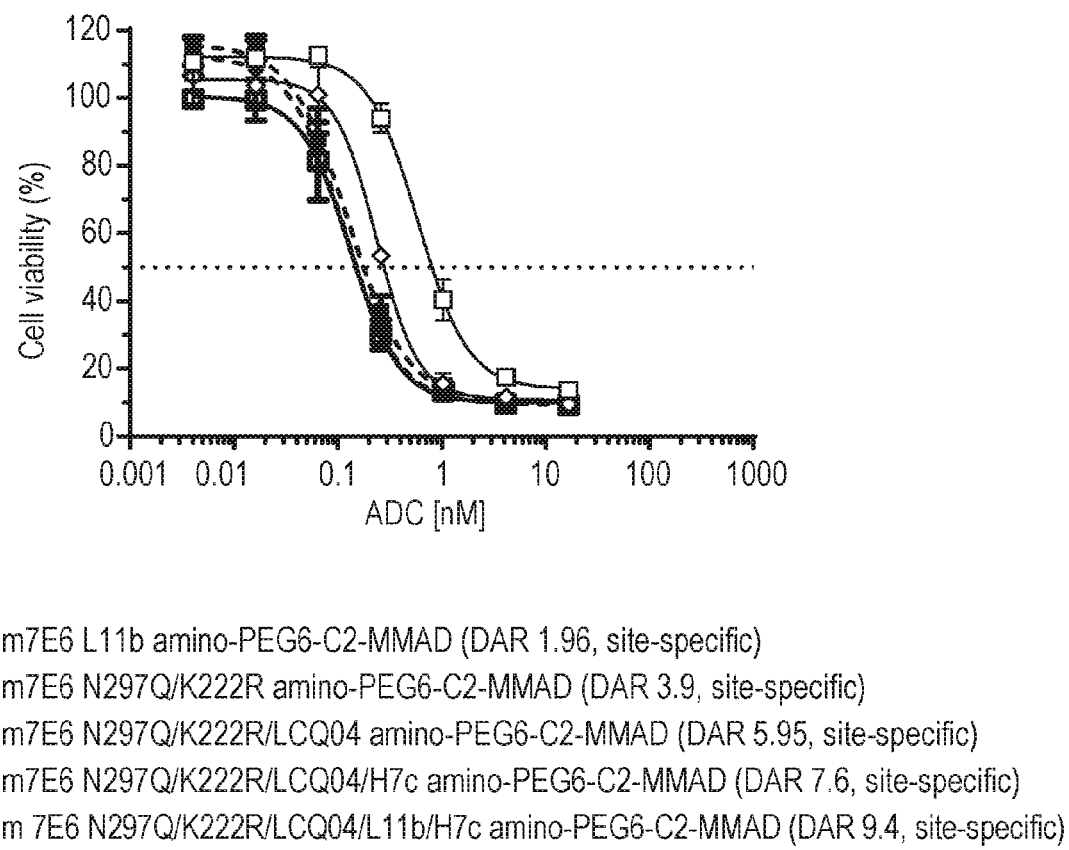
FIG. 14 shows the cytotoxicity of the site-specific ADCs with increasing DARs in the high target expressing BxPC3 cells in comparison to the site-specific ADCs with a lower DAR (e.g., 1.96 and 3.9).

In vitro cytotoxicity studies of chimeric anti-Trop2 antibodies m7E6 L11b amino-PEG6-C2-MMAD (DAR 1.96, site-specific), m7E6 N297Q/K222R amino-PEG6-C2-MMAD (DAR 3.9, site-specific), m7E6 N297Q/K222R/LCQ04 amino-PEG6-C2-MMAD (DAR 5.95, site-specific), m7E6 N297Q/K222R/LCQ04/H7c amino-PEG6-C2-MMAD (DAR 7.6, site-specific), and N297Q/K222R/LCQ04/L11b/H7c amino-PEG6-C2-MMAD (DAR9.4, site-specific) were performed with target-expressing BxPC3 cells. BxPc3 is a cancer cell line with high target expression levels (Trop-2+++). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. The results of the cytotoxicity assay are shown in FIG. 14 and summarized in Table 9. These results show that while all ADCs achieved near complete cell killing irrespective of their payload loading on high target expressing BxPC3 cells, the higher loaded conjugates were more potent in comparison to the lower loaded conjugates.

Example 12

Cytotoxicity of Increasingly Higher Loaded, Site-Specifically Conjugated Anti-Trop-2-ADCs in Cells with Moderate Expression of the Target (Colo205, Trop2+)

This example illustrates the in vitro cytotoxicity of higher loaded ADCs (e.g., DARs 5.95-9.4 (site-specific conjugation)) in medium target expressing Colo205 cells.

In vitro cytotoxicity studies of chimeric anti-Trop2 antibodies m7E6 L11b amino-PEG6-C2-MMAD (DAR 1.96, site-specific), m7E6 N297Q/K222R amino-PEG6-C2-MMAD (DAR 3.9, site-specific), m7E6 N297Q/K222R/LCQ04 amino-PEG6-C2-MMAD (DAR 5.95, site-specific), m7E6 N297Q/K222R/LCQ04/H7c amino-PEG6-C2-MMAD (DAR 7.6, site-specific), and N297Q/K222R/LCQ04/L11b/H7c amino-PEG6-C2-MMAD (DAR9.4, site-specific) were performed with target-expressing Colo205 cells; Colo205 is a cancer cell line with moderate target expression levels (Trop-2+). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. The results of the cytotoxicity assay are shown in FIG. 15 and summarized in Table 10. These results show that increased cell killing activity and potency positively correlate with payload loading of the ADCs on medium target expressing Colo205 cells. Only the higher loaded molecules (e.g., DAR of 5.95 or above) could achieve full cell killing.

TABLE 9

| ADC | DAR | Conjugation | Maximum % cytotoxicity | 50% cytotoxicity (nM) | EC50 (nM) |
|---|---|---|---|---|---|
| m7E6 L11b amino-PEG6-C2-MMAD | 1.96 | site-specific | 86 | 0.807 | 0.596 |
| m7E6 N297Q/K222R amino-PEG6-C2-MMAD | 3.90 | site-specific | 90 | 0.279 | 0.237 |
| m7E6 N297Q/K222R/LCQ04 amino-PEG6-C2-MMAD | 5.95 | site-specific | 90 | 0.178 | 0.128 |
| m7E6 N297Q/K222R/LCQ04/H7c amino-PEG6-C2-MMAD | 7.60 | site-specific | 91 | 0.151 | 0.116 |
| m7E6 N297Q/K222R/LCQ04/L11b/H7c amino-PEG6-C2-MMAD | 9.40 | site-specific | 91 | 0.150 | 0.132 |

This example also demonstrates that increasing the DAR to 9.4 with the conjugate N297Q/K222R/LCQ04/L11 b/H7c amino-PEG6-C2-MMAD resulted in increased potency over the conjugate m7E6 N297Q/K222R/LCQ04/H7c amino-PEG6-C2-MMAD with a DAR of 7.6.

TABLE 10

| ADC | DAR | Conjugation | Maximum % cytotoxicity | 50% cytotoxicity (nM) | EC50 (nM) |
|---|---|---|---|---|---|
| m7E6 L11b amino-PEG6-C2-MMAD | 1.96 | site-specific | 28 | not reached | n/a |
| m7E6 N297Q/K222R amino-PEG6-C2-MMAD | 3.90 | site-specific | 80 | 3.163 | n/a |
| m7E6 N297Q/K222R/LCQ04 amino-PEG6-C2-MMAD | 5.95 | site-specific | 89 | 0.715 | 0.521 |
| m7E6 N297Q/K222R/LCQ04/H7c amino-PEG6-C2-MMAD | 7.60 | site-specific | 93 | 0.383 | 0.315 |
| m7E6 N297Q/K222R/LCQ04/L11b/H7c amino-PEG6-C2-MMAD | 9.40 | site-specific | 93 | 0.154 | 0.128 |

Example 13

Cytotoxicity of Increasingly Higher Loaded, Site-Specifically Conjugated Anti-Trop-2-ADCs in Cells with Low Expression of the Target (CF-PAC1, Trop2 (+))

This example illustrates the in vitro cytotoxicity of higher loaded ADCs (e.g., DARs 5.95-9.4 (site-specific conjugation)) in low target expressing CF-PAC1 cells.

In vitro cytotoxicity studies of chimeric anti-Trop2 antibodies m7E6 L11b amino-PEG6-C2-MMAD (DAR 1.96, site-specific), m7E6 N297Q/K222R amino-PEG6-C2-MMAD (DAR 3.9, site-specific), m7E6 N297Q/K222R/LCQ04 amino-PEG6-C2-MMAD (DAR 5.95, site-specific), m7E6 N297Q/K222R/LCQ04/H7c amino-PEG6-C2-MMAD (DAR 7.6, site-specific), and N297Q/K222R/LCQ04/L11b/H7c amino-PEG6-C2-MMAD (DAR9.4, site-specific) were performed with target-expressing CF-PAC1 cells; CF-PAC1 is a cancer cell line with low target expression levels (Trop-2 (+)). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (e.g., cytotoxicity) occurred were calculated by GraphPad Prism 5 software and expressed as concentration (nM), the maximum cell killing observed at the highest concentration of ADC tested is expressed as percentage of untreated control. Table 11 and FIG. 16 show that increased cell killing activity and potency positively correlate with payload loading of the ADCs on low target expressing CF-PAC1 cells, e.g., the higher the payload loading, the higher the cell killing activity. The conjugate N297Q/K222R/LCQ04/L11b/H7c amino-PEG6-C2-MMAD with a DAR of 9.4 slightly increased the maximum cell killing activity.

This example also demonstrates that increased cell killing activity and potency positively correlate with payload loading of the ADCs on cells such as low target expressing CF-PAC1 cells.

TABLE 11

| ADC | DAR | Conjugation | Maximum % cytotoxicity | 50% cytotoxicity (nM) | EC50 (nM) |
|---|---|---|---|---|---|
| m7E6 L11b amino-PEG6-C2-MMAD | 1.96 | site-specific | 7 | not reached | n/a |
| m7E6 N297Q/K222R amino-PEG6-C2-MMAD | 3.90 | site-specific | 23 | not reached | n/a |
| m7E6 N297Q/K222R/LCQ04 amino-PEG6-C2-MMAD | 5.95 | site-specific | 32 | not reached | n/a |
| m7E6 N297Q/K222R/LCQ04/H7c amino-PEG6-C2-MMAD | 7.60 | site-specific | 42 | not reached | n/a |

TABLE 11-continued

| ADC | DAR | Conjugation | Maximum % cytotoxicity | 50% cytotoxicity (nM) | EC50 (nM) |
|---|---|---|---|---|---|
| m7E6 N297Q/K222R/LCQ04/ L11b/H7c amino-PEG6-C2-MMAD | 9.40 | site-specific | 49 | not reached | n/a |

Example 14

Cytotoxicity of Increasingly Higher Loaded, Site-Specifically Conjugated Anti-Trop-2-ADCs in Cells with No Expression of the Target (SW620, Trop2−)

This example illustrates the in vitro cytotoxicity of higher loaded ADCs (e.g., DAR 5.95 to 9.40 (site-specific conjugation)) in non-target expressing SW620 cells.

Figure 17:
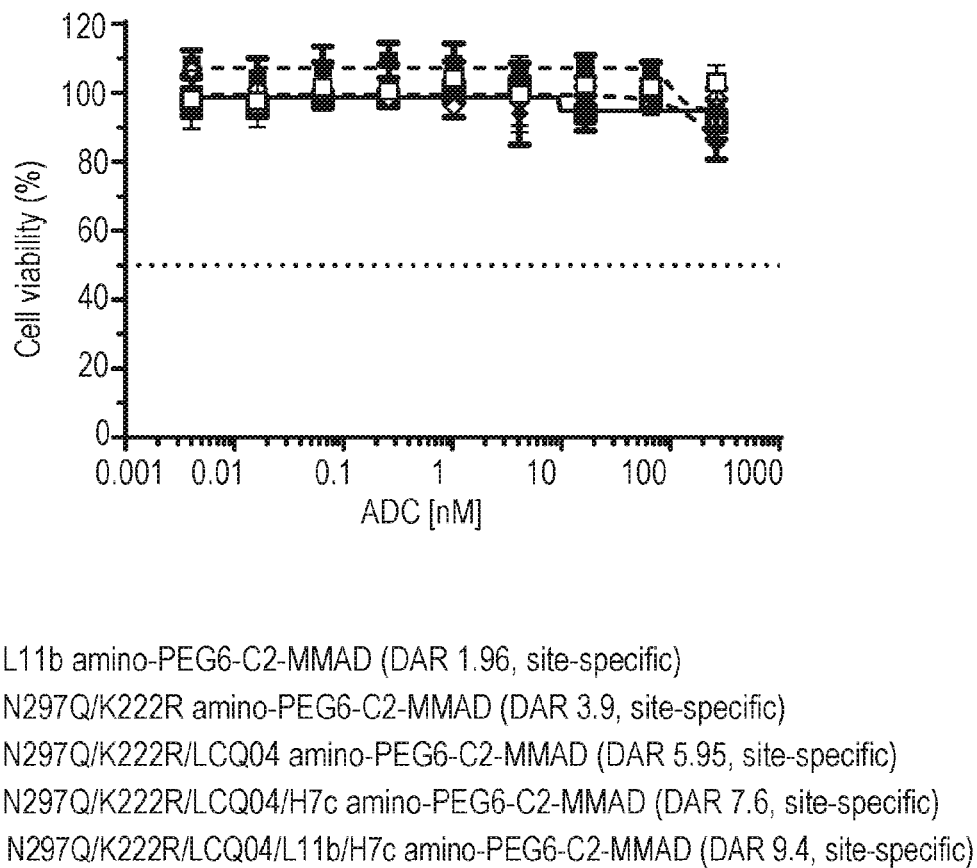
FIG. 17 also shows the absence of unspecific cytotoxicity of the site-specific ADCs with increasing DARs in the non-target expressing SW620 cells in comparison to the site-specific ADCs with a lower DAR (e.g., 1.96 and 3.9).

In vitro cytotoxicity studies of chimeric anti-Trop2 antibodies m7E6 L11b amino-PEG6-C2-MMAD (DAR 1.96, site-specific), m7E6 N297Q/K222R amino-PEG6-C2-MMAD (DAR 3.9, site-specific), m7E6 N297Q/K222R/LCQ04 amino-PEG6-C2-MMAD (DAR 5.95, site-specific), m7E6 N297Q/K222R/LCQ04/H7c amino-PEG6-C2-MMAD (DAR 7.6, site-specific), and N297Q/K222R/LCQ04/L11b/H7c amino-PEG6-C2-MMAD (DAR9.4, site-specific) were performed with non-target-expressing SW620 cells; SW620 is a cancer cell line with no expression of the target (Trop-2−). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50s and the ADC concentration at which 50% of cell killing (i.e., cytotoxicity) occurred were calculated by GraphPad Prism 5 software and expressed as concentration (nM), the maximum cell killing observed at the highest concentration of ADC tested was expressed as percentage of untreated control. The results of the cytotoxicity assay are shown in FIG. 17 and summarized in Table 12. In the concentration range tested all the conjugates showed minimal unspecific cytotoxic activity.

This example demonstrates that increasing the DAR to 9.4 with the conjugate N297Q/K222R/LCQ04/L11 b/H7c amino-PEG6-C2-MMAD did not result in an increase in unspecific cytotoxic activity compared to the conjugates with lower DAR.

TABLE 12

| ADC | DAR | Conjugation | Maximum % cytotoxicity | 50% cytotoxicity (nM) | EC50 (nM) |
|---|---|---|---|---|---|
| m7E6 L11b amino-PEG6-C2-MMAD | 1.96 | site-specific | −3 | not reached | n/a |
| m7E6 N297Q/K222R amino-PEG6-C2-MMAD | 3.90 | site-specific | 1 | not reached | n/a |
| m7E6 N297Q/K222R/LCQ04 amino-PEG6-C2-MMAD | 5.95 | site-specific | 5 | not reached | n/a |
| m7E6 N297Q/K222R/LCQ04/ H7c amino-PEG6-C2-MMAD | 7.60 | site-specific | 15 | not reached | n/a |
| m7E6 N297Q/K222R/LCQ04/ L11b/H7c amino-PEG6-C2-MMAD | 9.40 | site-specific | 8 | not reached | n/a |

Example 15

Cytotoxicity of Increasingly Higher Loaded, Site-Specifically Conjugated Anti-BCMA ADCs in Cells with Low Expression and High Expression of the Target BCMA This example illustrates the in vitro cytotoxicity of higher loaded ADCs (e.g., DAR 5.95 (site-specific conjugation)) in low and medium target expressing L363 and MM1.S cells, respectively.

In vitro cytotoxicity studies of human anti-BCMA (B-Cell Maturation Antigen) antibody (Ab1) conjugated with linker-payload, including Ab1-LCQ05/K222R-splicostatin ((2S, 3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate) (DAR 1.9, site-specific), Ab1-LCQ04/K222R-splicostatin (DAR 1.9, site-specific), Ab1-N297Q/K222R-splicostatin (DAR 3.7, site-specific), and Ab1-N297Q/

Figure 18A:
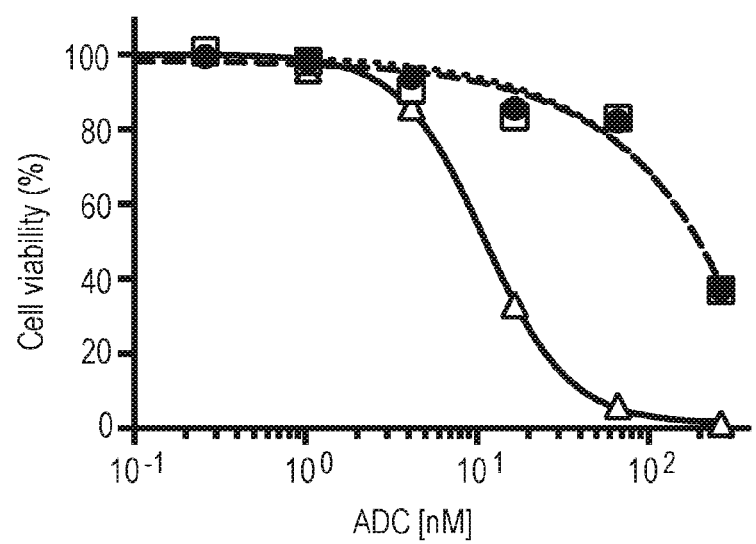
FIGS. 18A and 18B show the in vitro efficacy of the site-specific ADCs with increasing DARs in comparison to the site-specific ADCs with a lower DAR (e.g., 1.9 and 3.7) in low and medium target expressing L363 and MM1.S cells.
Figure 18B:
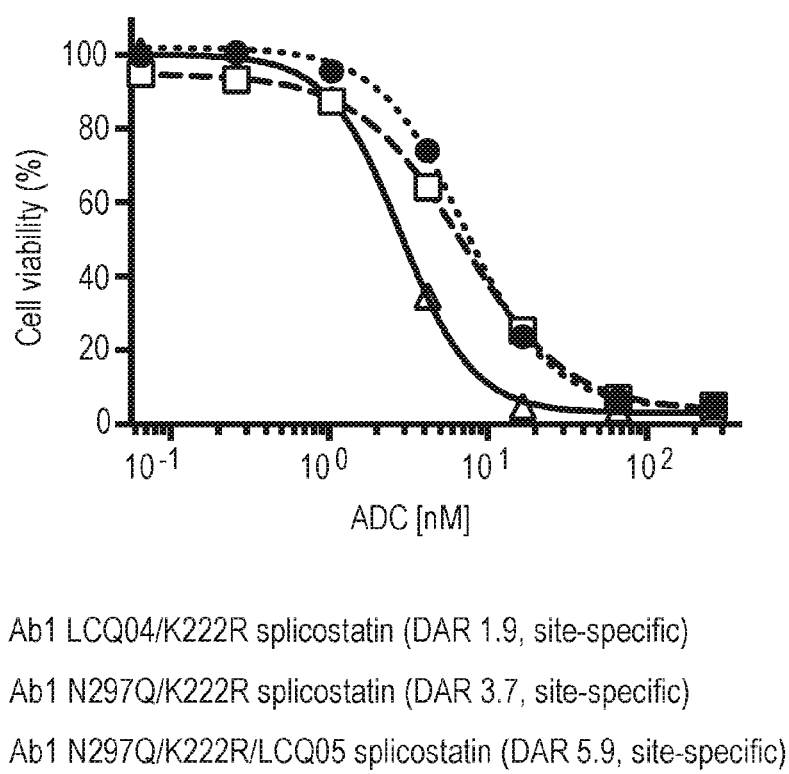

K222R/LCQ05-splicostatin (DAR 5.95, site-specific) were performed with target-expressing L363 (a cancer cell line with low target expression levels (BCMA (+)) and MM1.S (a cancer cell line with medium target expression levels (BCMA (++)). Cells were seeded on clear bottom plates at 3000 cells/well. Cells were treated with 4-fold serially diluted antibody-drug conjugates in triplicates. Cell viability was determined by CellTiter-Glo® Luminescent Cell Viability Assay 96 (Promega, Madison Wis.) 96 hours after treatment. Relative cell viability was determined as percentage of untreated control. EC50 was calculated by Prism software. FIGS. 18A and 18B show that increased cell killing activity and potency positively correlate with low (e.g. 1.9 and 3.7) as compared to high (e.g. 5.9) payload loading of the ADCs.

Accordingly, this example also demonstrates that increased cell killing activity and potency positively correlate with payload loading of the ADCs on cells such as low target expressing L363 and high target expressing MM1.S.

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein.

While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An antibody-drug conjugate comprising the formula: antibody-(T—(X—Y—Z))$_c$, wherein:

T is a glutamine-containing tag engineered at a specific site;

X is an amine donor unit; Y is a linker; and Z is an agent moiety;

X—Y—Z is an amine donor agent site-specifically conjugated to the glutamine-containing tag;

c is an integer from 6 to 20;

wherein the antibody comprises an amino acid modification at positions K222, K340, and/or K370; and wherein the amine donor agent is site-specifically conjugated to the glutamine-containing tag on the antibody at positions according to EU number selected from the group consisting of S60-R61, R108, T135, S160, S168, S190-192, P189-S192, G200-S202, T223-T225, T223, L251-S254, M252-I253, E294-N297, E293-N297, and/or G385; and wherein the glutamine-containing tag is inserted in the antibody or replaces one or more endogenous amino acids in the antibody.

2. The conjugate of claim 1, wherein the antibody is a monoclonal antibody, a polyclonal antibody, a human antibody, a humanized antibody, a chimeric antibody, a bispecific antibody, a minibody, a diabody, or an antibody fragment.

3. The conjugate of claim 1, wherein the amino acid modification is a substitution from lysine (K) to arginine (R).

4. The conjugate of claim 1, wherein c is an integer from 6 to 8.

5. The conjugate of claim 4, wherein c is 6.

6. The conjugate of claim 4, wherein c is 8.

7. The conjugate of claim 4, wherein the amine donor agent is site-specifically conjugated to the glutamine-containing tag inserted after amino acid position T135 in the antibody heavy chain.

8. The conjugate of claim 4, wherein the amine donor agent is site-specifically conjugated to the glutamine-containing tag at amino acid positions G200-S202 in the antibody light chain, wherein the endogenous amino acid residues are replaced with the glutamine-containing tag.

9. The conjugate of claim 1, comprising the amine donor agent site-specifically conjugated to the glutamine-containing tag
  a) at a carboxyl terminus of a light chain of the antibody;
  b) after amino acid position T135 in the antibody heavy chain; and
  c) at amino acid positions G200-S202 in the antibody light chain, wherein the endogenous amino acid residues are replaced with the glutamine-containing tag;
  wherein c is an integer from 6 to 8.

10. The conjugate of claim 1, wherein the glutamine-containing tag comprises an amino acid sequence selected from the group consisting of Q, LQG, LLQGG (SEQ ID NO:1), LLQG (SEQ ID NO:2), LSLSQG (SEQ ID NO:3), GGGLLQGG (SEQ ID NO:4), GLLQG (SEQ ID NO:5), LLQ, GSPLAQSHGG (SEQ ID NO:6), GLLQGGG (SEQ ID NO:7), GLLQGG (SEQ ID NO:8), GLLQ (SEQ ID NO:9), LLQLLQGA (SEQ ID NO:10), LLQGA (SEQ ID NO:11), LLQYQGA (SEQ ID NO:12), LLQGSG (SEQ ID NO:13), LLQYQG (SEQ ID NO:14), LLQLLQG (SEQ ID NO:15), SLLQG (SEQ ID NO:16), LLQLQ (SEQ ID NO:17), LLQLLQ (SEQ ID NO:18), LLQGR (SEQ ID NO:19), LLQGPP (SEQ ID NO:20), LLQGPA (SEQ ID NO:21), GGLLQGPP (SEQ ID NO:22), GGLLQGA (SEQ ID NO:23), LLQGPGK (SEQ ID NO:25), LLQGPG (SEQ ID NO:26), LLQGP (SEQ ID NO:27), LLQP (SEQ ID NO:28), LLQPGK (SEQ ID NO:29), LLQAPGK (SEQ ID NO:30), LLQGAPG (SEQ ID NO:31), LLQGAP (SEQ ID NO:32), and LLQLQG (SEQ ID NO:36).

11. The conjugate of claim 10, wherein the glutamine-containing tag is LLQGA (SEQ ID NO: 11), LQG, GGLLQGA (SEQ ID NO:23), LLQGPA (SEQ ID NO:21), LLQGPP (SEQ ID NO:20), GGLLQGPP (SEQ ID NO:22), LLQGSG (SEQ ID NO:13), LLQG (SEQ ID NO:2), LLQYQG (SEQ ID NO:14), LLQLLQG (SEQ ID NO:15), LLQLQG (SEQ ID NO:36), LLQLLQ (SEQ ID NO:18), LLQLQ (SEQ ID NO:17), LLQGR (SEQ ID NO:19), LLQYQGA (SEQ ID NO:12), SLLQG (SEQ ID NO:16), or LLQLLQGA (SEQ ID NO:10).

12. The conjugate of claim 1, wherein the amine donor unit-linker (X—Y) is linear or branched.

13. The conjugate of claim 12, wherein the amine donor unit-linker (X—Y) is selected from the group consisting of Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2, Ac-Lys-Val-Cit-PABC (acetyl-lysine-valine-citrulline-p-aminobenzyloxycarbonyl), amino-PEG6-C2-Val-Cit-PABC, amino-PEG3-C2-Val-Cit-PABC, aminocaproyl-Val-Cit-PABC, [(3R,5R)-1- {3-[2-(2-aminoethoxy)ethoxy]propanoyl}piperidine-3,5-diyl}bis-Val-Cit-PABC, [(3 S,5 S)-1- {3-[2-(2-aminoethoxy)ethoxy]propanoyl}piperidine-3,5-diyl}bis-Val-Cit-PAB C, putrescine, and Ac-Lys-putrescine.

14. The conjugate of claim 1, wherein the agent moiety is a cytotoxic agent.

15. The conjugate of claim 14, wherein the cytotoxic agent is selected from the group consisting of an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, isosteres, analogs, or derivatives thereof.

16. The conjugate of claim 1, wherein the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-LysGly-MMAD, amino-PEG3-C2-MMAD, amino-PEG6-C2-MMAD, amino-PEG3-C2-amino-nonanoyl-MMAD, aminocaproyl-Val-Cit-PABC-MMAD, amino-PEG3-C2-Val-Cit-PABC-MMAD, amino-PEG6-C2-Val-Cit-PABC-MMAD, Ac-Lys-Val-Cit-PABC-MMAD, aminocaproyl-MMAD, Ac-Lys-β-Ala-MMAD, amino-PEG2-C2-MMAE, aminocaproyl-MMAE, amino-PEG3-C2-MMAE, aminocaproyl-MMAF, aminocaproyl-Val-Cit-PABC-MMAE, amino-PEG-6-C2-Val-Cit-PABC-MMAE, Ac-Lys-Val-Cit-PABC-MMAE, aminocaproyl-Val-Cit-PABC-MMAF, amino-PEG-6-C2-Val-Cit-PABC-MMAF, Ac-Lys-Val-Cit-PABC-MMAF, amino-PEG6-C2-Val-Cit-PAB C-0101, Ac-Lys-Val-Cit-PABC-0101, putrescinyl-geldanamycin, Ac-Lys-putrescinyl-geldanamycin, aminocaproyl-3377, amino-PEG6-C2-3377, aminocaproyl-0131, amino-PEG6-C2-0131, aminocaproyl-0121, amino-PEG6-C2-0121, [(3R,5R)-1-{3-[2-(2-aminoethoxy)ethoxy]propanoyl}piperidine-3,5-diyl]bis-Val-Cit-PABC-MMAD, [(3R,5R)-1-{3-[2-(2-aminoethoxy)ethoxy]propanoyl}piperidine-3,5-diyl]bis-Val-Cit-PABC-MMAe, 2-aminoethoxy-PEG6-NODAGA, and N-2-acetyl-L-lysyl-L-valyl-N~5~-carbamoyl-N-[4-({[(2-{[(3R,5 S,7R, 8R)-8-hydroxy-7-{(1E,3E)-5-[(2S,3 S,5R,6R)-5-{[(2Z,4 S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide.

17. A pharmaceutical composition comprising the conjugate of claim 1, and a pharmaceutically acceptable excipient.

* * * * *

SEQUENCE LISTING

```
<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Leu Leu Gln Gly Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Leu Leu Gln Gly
1

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Leu Ser Leu Ser Gln Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 4

Gly Gly Gly Leu Leu Gln Gly Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Gly Leu Leu Gln Gly
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gly Ser Pro Leu Ala Gln Ser His Gly Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Gly Leu Leu Gln Gly Gly Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Gly Leu Leu Gln Gly Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Leu Leu Gln
1

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 10

Leu Leu Gln Leu Leu Gln Gly Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Leu Leu Gln Gly Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Leu Leu Gln Tyr Gln Gly Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Leu Leu Gln Gly Ser Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Leu Leu Gln Tyr Gln Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Leu Leu Gln Leu Leu Gln Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16
```

```
Ser Leu Leu Gln Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Leu Leu Gln Leu Gln
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Leu Leu Gln Leu Leu Gln
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Leu Leu Gln Gly Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Leu Leu Gln Gly Pro Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Leu Leu Gln Gly Pro Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22
```

Gly Gly Leu Leu Gln Gly Pro Pro
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Gly Gly Leu Leu Gln Gly Ala
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Leu Leu Gln Gly Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Leu Leu Gln Gly Pro Gly Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26

Leu Leu Gln Gly Pro Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Leu Leu Gln Gly Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic Construct

<400> SEQUENCE: 28

Leu Leu Gln Pro

```
<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Leu Leu Gln Pro Gly Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Leu Leu Gln Ala Pro Gly Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Leu Leu Gln Gly Ala Pro Gly
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct

<400> SEQUENCE: 32

Leu Leu Gln Gly Ala Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Leu Leu Gln Gly Pro Ala
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Leu Leu Gln Gly Pro Pro
1               5
```

```
<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Gly Gly Leu Leu Gln Gly Pro Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Leu Leu Gln Leu Gln Gly
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp
<220> FEATURE:
<221> NAME/KEY: misc_feature
<222> LOCATION: (4)..(4)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp

<400> SEQUENCE: 37

Xaa Xaa Gln Xaa
1

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Leu Gly Gly Gln Gly Gly Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Gly Gly Gly Gln Gly Gly Leu
1               5

<210> SEQ ID NO 40
<211> LENGTH: 7
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa = Gly, Ala, Ser, Leu, Val, Phe, Tyr, Arg,
      Asn, or Glu

<400> SEQUENCE: 40

Gly Xaa Gly Gln Gly Gly Gly
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = Gly, Ala, Ser, Leu, Val, Phe, Tyr, Arg,
      Asn, or Glu

<400> SEQUENCE: 41

Gly Gly Xaa Gln Gly Gly Gly
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa = Gly, Ala, Ser, leu, Val, Phe, Tyr, Arg,
      Asn, or Glu

<400> SEQUENCE: 42

Gly Gly Gly Gln Xaa Gly Gly
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa = Gly, Ala, Ser, Leu, Val, Phe, Tyr, Arg,
      Asn, or Glu

<400> SEQUENCE: 43

Gly Gly Gly Gln Gly Xaa Gly
1               5
```